(12) United States Patent
Huang et al.

(10) Patent No.: US 11,680,248 B2
(45) Date of Patent: Jun. 20, 2023

(54) RECOMBINANT HERPES SIMPLEX VIRUS AND USE THEREOF

(71) Applicants: Xiamen University, Xiamen (CN); Yang Sheng Tang Company, LTD., Haikou (CN)

(72) Inventors: Chenghao Huang, Xiamen (CN); Yong Luo, Xiamen (CN); Quan Yuan, Xiamen (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Haikou (CN)

( * ) Notice: Subject to any disclaimer, the term of this patent is extended or adjusted under 35 U.S.C. 154(b) by 861 days.

(21) Appl. No.: 16/491,699

(22) PCT Filed: Feb. 28, 2018

(86) PCT No.: PCT/CN2018/077518
§ 371 (c)(1),
(2) Date: Sep. 6, 2019

(87) PCT Pub. No.: WO2018/161825
PCT Pub. Date: Sep. 13, 2018

(65) Prior Publication Data
US 2020/0071679 A1 Mar. 5, 2020

(30) Foreign Application Priority Data

Mar. 9, 2017 (CN) .......................... 201710136638.1
May 2, 2017 (CN) .......................... 201710301464.X

(51) Int. Cl.
*C12N 7/00* (2006.01)
*A61P 35/00* (2006.01)
*A61K 35/763* (2015.01)
*C07K 14/005* (2006.01)
*C12N 15/86* (2006.01)

(52) U.S. Cl.
CPC .............. *C12N 7/00* (2013.01); *A61K 35/763* (2013.01); *A61P 35/00* (2018.01); *C07K 14/005* (2013.01); *C12N 15/86* (2013.01); *C12N 2710/16621* (2013.01); *C12N 2710/16622* (2013.01); *C12N 2710/16643* (2013.01); *C12N 2710/16651* (2013.01)

(58) Field of Classification Search
CPC ....................... C12N 7/00; C12N 15/86; C12N 2710/16621; C12N 2710/16622; C12N 2710/16643; C12N 2710/16651; C12N 2710/16632; C12N 5/10; A61K 35/763; A61P 35/00; C07K 14/005; C07K 14/035; A01K 2207/12; A01K 2227/105; A01K 2267/0331
See application file for complete search history.

(56) References Cited

U.S. PATENT DOCUMENTS

| | | | |
|---|---|---|---|
| 6,248,320 B1* | 6/2001 | Coffin | A61P 35/00 435/235.1 |
| 6,573,090 B1* | 6/2003 | Breakefield | A61K 39/12 435/235.1 |
| 8,236,941 B2† | 8/2012 | Yao | |
| 8,709,397 B2* | 4/2014 | Mohr | A61P 37/00 424/229.1 |
| 9,085,777 B2* | 7/2015 | Conner | C12N 15/86 |
| 9,862,932 B2* | 1/2018 | Shah | C12N 7/00 |
| 10,039,796 B2* | 8/2018 | Zhang | A61P 43/00 |
| 10,533,148 B2 | 1/2020 | Li et al. | |
| 2004/0171569 A1* | 9/2004 | Horsburgh | C12N 15/86 536/23.1 |

(Continued)

FOREIGN PATENT DOCUMENTS

| | | |
|---|---|---|
| CN | 101338302 A | 1/2009 |
| CN | 102220292 A | 10/2011 |

(Continued)

OTHER PUBLICATIONS

Luo Y, Lin C, Zou Y, Ju F, Ren W, Lin Y, Wang Y, Huang X, Liu H, Yu Z, Liu P, Tan G, Yuan Q, Zhang J, Huang C, Xia N. Tumor-targeting oncolytic virus elicits potent immunotherapeutic vaccine responses to tumor antigens. Oncoimmunology. Feb. 12, 2020;9(1):1726168. (Year: 2020).*
Hummel et al., "The Role of ICP0-Null HSV-1 and Interferon Signaling Defects in the Effective Treatment of Breast Adenocarcinoma," *Molecular Therapy* 12(6):1101-1110, 2005.
Liu et al., "ICP34.5 deleted herpes simplex virus with enhanced oncolytic, immune stimulating, and anti-tumour properties," *Gene Therapy* 10:292-303, 2003.
Peters et al., "Designing herpes viruses as oncolytics," *Molecular Therapy-Oncolytics* 2:1-14, 2015.
Sokolowski et al., "Oncolytic virotherapy using herpes simplex virus: how far have we come?" *Oncolytic Virotherapy* 4:207-219, 2015.

(Continued)

*Primary Examiner* — Rachel B Gill
(74) *Attorney, Agent, or Firm* — Seed IP Law Group LLP

(57) ABSTRACT

The invention relates to the field of virology and tumor therapy. In particular, the present invention provides a recombinant herpes simplex virus (HSV) capable of specifically replicating at a high level in a tumor cell and effectively killing the tumor cell, but replicating at low levels in normal cells, thereby the recombinant herpes simplex virus of the present invention not only has high lethality against tumor cells, but also has significantly decreased side effects (especially neurotoxicity). Further, the present invention relates to a viral vector constructed based on the recombinant herpes simplex virus, a pharmaceutical composition comprising the recombinant herpes simplex virus or the viral vector, and the use of the recombinant herpes simplex virus or the viral vector. The recombinant herpes simplex virus of the present invention can be used to infect and kill tumor cells, and can be used for gene drug delivery into tumor cells for gene therapy.

19 Claims, 10 Drawing Sheets

Specification includes a Sequence Listing.

(56) References Cited

U.S. PATENT DOCUMENTS

| | | | | |
|---|---|---|---|---|
| 2009/0176203 A1* | 7/2009 | Conner | ............ | C12N 15/86 435/235.1 |
| 2019/0046594 A1* | 2/2019 | O'Shea | ............ | C12N 15/63 |
| 2019/0169253 A1* | 6/2019 | Jia | ............ | C07K 14/7155 |
| 2019/0276845 A1* | 9/2019 | Glorioso, III | ...... | A61K 48/0066 |
| 2019/0316176 A1 | 10/2019 | Zhang et al. | | |

FOREIGN PATENT DOCUMENTS

| | | |
|---|---|---|
| CN | 102666843 A | 9/2012 |
| WO | 2011/079073 A2 | 6/2011 |
| WO | 2016/146535 A1 | 9/2016 |
| WO | 2020/106566 † | 5/2020 |

OTHER PUBLICATIONS

Hao et al., "The Advances of Oncolytic Herpes Simplex Virus in Cancer Therapy", *Chinese Journal of Virology* 32(4):516-522. 2016 (with English Abstract).

Hu et al., "Research progress of oncolytic herpes simplex virus in treating tumors," *Oncology Progress* 14(8):730-733, 737, 2016 (w/ English Abstract).

Peng-Fei et al., "The research progress on oncolytic herpes simplex virus type 1,"*Microbiology China* 42(9):1795-1801, 2015 (w/ English Abstract).

Wong et al., "Cytokine Gene Transfer Enhances Herpes Oncolytic Therapy in Murine Squamous Cell Carcinoma," *Human Gene Therapy* 12:253-265, Feb. 10, 2001.

Zhang et al., "A novel oHSV-1 targeting telomerase reverse transcriptase-positive cancer cells via tumor-specific promoters regulating the expression of ICP4," *Oncotarget* 6(24):20345-20355, May 6, 2015.

Bolovan et al., "ICP34.5 Mutants of Herpes Simplex Virus Type 1 Strain 17syn+ Are Attenuated for Neurovirulence in Mice and for Replication in Confluent Primary Mouse Embryo Cell Cultures," *Journal of Virology*, 68(1):48-55, 1994.

\* cited by examiner
† cited by third party

SEQUENCE LISTING

```
<160> NUMBER OF SEQ ID NOS: 23

<210> SEQ ID NO 1
<211> LENGTH: 5844
<212> TYPE: DNA
<213> ORGANISM: herpes simplex virus 1

<400> SEQUENCE: 1
gcaaaaaagg cgggcggcgg tccgggcggc gtgcgcgcgc gcggcgggcg tgggggcgg      60 ggccgcggga gcggggagg agcggggag gagcgggggg aggagcgggg ggaggagcgg     120
ggggaggagc gggggagga gcggggggag gagcgggggg aggagcgggg ggaggagcgg     180
ggggaggagc gggggagga gcggggggag gagcgggggg aggagcgggg ggaggagcgg     240
ggggaggagc gggggagga gcggggggag gagcggggga ggagcggcca gacccccggaa    300 acgggccccc cccaaaacac accccccggg ggtcgcgcgc ggcccttaa aggcgggcgg     360 cgggcagccc gggccccccg cggccgagac tagcgagtta gacaggcaag cactactcgc    420
ctctgcacgc acatgcttgc ctgtcaaact ctaccaccc ggcacgctct ctgtctccat     480
ggcccgccgc cgccatcgcg gccccgccg cccccggccg cccgggccca cgggcgcggt    540
cccaaccgca cagtcccagg taacctccac gcccaactcg gaacccgtgg tcaggagcgc    600
gcccgcggcc gccccgccgc cgcccccgc cagtgggccc ccgccttctt gttcgctgct    660
gctgcgccag tggctccacg ttcccgagtc cgcgtccgac gacgacgacg acgactggcc    720
ggacagcccc ccgcccgagc cggcgccaga ggccggccc accgccgccg ccccccgccc    780
ccggtcccca ccgcccggcg cgggcccggg gggcggggct aaccctccc accccctc     840
```

```
acgccccttc cgccttccgc cgcgcctcgc cctccgcctg cgcgtcaccg cagagcacct    900
ggcgcgcctg cgcctgcgac gcgcgggcgg ggagggggcg ccgaagcccc ccgcgacccc    960
cgcgaccccc gcgaccccca cgcgggtgcg cttctcgccc cacgtccggg tgcgccacct   1020
ggtggtctgg gcctcggccg cccgcctggc gcgccgcggc tcgtgggccc gcgagcgggc   1080
cgaccgggct cggttccggc gccgggtggc ggaggccgag gcggtcatcg ggccgtgcct   1140
ggggcccgag gcccgtgccc gggccctggc ccgcggagcc ggcccggcga actcggtcta   1200
acgttacacc cgaggcggcc tgggtcttcc gcggagctcc cgggagctcc gcaccaagcc   1260
gctctccgga gagacgatgg caggagccgc gcatatatac gcttggagcc ggcccgcccc   1320
cgaggcgggc ccgccctcgg agggcgggac tggccaatcg gcggccgcca gcgcggcggg   1380
gcccggccaa ccagcgtccg ccgagtcgtc ggggcccggc ccactgggcg gtaactcccg   1440
cccagtgggc cgggccgccc acttcccggt atggtaatta aaaacttgca gaggccttgt   1500
tccgcttccc ggtatggtaa ttagaaactc attaatgggc ggccccggcc gcccttcccg   1560
cttccggcaa ttcccgcggc ccttaatggg caaccccggt attccccgcc tcccgcgccg   1620
cgcgtaacca ctcccctggg gttccggggtt atgttaattg ctttttttggc ggaacacacg   1680 gccctcgcg cattggcccg cgggtcgctc aatgaacccg cattggtccc ctggggttcc   1740
gggtatggta atgagtttct cgggaaggc gggaagcccc ggggcaccga cgcaggccaa   1800 gccctgttg cgtcggcggg aggggcatgc taatgggggtt cttgggggga caccgggttg   1860 gtccccaaa tcgggggccg ggccgtgcat gctaatgata ttctttgggg gcgccgggtt   1920 ggtcccggg gacggggccg ccccgcgtg ggcctgcctc ccctgggacg cgcggccatt   1980
gggggaatcg tcactgccgc cccttttgggg aggggaaagg cgtgggtat aagttagccc   2040 tggcccgacg gtctggtcgc atttgcacct cggcactcgg agcgagacgc agcagccagg   2100
cagactcggg ccgccccctc tccgcatcac cacagaagcc ccgcctacgt tgcgaccccc   2160
agggaccctc cgtcagcgac cctccagccg catacgaccc ccatggagcc ccgccccgga   2220
gcgagtaccc gccggcctga gggccgcccc cagcgcgagg tgaggggccg ggcgccatgt   2280
ctggggcgcc atgttggggg gcgccatgtt ggggggcgcc atgttgggggg accccccgacc   2340 cttacactgg aaccggccgc catgttgggg gaccccccact catacacggg agccgggcgc   2400
catgttgggg cgccatgtta gggggcgtgg aaccccgtga cactatatat acagggaccg   2460
ggggcgccat gttaggggggc gcggaacccc ctgaccctat atatacaggg accggggtcg   2520
ccctgttagg ggtcgccatg tgaccccctg actttatata tacagacccc caacacctac   2580
acatggcccc tttgactcag acgcagggcc cggggtcgcc gtgggacccc cctgactcat   2640
acacagagac acgccccccac aacaaacaca cagggaccgg ggtcgccgtg ttaggggggcg   2700 tggtccccac tgactcatac gcagggcccc cttactcaca cgcatctagg ggggtgggga   2760
ggagccgccc gccatatttg ggggacgccg tgggaccccc gactccggtg cgtctggagg   2820
gcgggagaag agggaagaag aggggtcggg atccaaagga cggacccaga ccacctttgg   2880
ttgcagaccc ctttctcccc cctcttccga ggccagcagg ggggcaggac tttgtgaggc   2940
ggggggggag ggggaactcg tgggcgctga ttgacgcggg aaatcccccc attcttaccc   3000 gcccccctt ttttcccctc agcccgcccc ggatgtctgg gtgtttccct gcgaccgaga   3060
cctgccggac agcagcgact cggaggcgga gaccgaagtg gggggggcggg gggacgccga   3120 ccaccatgac gacgactccg cctccgaggc ggacagcacg gacacggaac tgttcgagac   3180
ggggctgctg gggccgcagg gcgtggatgg ggggggcggtc tcggggggga gccccccccg   3240
```

```
cgaggaagac cccggcagtt gcggggcgc cccccctcga ggacgggg ggagcgacga   3300
gggcgacgtg tgcgccgtgt gcacggatga gatcgcgccc cacctgcgct gcgacacctt   3360
cccgtgcatg caccgcttct gcatcccgtg catgaaaacc tggatgcaat tgcgcaacac   3420
ctgcccgctg tgcaacgcca agctggtgta cctgatagtg ggcgtgacgc ccagcgggtc   3480
gttcagcacc atcccgatcg tgaacgaccc ccagaccgc atggaggccg aggaggccgt   3540
cagggcgggc acgccgtgg actttatctg gacgggcaat cagcggttcg ccccgcggta   3600
cctgaccctg ggggggcaca cggtgagggc cctgtcgccc acccaccctg agcccaccac   3660
ggacgaggat gacgacgacc tggacgacgg tgaggcgggg gggcggcgag gaccctgggg   3720
gaggaggagg aggggggggg gagggaggaa taggcgggcg ggcgggcgag gaaagggcgg   3780
gccggggagg gggcgtaacc tgatcgcgcc cccgttgtc tcttgcagca gactacgtac   3840
cgcccgcccc ccgccggacg ccccgcgccc cccacgcag aggcgccgcc gcgcccccg   3900
tgacgggcgg ggcgtctcac gcagcccccc agcggccgc ggctcggaca cgcgcccct   3960
cggcgcccat cgggccacac ggcagcagta acactaacac caccaccaac agcagcggcg   4020
gcggcggctc ccgccagtcg cgagccgcgg tgccgcgggg ggcgtctggc ccctccgggg   4080
gggttgggt tgttgaagcg gaggcggggc ggccgagggg ccggacgggc ccccttgtca   4140
acagacccgc ccccttgca aacaacagag accccatagt gatcagcgac tccccccgg   4200
cctctcccca caggccccc gcggcgccca tgccaggctc cgccccccgc cccggtcccc   4260
ccgcgtccgc ggccgcgtcg ggcccgcgc gccccgcgc ggccgtggcc ccgtgtgtgc   4320
gggcgccgcc tccggggccc ggccccgcg ccccggcccc cggggcggag ccggccgccc   4380
gccccgcgga cgcgcgccgt gtgccccagt cgcactcgtc cctggctcag gccgcgaacc   4440
aagaacagag tctgtgccgg gcgcgtgcga cggtggcgcg cggctcgggg gggccgggcg   4500
tggagggtgg acacgggccc tcccgcgcg ccgcccctc cggcgccgcc cctccggcg   4560
ccccccgct ccctccgcc gcctctgtcg agcaggaggc ggcggtgcgt ccgaggaaga   4620
ggcgcgggtc gggccaggaa aaccctccc ccagtccac gcgtcccccc ctcgcgccgg   4680
cagggggccaa gagggcggcg acgcaccccc cctccgactc agggccgggg gggcgcggcc   4740
agggagggcc cggacccccc ctgacgtcct cggcggcctc cgcctcttcc tcctccgcct   4800
cttcctcctc ggccccgact cccgcggggg ccacctcttc cgccaccggg gccgcgtcct   4860
cctccgcttc cgcctcctcg ggcggggccg tcggtgccct gggagggaga caagaggaaa   4920
cctccctcgg cccccgcgct gcttctgggc cgcggggcc gaggaagtgt gcccggaaga   4980
cgcgccacgc ggagacttcc ggggccgtcc ccgcgggcgg cctcacgcgc tacctgccca   5040
tctcggggt ctctagcgtg tcgcccctgt cgccttacgt gaacaagacg atcacgggg   5100
actgcctgcc catcctggac atggagacgg ggaacatcgg ggcgtacgtg tcctggtgg   5160
accagacggg aaacatggcg acccggctgc gggccgcgt ccccggctgg agccgccgca   5220
ccctgctccc cgagaccgcg ggtaaccacg tgacgccccc cgagtacccg acggcccccg   5280
cgtcggagtg aacagcctc tggatgaccc ccgtggggaa catgctgttc gaccagggca   5340
ccctagtggg cgccctggac ttccgcagcc tgcggtctcg gcaccgtgg tccggggagc   5400
aggggggcgtc gacccgggac gagggaaaac aataagggac gcccccgtgt ttgtggggag   5460
ggggggtcg ggcgctggt ggtctctggc cgcgcccact acaccagcca atccgtgtcg   5520
gggaggtgga aagtgaaaga cacgggcacc acacaccagc gggtcttttg tgttggccct   5580
```

```
aataaaaaaa actcagggga tttttgctgt ctgttgggaa ataaaggttt acttttgtat      5640
cttttccctg tctgtgttgg atgtatcgcg ggggtgcgtg ggagtggggg tgcgtgggag      5700 tggggtgcg tgggagtggg ggtgcgtggg agtgggggtg cgtgggagtg ggggtgcgtg       5760
ggagtggggg tgcgtgggag tggggtgcg tgggagtggg ggtgcgtggg agtgggggtg      5820
ccatgttggg caggctctgg tgtt                                            5844
```

<210> SEQ ID NO 2
<211> LENGTH: 3049
<212> TYPE: DNA
<213> ORGANISM: Artificial Sequence
<220> FEATURE:
<223> OTHER INFORMATION: LacZ gene

<400> SEQUENCE: 2

```
gtcgttttac aacgtcgtga ctgggaaaac cctggcgtta cccaacttaa tcgccttgca       60
gcacatcccc ctttcgccag ctggcgtaat agcgaagagg cccgcaccga tcgcccttcc      120
caacagttgc gcagcctgaa tggcgaatgg cgctttgcct ggtttccggc accagaagcg      180
gtgccggaaa gctggctgga gtgcgatctt cctgaggccg atactgtcgt cgtcccctca      240
aactggcaga tgcacggtta cgatgcgccc atctacacca acgtgaccta tcccattacg      300
gtcaatccgc cgtttgttcc cacggagaat ccgacgggtt gttactcgct cacatttaat      360
gttgatgaaa gctggctaca ggaaggccag acgcgaatta ttttttgatgg cgttaactcg      420 gcgtttcatc tgtggtgcaa cgggcgctgg gtcggttacg ccaggacag tcgtttgccg      480 tctgaatttg acctgagcgc attttttacgc gccgagaaaa accgcctcgc ggtgatggtg      540
ctgcgctgga gtgacggcag ttatctggaa gatcaggata tgtggcggat gagcggcatt      600
ttccgtgacg tctcgttgct gcataaaccg actacacaaa tcagcgattt ccatgttgcc      660
actcgcttta atgatgattt cagccgcgct gtactggagg ctgaagttca gatgtgcggc      720
gagttgcgtg actacctacg ggtaacagtt tcttttatggc agggtgaaac gcaggtcgcc      780
agcggcaccg cgcctttcgg cggtgaaatt atcgatgagc gtggtggtta tgccgatcgc      840
gtcacactac gtctgaacgt cgaaaacccg aaactgtgga gcgccgaaat cccgaatctc      900
tatcgtgcgg tggttgaact gcacaccgcc gacggcacgc tgattgaagc agaagcctgc      960
gatgtcggtt tccgcgaggt gcggattgaa atggtctgc tgctgctgaa cggcaagccg      1020
ttgctgattc gaggcgttaa ccgtcacgag catcatcctc tgcatggtca ggtcatggat     1080
gagcagacga tggtgcagga tatcctgctg atgaagcaga acaactttaa cgccgtgcgc     1140
tgttcgcatt atccgaacca tccgctgtgg tacacgctgt gcgaccgcta cggcctgtat     1200
gtggtggatg aagccaatat tgaaacccac ggcatggtgc aatgaatcg tctgaccgat     1260 gatccgcgct ggctaccggc gatgagcgaa cgcgtaacgc gaatggtgca gcgcgatcgt     1320
aatcacccga gtgtgatcat ctggtcgctg ggaatgaat caggccacgg cgctaatcac     1380
gacgcgctgt atcgctggat caaatctgtc gatccttccc gcccggtgca gtatgaaggc     1440
ggcggagccg acaccacggc caccgatatt atttgcccga tgtacgcgcg cgtggatgaa     1500
gaccagcccc tccccggctgt gccgaaatgg tccatcaaaa aatggctttc gctacctgga     1560
gagacgcgcc cgctgatcct ttgcgaatac gcccacgcga tgggtaacag tcttggcggt     1620
ttcgctaaat actggcaggc gtttcgtcag tatccccgtt tacagggcgg cttcgtctgg     1680
gactgggtgg atcagtcgct gattaaatat gatgaaaacg gcaacccgtg gtcggcttac     1740
ggcggtgatt ttgccgatac gccgaacgat cgccagttct gtatgaacgg tctggtctttt     1800
```

```
gccgaccgca cgccgcatcc agcgctgacg gaagcaaaac accagcagca gttttcccag   1860
ttccgtttat ccgggcaaac catcgaagtg accagcgaat acctgttccg tcatagcgat   1920
aacgagctcc tgcactggat ggtggcgctg gatggtaagc cgctggcaag cggtgaagtg   1980
cctctggatg tcgctccaca aggtaaacag ttgattgaac tgcctgaact accgcagccg   2040
gagagcgccg ggcaactctg gctcacagta cgcgtagtgc aaccgaacgc gaccgcatgg   2100
tcagaagccg ggcacatcag cgcctggcag cagtggcgtc tggcgaaaaa cctcagtgtg   2160
acgctccccg ccgcgtccca cgccatcccg catctgacca ccagcgaaat ggatttttgc   2220
atcgagctgg gtaataagcg ttggcaattt aaccgccagt caggctttct ttcacagatg   2280
tggattggcg ataaaaaaca actgctgacg ccgctgcgcg atcagttcac ccgtgcaccg   2340
ctggataacg acattggcgt aagtgaagcg acccgcattg accctaacgc ctgggtcgaa   2400
cgctggaagg cggcgggcca ttaccaggcc gaaagcagcg ttgttgcagt gcacggcaga   2460
tacacttgct gatgcggtgc tgattacgac cgctcacgcg tggcagcatc aggggaaaac   2520
cttatttatc agccggaaaa cctaccggat tgatggtagt ggtcaaatgg cgattaccgt   2580
tgatgttgaa gtggcgagcg atacaccgca tccggcgcgg attggcctga actgccagct   2640
ggcgcaggta gcagagcggg taaactggct cggattaggg ccgcaagaaa actatcccga   2700
ccgccttact gccgcctgtt ttgaccgctg ggatctgcca ttgtcagaca tgtatacccc   2760
gtacgtcttc ccgagcgaaa acggtctgcg ctgcgggacg cgcgaattga attatggccc   2820
acaccagtgg cgcggcgact tccagttcaa catcagccgc tacagtcaac agcaactgat   2880
ggaaaccagc catcgccatc tgctgcacgc ggaagaaggc acatggctga atatcgacgg   2940
tttccatatg gggattggtg gcgacgactc ctggagcccg tcagtatcgg cggaattcca   3000
gctgagcgcc ggtcgctacc attaccagtt ggtctggtgt caaaaataa             3049
```

<210> SEQ ID NO 3
<211> LENGTH: 562
<212> TYPE: DNA
<213> ORGANISM: herpes simplex virus 1

<400> SEQUENCE: 3

```
ccacctggtg ttttgtctcc accatcggcc tgacagagct gtattgtatt ctgcggcggg     60
gcccggcccc caagaacgca gacaaggccg ccgccccggg gcgatccaag gggctgtcgg    120
gcgtctgcgg gcgctgttgt tccatcatcc tgtcgggcat cgcaatgcga ttgtgttata    180
tcgccgtggt ggccggggtg gtgctcgtgg cgcttcacta cgagcaggag atccagaggc    240
gcctgtttga tgtatgacgt cacatccagg ccggcggaaa ccggaacggc atatgcaaac    300
tggaaactgt cctgtcttgg ggcccaccca cccgacgcgc catatgtaaa tgaaaatcgt    360
tcccccgagg ccatgtgtag cctggatccc aacgaccccg cccatgggtc ccaattggcc    420
gtcccgttac caagaccaac ccagccagcg tatccacccc cgcccgggtc cccgcggaag    480
cggaacggtg tatgtgatat gctaattaaa tacatgccac gtacttatgg tgtctgattg    540
gtccttgtct gtgccggagg tg                                             562
```

<210> SEQ ID NO 4
<211> LENGTH: 1605
<212> TYPE: DNA
<213> ORGANISM: herpes simplex virus 1

<400> SEQUENCE: 4

| | |
|---|---:|
| accggtgcgc caccaccaga ggccatatcc gacaccccag ccccgacggc agccgacagc | 60 |
| ccggtcatgg cgactgacat tgatatgcta attgacctcg gcctggacct ctccgacagc | 120 |
| gatctggacg aggaccccc cgagccggcg gagagccgcc gcgacgacct ggaatcggac | 180 |
| agcaacgggg agtgttcctc gtcggacgag gacatggaag accccacgg agaggacgga | 240 |
| ccggagccga tactcgacgc cgctcgcccg gcggtccgcc cgtctcgtcc agaagacccc | 300 |
| ggcgtaccca gcacccagac gcctcgtccg acggagcggc agggcccaa cgatcctcaa | 360 |
| ccagcgcccc acagtgtgtg gtcgcgcctc ggggcccggc gaccgtcttg ctccccgag | 420 |
| cggcacgggg gcaaggtggc ccgcctccaa cccccaccga ccaaagccca gcctgcccgc | 480 |
| ggcggacgcc gtgggcgtcg caggggtcgg ggtcgcggtg gtcccggggc cgccgatggt | 540 |
| ttgtcggacc cccgccggcg tgccccaga accaatcgca accgggggg accccgcccc | 600 |
| ggggcggggt ggacggacgg ccccggcgcc ccccatgggc aggcgtggcg cggaagtgag | 660 |
| cagcccgacc cacccggagg cccgcggaca cggagcgtgc gccaagcacc ccccccgcta | 720 |
| atgacgctgg cgattgcccc cccgcccgcg gaccccgcg ccccggcccc ggagcgaaag | 780 |
| gcgcccgccg ccgacaccat cgacgccacc acgcggttgg tcctgcgctc catctccgag | 840 |
| cgcgcggcgg tcgaccgcat cagcgagagc ttcggccgca cgcacaggt catgcacgac | 900 |
| cccctttgggg ggcagccgtt tcccgccgcg aatagcccct gggccccggt gctggcgggc | 960 |
| caaggagggc cctttgacgc cgagaccaga cgggtctcct gggaaccttt ggtcgcccac | 1020 |
| ggcccgagcc tctatcgcac ttttgccggc aatcctcggg ccgcatcgac cgccaaggcc | 1080 |
| atgcgcgact gcgtgctgcg ccaagaaaat ttcatcgagg cgctggcctc cgccgacgag | 1140 |
| acgctggcgt ggtgcaagat gtgcatccac cacaacctgc cgctgcgccc ccaggacccc | 1200 |
| attatcggga cggccgcggc ggtgctggat aacctcgcca cgcgcctgcg gcccttctc | 1260 |
| cagtgctacc tgaaggcgcg aggcctgtgc ggcctggacg aactgtgttc gcggcggcgt | 1320 |
| ctggcggaca ttaaggacat tgcatccttc gtgtttgtca ttctggccag gctcgccaac | 1380 |
| cgcgtcgagc gtggcgtcgc ggagatcgac tacgcgaccc ttggtgtcgg ggtcggagag | 1440 |
| aagatgcatt tctacctccc cggggcctgc atggcgggcc tgatcgaaat cctagacacg | 1500 |
| caccgccagg agtgttcgag tcgtgtctgc gagttgacgg ccagtcacat cgtcgccccc | 1560 |
| ccgtacgtgc acggcaaata tttttattgc aactccctgt tttag | 1605 |

<210> SEQ ID NO 5
<211> LENGTH: 260
<212> TYPE: DNA
<213> ORGANISM: Homo sapiens

<400> SEQUENCE: 5

| | |
|---|---:|
| ctgcgctgtc ggggccaggc cgggctccca gtggattcgc gggcacagac gcccaggacc | 60 |
| gcgcttccca cgtggcggag ggactgggga cccgggcacc cgtcctgccc cttccacttc | 120 |
| cagctccgcc tcctccgcgc ggaccccgcc ccgtcccgac ccctcccggg tccccggccc | 180 |
| agccccctcc gggccctccc agcccctccc cttcctttcc gcggccccgc cctctcctcg | 240 |
| cggcgcgagt ttcaggcagc | 260 |

<210> SEQ ID NO 6
<211> LENGTH: 4930
<212> TYPE: DNA
<213> ORGANISM: herpes simplex virus 1

<400> SEQUENCE: 6

```
catggcccgc cgccgccatc gcggccccg  ccgccccgg  ccgcccggc  ccacgggcgc   60
ggtcccaacc gcacagtccc aggtaacctc cacgcccaac tcggaacccg tggtcaggag  120
cgcgcccgcg gccgcccgc  cgccgccccc cgccagtggg ccccgccctt cttgttcgct  180
gctgctgcgc cagtggctcc acgttcccga gtccgcgtcc gacgacgacg acgacgactg  240
gccggacagc cccccgcccg agccggcgcc agaggcccgg cccaccgccg ccgcccccg   300
cccccggtcc ccaccgcccg gcgcgggccc ggggggcggg gctaacccct cccacccccc  360
ctcacgcccc ttccgccttc cgccgcgcct cgccctccgc ctgcgcgtca ccgcagagca  420
cctggcgcgc ctgcgcctgc gacgcgcggg cggggagggg gcgccgaagc cccccgcgac  480
ccccgcgacc cccgcgaccc ccacgcgggt gcgcttctcg ccccacgtcc gggtgcgcca  540
cctggtggtc tgggcctcgg ccgcccgcct ggcgcgccgc ggctcgtggg cccgcgagcg  600
ggccgaccgg gctcggttcc ggcgccgggt ggcggaggcc gaggcggtca tcgggccgtg  660
cctggggccc gaggcccgtg cccggggcct ggcccgcgga ccggcccgg  cgaactcggt  720
ctaacgttac acccgaggcg gcctgggtct tccgcggagc tcccgggagc tccgcaccaa  780
gccgctctcc ggagagacga tggcaggagc cgcgcatata tacgcttgga gccggcccgc  840
ccccgaggcg ggcccgccct cggagggcgg gactggccaa tcgcggccg  ccagcgcggc  900
ggggccggc  caaccagcgt ccgccgagtc gtcggggccc ggcccactgg gcggtaactc  960
ccgcccagtg ggccgggccg cccacttccc ggtatggtaa ttaaaaactt gcagaggcct 1020
tgttccgctt cccggtatgg taattagaaa ctcattaatg gcggccccg  gccgcccttc 1080
ccgcttccgg caattcccgc ggcccttaat gggcaacccc ggtattcccc gcctcccgcg 1140
ccgcgcgtaa ccactcccct ggggttccgg gttatgttaa ttgcttttttt ggcggaacac 1200
acggcccctc gcgcattggc ccgcgggtcg ctcaatgaac ccgcattggt ccctgggt   1260
tccgggtatg gtaatgagtt tcttcgggaa ggcgggaagc cccggggcac cgacgcaggc 1320
caagcccctg ttgcgtcggc gggagggca tgctaatggg gttctttggg ggacaccggg 1380
ttggtccccc aaatcggggg ccgggccgtg catgctaatg atattctttg ggggcgccgg 1440
gttggtcccg gggacggggg ccgccccgcg gtgggcctgc ctcccctggg acgcgcggcc 1500
attgggggaa tcgtcactgc cgcccctttg gggagggaa  aggcgtgggg tataagttag 1560
ccctggcccg acggtctggt cgcatttgca cctcggcact cggagcgaga cgcagcagcc 1620
aggcagactc gggccgcccc ctctccgcat caccacagaa gccccgccta cgttgcgacc 1680
cccagggacc ctccgtcagc gaccctccag ccgcatacga cccccatgga gccccgcccc 1740
ggagcgagta cccgccggcc tgagggccgc cccagcgcg  aggtgagggg ccgggcgcca 1800
tgtctgggc  gccatgttgg ggggcgccat gttgggggc  gccatgttgg ggaccccg   1860
acccttacac tggaaccggc cgccatgttg gggaccccc  actcatacac gggagccggg 1920
cgccatgttg gggcgccatg ttaggggcg  tggaaccccg tgacactata tacagggga  1980
ccggggggcgc catgttaggg ggcgcggaac ccctgaccc  tatatataca gggaccgggg 2040
tcgccctgtt aggggtcgcc atgtgacccc ctgactttat atatacagac ccccaacacc 2100
tacacatggc ccctttgact cagacgcagg gcccggggtc gccgtgggac cccctgact  2160
catacacaga gacacgcccc cacaacaaac acacagggac cggggtcgcc gtgttagggg 2220
gcgtggtccc cactgactca tacgcaggc  cccttactc  acacgcatct aggggggtgg 2280
ggaggagccg cccgccatat ttgggggacg ccgtgggacc cccgactccg gtgcgtctgg 2340
```

| | |
|---|---|
| agggcgggag aagagggaag aagagggtc gggatccaaa ggacggaccc agaccacctt | 2400 |
| tggttgcaga ccccttctc ccccctcttc cgaggccagc agggggggcag gactttgtga | 2460 |
| ggcggggggg gaggggggaac tcgtgggcgc tgattgacgc gggaaatccc cccattctta | 2520 |
| cccgcccccc cttttttccc ctcagccgc cccggatgtc tgggtgtttc cctgcgaccg | 2580 |
| agacctgccg gacagcagcg actcggaggc ggagaccgaa gtgggggggc gggggggacgc | 2640 |
| cgaccaccat gacgacgact ccgcctccga ggcggacagc acggacacgg aactgttcga | 2700 |
| gacggggctg ctggggccgc agggcgtgga tggggggggcg gtctcggggg ggagccccccc | 2760 |
| ccgcgaggaa gaccccggca gttgcggggg cgccccccct cgagaggacg ggggagcga | 2820 |
| cgagggcgac gtgtgcgccg tgtgcacgga tgagatcgcg ccccacctgc gctgcgacac | 2880 |
| cttcccgtgc atgcaccgct tctgcatccc gtgcatgaaa acctggatgc aattgcgcaa | 2940 |
| cacctgcccg ctgtgcaacg ccaagctggt gtacctgata gtgggcgtga cgcccagcgg | 3000 |
| gtcgttcagc accatcccga tcgtgaacga ccccagacc cgcatggagg ccgaggaggc | 3060 |
| cgtcagggcg ggcacggccg tggactttat ctggacggga aatcagcggt tcgcccccgcg | 3120 |
| gtacctgacc ctgggggggc acacggtgag ggccctgtcg cccacccacc ctgagcccac | 3180 |
| cacggacgag gatgacgacg acctggacga cggtgaggcg ggggggcggc gaggaccctg | 3240 |
| ggggaggagg aggagggggg ggggagggag gaataggcgg gcgggcgggc gaggaaaggg | 3300 |
| cgggccgggg aggggcgta acctgatcgc gccccccgtt gtctcttgca gcagactacg | 3360 |
| taccgcccgc ccccgccgg acgccccgcg ccccccacg cagaggcgcc gccgcgcccc | 3420 |
| ccgtgacggg cggggcgtct cacgcagccc ccagccggc cgcggctcgg acagcgcccc | 3480 |
| cctcggcgcc catcgggcca cacggcagca gtaacactaa caccaccacc aacagcagcg | 3540 |
| gcggcggcgg ctcccgccag tcgcgagccg cggtgccgcg ggggcgtct ggcccctccg | 3600 |
| gggggttgg ggttgttgaa gcggaggcgg ggcggccgag gggccggacg ggccccttg | 3660 |
| tcaacagacc cgcccccctt gcaaacaaca gagacccat agtgatcagc gactcccccc | 3720 |
| cggcctctcc ccacaggccc cccgcggcgc ccatgccagg ctccgccccc cgccccggtc | 3780 |
| ccccccgcgtc cgcggccgcg tcgggccccg cgcgccccccg cgcggccgtg gccccgtgtg | 3840 |
| tgcgggcgcc gcctccgggg cccggccccc gcgcccggc ccccggggcg gagccggccg | 3900 |
| cccgccccgc ggacgcgcgc cgtgtgcccc agtcgcactc gtccctggct caggccgcga | 3960 |
| accaagaaca gagtctgtgc cgggcgcgtg cgacggtggc gcgcggctcg ggggggccgg | 4020 |
| gcgtggaggg tggacacggg ccctccccgcg gcgccgcccc ctccgcgcc gcccctccg | 4080 |
| gcgcccccc gctcccctcc gccgcctctg tcgagcagga ggcggcggtg cgtccgagga | 4140 |
| agaggcgcgg gtcgggccag gaaaacccct ccccccagtc cacgcgtccc ccctcgcgc | 4200 |
| cggcaggggc caagagggcg gcgacgcacc ccccctccga ctcagggccg ggggggcgcg | 4260 |
| gccaggagg gccgggacc cccctgacgt cctcggcggc ctccgcctct tcctcctccg | 4320 |
| cctcttcctc ctcggccccg actccgcgcg gggccacctc ttccgccacc ggggccgcgt | 4380 |
| cctcctccgc ttccgcctcc tcgggcgggg ccgtcggtgc cctgggaggg agacaagagg | 4440 |
| aaacctccct cggccccgc gctgcttctg ggccgcgggg gccgaggaag tgtgcccgga | 4500 |
| agacgcgcca cgcggagact tccggggccg tccccgcggg cggcctcacg cgctacctgc | 4560 |
| ccatctcggg ggtctctagc gtggtcgccc tgtcgcctta cgtgaacaag acgatcacgg | 4620 |
| gggactgcct gcccatcctg gacatggaga cggggaacat cggggcgtac gtggtcctgg | 4680 |
| tggaccagac gggaaacatg gcgacccggc tgcgggccgc ggtccccggc tggagccgcc | 4740 |

```
gcaccctgct ccccgagacc gcgggtaacc acgtgacgcc cccgagtac ccgacggccc    4800 ccgcgtcgga gtggaacagc ctctggatga ccccgtggg gaacatgctg ttcgaccagg    4860 gcacccctagt gggcgccctg gacttccgca gcctgcggtc tcggcacccg tggtccgggg  4920
agcagggggc                                                          4930
```

<210> SEQ ID NO 7
<211> LENGTH: 239
<212> TYPE: PRT
<213> ORGANISM: artificial
<220> FEATURE:
<223> OTHER INFORMATION: GFP

<400> SEQUENCE: 7

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 8
<211> LENGTH: 253
<212> TYPE: PRT
<213> ORGANISM: artificial
<220> FEATURE:
<223> OTHER INFORMATION: PD-1 scFv

<400> SEQUENCE: 8

```
Asp Val Leu Met Thr Gln Thr Pro Leu Phe Leu Pro Val Ser Leu Gly
1               5                   10                  15

Asp Gln Ala Ser Ile Phe Cys Arg Ser Ser Gln Asn Ile Val His Ile
            20                  25                  30
```

-continued

Asn Gly Asn Thr Tyr Leu Glu Trp Tyr Leu Gln Lys Pro Gly Gln Phe
         35                  40                  45

Pro Lys Leu Leu Met Tyr Lys Val Ser Asn Arg Phe Phe Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
             85                  90                  95

Ser His Val Pro Trp Thr Phe Gly Gly Gly Thr Lys Leu Glu Ile Lys
             100                 105                 110

Gly Gly Gly Gly Ser Gly Gly Gly Gly Ser Gly Gly Gly Gly Ser Gly
         115                 120                 125

Gly Gly Gly Ser Ser Asp Val Gln Val Gln Glu Ser Gly Pro Gly Leu
     130                 135                 140

Val Lys Pro Ser Gln Ser Leu Ser Leu Thr Cys Thr Val Thr Gly Ser
145                 150                 155                 160

Ser Ile Thr Ser Asp Phe Ala Trp Glu Trp Ile Arg Gln Phe Pro Gly
                 165                 170                 175

Asn Lys Leu Glu Cys Met Gly Tyr Ile Gly Tyr Ser Gly Gly Thr Ile
             180                 185                 190

Tyr Asn Pro Ser Leu Lys Ser Arg Ile Ser Ile Thr Arg Asp Thr Ser
         195                 200                 205

Lys Asn Gln Phe Phe Leu Gln Leu Asn Ser Val Thr Thr Glu Asp Thr
     210                 215                 220

Ala Thr Tyr Tyr Cys Ala Arg Trp His Gly Ser Ser His Trp Tyr Phe
225                 230                 235                 240

Asp Val Trp Gly Ala Gly Thr Thr Val Thr Val Ser Ser
                 245                 250

<210> SEQ ID NO 9
<211> LENGTH: 26
<212> TYPE: DNA
<213> ORGANISM: artificial
<220> FEATURE:
<223> OTHER INFORMATION: primer

<400> SEQUENCE: 9
gacgtgtgcg ccgtgtgcac ggatga                                        26

<210> SEQ ID NO 10
<211> LENGTH: 29
<212> TYPE: DNA
<213> ORGANISM: artificial
<220> FEATURE:
<223> OTHER INFORMATION: primer

<400> SEQUENCE: 10
actctgttct tggttcgcgg cctgagcca                                     29

<210> SEQ ID NO 11
<211> LENGTH: 21
<212> TYPE: DNA
<213> ORGANISM: artificial
<220> FEATURE:
<223> OTHER INFORMATION: primer

<400> SEQUENCE: 11
atggcccgcc gccgccatcg c                                             21

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
ttagaccgag ttcgccgggc                                               20

<210> SEQ ID NO 13
<211> LENGTH: 29
<212> TYPE: DNA
<213> ORGANISM: artificial
<220> FEATURE:
<223> OTHER INFORMATION: primer

<400> SEQUENCE: 13
atggcgactg acattgatat gctaattga                                     29

<210> SEQ ID NO 14
<211> LENGTH: 32
<212> TYPE: DNA
<213> ORGANISM: artificial
<220> FEATURE:
<223> OTHER INFORMATION: primer

<400> SEQUENCE: 14
ctaaaacagg gagttgcaat aaaaatattt gc                                 32

<210> SEQ ID NO 15
<211> LENGTH: 26
<212> TYPE: DNA
<213> ORGANISM: artificial
<220> FEATURE:
<223> OTHER INFORMATION: primer

<400> SEQUENCE: 15
ctcccagtgg attcgcgggc acagac                                        26

<210> SEQ ID NO 16
<211> LENGTH: 25
<212> TYPE: DNA
<213> ORGANISM: artificial
<220> FEATURE:
<223> OTHER INFORMATION: primer

<400> SEQUENCE: 16
ctgcctgaaa ctcgcgccgc gagga                                         25

<210> SEQ ID NO 17
<211> LENGTH: 1470
<212> TYPE: DNA
<213> ORGANISM: herpes simplex virus 1

<400> SEQUENCE: 17
ctactcgtcc cagaatttgg ccaggacgtc cttgtagaac gcgggtgggg gggcctgggt    60
ccgcagctgc tccagaaacc tgtcggcgat atcaggggcc gtgatatgcc gggtcacaat   120
agatcgcgcc aggttttcgt cgcggatgtc ctggtagata ggcaggcgtt tcagaagagt   180
ccacggcccc cgctccttgg ggccgataag cgatatgacg tacttaatgt agcggtgttc   240
caccagctcg gtgatggtca tgggatcggg gagccagtcc agggactctg ggcgtcgtg   300 gatgacgtgg cgtcgccggc tggccacata actgcggtgc tcttccagca gctgcgcgtt   360

```
cgggacctgg acgagctcgg gcggggtgag tatctccgag gaggacgacc tggggccggg      420 gtggccccg gtaacgtccc ggggatccag ggggaggtcc tcgtcgtctt cgtatccgcc       480
ggcgatctgt tgggttagaa tttcggtcca cgagacgcgc atctcggtgc cgccggcggc      540
cggcggcaaa gggggcctgg tttccgtgga gcgcgagctg tgtgttccc ggcggatggc       600 ccgccgggtc tgagagcgac tcggggggt ccagtgacat tcgcgcagca catcctccac       660
ggaggcgtag gtgttattgg gatggaggtc ggtgtgggca cggacaaaga gggccaggaa     720
ctgggggtag ctcatcttaa agtactttag tatatcgcga cagttgatcg tgggaatgta    780
gcaggcgcta atatccaaca caatatcaca gcccatcaac aggaggtcag tgtctgtggt    840
gtacacgtac gcgaccgtgt tggtgtgata gaggttggcg caggcatcgt ccgcctccag    900
ctgacccgag ttaatgtagg cgtaccccag ggcccggaga acgcgaatac agaacagatg    960
cgccagacgc agggccggct tcgagggcgc ggcggacggc agcgcggctc cggacccggc   1020
cgtcccccgg gtccccgagg ccagagaggt ccgcgccgg cgcatgttgg aaaaggcaga    1080
gctgggtctg gagtcggtga tgggggaagg cggtggagag gcgtccacgt cactggcctc   1140
ctcgtccgtc cggcattggg ccgtcgtgcg ggccaggatg gccttggctc caaacacaac   1200
cggctccata caattgaccc cgcgatcggt aacgaagatg gggaaaaggg acttttgggt   1260
aaacaccttt aataagcgac agaggcagtg tagcgtaatg gcctcgcggt cgtaactggg    1320
gtatcggcgc tgatatttga ccaccaacgt gtacatgacg ttccacaggt ccacggcgat    1380
gggggtgaag tacccggccg gggccccaag gccctggcgc ttgaccagat ggtgtgtgtg   1440
ggcaaacttc atcatcccga acaaacccat                                      1470

<210> SEQ ID NO 18
<211> LENGTH: 1248
<212> TYPE: DNA
<213> ORGANISM: herpes simplex virus 1

<400> SEQUENCE: 18
atgctccgca acgacagcca ccgggccgcg tccccggagg acggccaggg acgggtcgac      60
gacggacggc cacacctcgc gtgcgtgggg gccctggcgc gggggttcat gcatatctgg     120
cttcaggccg ccacgctggg ttttgcggga tcggtcgtta tgtcgcgcgg gccgtacgcg    180
aatgccgcgt ctggggcgtt cgccgtcggg tgcgccgtgc tgggctttat gcgcgcaccc     240
cctcccctcg cgcggcccac cgcgcggata tacgcctggc tcaaactggc ggccggtgga    300
gcggcccttg ttctgtggag tctcggggag cccggaacgc agccggggc cccggggcccg    360 gccacccagt gcctggcgct gggcgccgcc tatgcggcgc tcctggtgct cgccgatgac    420
gtctatccgc tctttctcct cgccccgggg cccctgttcg tcggcaccct ggggatggtc    480
gtcggcgggc tgacgatcgg aggcagcgcg cgctactggt ggatcggtgg gcccgccgcg     540
gccgccttgg ccgcggcggt gttggcgggc cggggggcga ccaccgccag ggactgcttc     600
tccagggcgt gccccgacca ccgccgcgtc tgcgtcatcg tcgcaggcga gtctgtttcc     660
cgccgccccc cggaggaccc agagcgaccc ggggacccccg gccaccgtc cccccgaca    720 ccccaacgat cccagggggcc gccggccgat gaggtcgcac cggccgggt agcgcggccc   780 gaaaacgtct gggtgcccgt ggtcaccttt ctggggggcgg gcgcgctcgc cgtcaagacg    840
gtgcgagaac atgcccggga aacgccgggc ccggcctgc cgctgtggcc ccaggtgttt     900
ctcggaggcc atgtggcggt ggccctgacg gagctgtgtc aggcgcttat gccctgggac    960
```

```
cttacggacc cgctgctgtt tgttcacgcc ggactgcagg tcatcaacct cgggttggtg   1020
tttcggtttt ccgaggttgt cgtgtatgcg gcgctagggg gtgccgtgtg gatttcgttg   1080
gcgcaggtgc tggggctccg gcgtcgcctg cacaggaagg accccgggga cggggcccgg   1140
ttggcggcga cgcttcgggg cctcttcttc tccgtgtacg cgctgggttt tggggtgggg   1200
gcgctgctgt gccctccggg gtcaacgggc gggtggtcgg gcgattga             1248
```

<210> SEQ ID NO 19
<211> LENGTH: 1473
<212> TYPE: DNA
<213> ORGANISM: herpes simplex virus 1

<400> SEQUENCE: 19

```
ctacccaccg tactcgtcaa ttccaagggc atcggtaaac atctgctcaa actcgaagtc     60
ggccatatcc agagcgccgt aggggggcgga gtcgtggggg gtaaatcccg gacccgggga   120
atccccgtcc cccaacatgt ccagatcgaa atcgtctagc gcgtcggcat gcgccatcgc   180
cacgtcctcg ccgtctaagt ggagctcgtc ccccaggctg acatcggtcg ggggggccgt   240
cgacagtctg cgcgtgtgtc ccgcggggag aaaggacagg cgcggagccg ccagccccgc   300
ctcttcgggg gcgtcgtcgt ccgggagatc gagcaggccc tcgatggtag accgtaatt   360 gttttcgta cgcgcgcggc tgtacgcgtg ttcccgcatg accgcctcgg agggcgaggt   420
cgtgaagctg gaatacgagt ccaacttcgc ccgaatcaac accataaagt acccagaggc   480
gcgggcctgg ttgccatgca gggtgggagg ggtcgtcaac ggcgcccctg gctcctccgt   540
agccgcgctg cgcaccagcg ggaggttaag gtgctcgcga atgtggttta gctcccgcag   600
ccggcgggcc tcgattggca ctccccggac ggtgagcgct ccgttgacga acatgaaggg   660
ctggaacaga cccgccaact gacgccagct ctccaggtcg caacagaggc agtcaaacag   720
gtcgggccgc atcatctgct cggcgtacgc ggcccatagg atctcgcggg tcaaaaatag   780
atacaaatgc aaaaacagaa cacgcgccag acgagcggtc tctcggtagt acctgtccgc   840
gatcgtggcg cgcagcattt ctcccaggtc gcgatcgcgt ccgcgcatgt gcgcctggcg   900
gtgcagctgc cggacgctgg cgcgcaggta ccggtacagg gccgagcaga agttggccaa   960
cacggttcga tagctctcct cccgcgcccg tagctcggcg tggaagaaac gagagagcgc  1020
ttcgtagtag agcccgaggc cgtcgcgggt ggccggaagc gtcgggaagg ccacgtcgcc  1080
gtgggcgcga atgtcgattt gggcgcgttc ggggacgtac gcgtccccccc attccaccac  1140 atcgctgggc agcgttgata ggaatttaca ctcccggtac aggtcggcgt tggtcggtaa  1200
cgccgaaaac aaatcctcgt tccaggtatc gagcatggta catagcgcgg ggcccgcgct  1260
aaagcccaag tcgtcgagga gacggttaaa gagggcggcg gggggacgg gcatgggcgg  1320 ggagggcatg agctgggcct ggctcaggcg ccccgttgcg tacagcggag gggccgccgg  1380 ggtgttttg gaccccggg ccgggcgggg ggtggtggc gaagcgccgt ccgcgtccat  1440
gtcggcaaac agctcgtcga ccaagaggtc cat                                1473
```

<210> SEQ ID NO 20
<211> LENGTH: 561
<212> TYPE: DNA
<213> ORGANISM: herpes simplex virus 1

<400> SEQUENCE: 20

```
atgacagcga cccccctcac caacctgttc ttacgggccc ggacataac ccacgtggcc     60 cccccttact gcctcaacgc cacctggcag gccgaaacgg ccatgcacac cagcaaaacg   120
```

```
gactccgctt gcgtggccgt gcggagttac ctggtccgcg cctcctgtga gaccagcggc    180
acaatccact gcttttcttt tgcggtatac aaggacaccc accataccccc tccgctgatt    240 accgagctcc gcaactttgc ggacctggtt aaccacccgc cggtcctacg cgaactggag    300
gataagcgcg gggtgcggct gcggtgtgcg cggccgttta gcgtcgggac gattaaggac    360
gtctctgggt ccggcgcgtc ctcggcggga gagtacacga taaacgggat cgtgtaccac    420
tgccactgtc ggtatccgtt ctcaaaaaca tgctggatgg gggcctccgc ggccctacag    480
cacctgcgct ccatcagctc agcggcatg gccgcccgcg cggcagagca tcgacgcgtc    540
aagattaaaa ttaaggcgtg a                                              561
```

<210> SEQ ID NO 21
<211> LENGTH: 876
<212> TYPE: DNA
<213> ORGANISM: herpes simplex virus 1

<400> SEQUENCE: 21

```
ctacagggtg gtaaccggat agcagatgtg aggaagtctg gccgttcgc cgcgaacggc     60 gatcagaggg tccgtttctt gcggaccacg gcccggtgat gtgggttgct cgtctaaaat    120
ctcgggcata cccatacacg cacaacacgg acgccgcacc gaatgggacg tcgtaagggg    180
gtgggaggta gctgggtggg gtttgtgcag agcaatcagg gaccgcagcc agcgcataca    240
atcgcgctcc cgtccgttgg tcccgggcag gaccacgccg tactggtatt cgtaccggct    300
gagcagggtc tccaggggt ggttgggtgc cgcggggaac ggggtccacg ccacggtcca    360
ctcgggcaaa aaccgagtcg gcacggccca cggttctccc acccacgcgt ctgggggtctt    420 gatggcgata aatcttaccc cgagccggat ttttggggcg tattcgagaa acggcacaca    480
cagatccgcc gcgcctacca cccacaagtg gtagaggcga ggggggctgg gttggtctcg    540
gtgcaacagt cggaagcacg ccacggcgtc cacgacctcg gtgctctcca aggggctgtc    600
ctccgcaaac aggcccgtgg tggtgtttgg ggggcagcga caggacctag tgcgcacgat    660
cgggcgggtg ggtttgggta agtccatcag cggctcggcc aaccgtcgaa ggttggccgg    720
gcgaacgacg accggggtac ccaggggttc tgatgccaaa atgcggcact gcctaagcag    780
gaagctccac agggccgggc ttgcgtcgac ggaagtccgg ggcagggcgt tgttctggtc    840
aaggagggtc attacgttga cgacaacaac gcccat                              876
```

<210> SEQ ID NO 22
<211> LENGTH: 2282
<212> TYPE: DNA
<213> ORGANISM: herpes simplex virus 1

<400> SEQUENCE: 22

```
cccgggaccc ccctgacgtc ctcggcggcc tccgcctctt cctcctccgc ctcttcctcc     60
tcggccccga ctcccgcggg ggccaccctct tccgccaccg gggccgcgtc ctcctccgct    120
tccgcctcct cgggcggggc cgtcggtgcc ctgggaggga gacaagagga aacctccctc    180 ggccccgcg ctgcttctgg gccgcggggg ccgaggaagt gtgccggaa gacgcgccac    240 gcggagactt ccggggccgt ccccgcgggc ggcctcacgc gctacctgcc catctcgggg    300
gtctctagcg tggtcgccct gtcgccttac gtgaacaaga cgatcacggg ggactgcctg    360
cccatcctgg acatggagac ggggaacatc ggggcgtacg tggtcctggt ggaccagacg    420
ggaaacatgg cgacccggct gcgggccgcg gtccccggct ggagccgccg caccctgctc    480
```

```
cccgagaccg cgggtaaccca cgtgacgccc cccgagtacc cgacggcccc cgcgtcggag      540
tggaacagcc tctggatgac ccccgtgggg aacatgctgt tcgaccaggg caccctagtg      600
ggcgccctgg acttccgcag cctgcggtct cggcacccgt ggtcggggga gcaggggggcg     660 tcgacccggg acgagggaaa acaataaggg acgccccgt gtttgtgggg aggggggggt      720
cgggcgctgg gtggtctctg gccgcgccca ctacaccagc caatccgtgt cggggaggtg      780
gaaagtgaaa gacacgggca ccacacacca gcgggtcttt tgtgttggcc ctaataaaaa      840
aaactcaggg gatttttgct gtctgttggg aaataaaggt ttacttttgt atcttttccc      900
tgtctgtgtt ggatgtatcg cggggggtgcg tgggagtggg ggtgcgtggg agtgggggtg    960
cgtgggagtg ggggtgcgtg ggagtggggg tgcgtgggag tggggggtgcg tgggagtggg   1020 ggtgcgtggg agtgggggtg cgtgggagtg ggggtgcgtg ggagtggggg tgccatgttg    1080
ggcaggctct ggtgttaacc acagagccgc ggcccgggct gcctgaccac cgatccccga    1140
aagcatcctg ccactggcat ggagccagaa ccacagtggg ttgggtgtgg gtgttaagtt    1200
tccgcgagcg cctgcccgcc cggactgacc tggcctctgg ccgccacaaa gggcgggggg    1260
gggggttaac tacactatag ggcaacaaag gatgggaggg gtagcggggc gggacggggc    1320
gcccaaaagg gggtcggcca caccacagac gtgggtgttg gggggtgggg cggaggggtg    1380 ggggggggaga cagaaacagg aacatagtta gaaaacaaga atgcggtgca gccagagaat  1440
cacaggagac gaggggatgg gcgtgttggt taccaaccca cacccaggca tgctcggtgg   1500
tatgaaggag ggggggcggt gtttcttaga gaccgccggg ggacgtgggg ttggtgtgca  1560
aaggcacgcg caccccgcgcc ggccaggtgg gccggtaccc catccccccc tcccccgacc  1620
cttcccaccc ccgcgtgcca gagatcaccc cggtcccccg gcacccgcca ctcctccata   1680
tcctcgcttt aggaacaact ttaggggggg gtacacacgc gccgtgcatt tccttccaca   1740 cccccccct ccccgcact cccccccccc aggcagtaag acccaagcat agagagccag      1800
gcacaaaaac acaggcgggg tgggacacat gccttcttgg agtacgtggg tcattggcgt    1860 gggggggttac agcgacaccg gccgaccccc tggcggtctt ccagccggcc cttagataag   1920
ggggcagttg gtggtcggac gggtaagtaa cagagtctaa ctaagggtgg gagggggggga  1980 aaataacggg ctggtgtgct gtaacacgag cccacccgcg agtggcgtgg ccgaccttag    2040
cctctggggc gccccctgtc gtttgggtcc ccccccctct attggggaga agcaggtgtc    2100
taacctacct ggaaacgcgg cgtctttgtt gaacgacacc ggggcgccct cgacgagtgg    2160
gataacgggg gaggaaggga gggaggaggg tactgggggt gaaggggggg ggggagaagc    2220
gagaacagga aaggcgacgg agcccggcag aacaccgagg aaaaaaaaac cacagcgcat    2280
gc                                                                   2282

<210> SEQ ID NO 23
<211> LENGTH: 1633
<212> TYPE: DNA
<213> ORGANISM: herpes simplex virus 1

<400> SEQUENCE: 23
ccatgttggg caggctctgg tgttaaccac agagccgcgg cccgggctgc ctgaccaccg       60
atccccgaaa gcatcctgcc actggcatgg agccagaacc acagtgggtt gggtgtgggt      120
gttaagtttc cgcgagcgcc tgcccgcccg gactgacctg gcctctggcc gccacaaagg      180 gcggggggg gggttaacta cactataggg caacaaagga tggagggggt agcggggcgg      240
gacggggcgc ccaaaagggg gtcggccaca ccacagacgt gggtgttggg gggtggggcg      300
```

```
gaggggtggg gggggagaca gaaacaggaa catagttaga aaacaagaat gcggtgcagc    360
cagagaatca caggagacga ggggatgggc gtgttggtta ccaacccaca cccaggcatg    420
ctcggtggta tgaaggaggg ggggcggtgt ttcttagaga ccgccggggg acgtggggtt    480
ggtgtgcaaa ggcacgcgca cccgcgccgg ccaggtgggc cggtacccca tccccccctc    540
ccccgaccct tcccacccce gcgtgccaga gatcaccccg gtccccggc acccgccact    600
cctccatatc ctcgctttag gaacaacttt aggggggggt acacacgcgc cgtgcatttc    660
cttccacacc cccccctcc cccgcactcc ccccccag gcagtaagac ccaagcatag    720
agagccaggc acaaaaacac aggcggggtg ggacacatgc cttcttggag tacgtgggtc    780
attggcgtgg ggggttacag cgacaccggc cgaccccctg gcggtcttcc agccggccct    840
tagataaggg ggcagttggt ggtcggacgg gtaagtaaca gagtctaact aagggtggga    900
gggggggaaa ataacgggct ggtgtgctgt aacacgagcc cacccgcgag tggcgtggcc    960
gaccttagcc tctgggggcgc cccctgtcgt ttgggtcccc cccctctat tggggagaag   1020
caggtgtcta acctacctgg aaacgcggcg tctttgttga acgacaccgg ggcgccctcg   1080
acgagtggga taacggggga ggaagggagg gaggagggta ctgggggtga aggggggggg   1140
ggagaagcga gaacaggaaa ggcgacggag cccggcagaa caccgaggaa aaaaaaacca   1200
cagcgcatgc gccgggccgt tgtgggggccc cgggccgggg cccccttgggt ccgccggggc   1260
cccgggccgg gccgccacgg gggccggccg ttggcggtaa ccccgagtgt tcatctcagg   1320
ccccgggccg ggaacccgga aaagcctccg gggggccttt ttcgcgtcgc gtgccggcga   1380
gcgggtccgg acggggcccg gaccgccgcg gtcggggggcc cctcgtcccg ggccgtacgc   1440
ggccttcgcc ccgtgagggg acagacgaac gaaacattcc ggcgacggaa cgaaaaacac   1500
cccagacggg ttaaagaaac agaaaccgca acccccacca ccccgaaac ggggaaaacg   1560
aaaaaacaga ccagcggccg gccggcgctt agggggagga tgtcgccgac gcccttggc   1620
cgccccggct gca                                                      1633
```

RECOMBINANT HERPES SIMPLEX VIRUS AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 980127_401USPC_SEQUENCE_LISTING.txt. The text file is 40.3 KB, was created on Sep. 5, 2019, and is being submitted electronically via EFS-Web.

TECHNICAL FIELD

The invention relates to the field of virology and tumor therapy. In particular, the present invention provides a recombinant herpes simplex virus (HSV) which is capable of specifically replicating at a high level in a tumor cell and effectively killing the tumor cell, but replicating at a low level in a normal cell, so that the recombinant herpes simplex virus of the present invention not only has a high lethality against a tumor cell, but also has a significant decrease in side effects (especially neurotoxicity). Further, the present invention relates to a viral vector constructed based on the recombinant herpes simplex virus, a pharmaceutical composition comprising the recombinant herpes simplex virus or the viral vector, and a use of the recombinant herpes simplex virus or the viral vector. The recombinant herpes simplex virus of the present invention can be used to infect and kill a tumor cell, and can be used for delivering a gene drug into a tumor cell for gene therapy.

BACKGROUND ART

Radiotherapy, chemotherapy and targeted drugs are currently widely used tumor treatment regimens, but they all have many problems such as incomplete treatment, large side effects, prone to drug resistance, unable to control tumor recurrence and metastasis, and unsatisfactory in tumor treatment effects. Therefore, there is an urgent need to develop new and effective tumor treatment methods. In recent years, significant improvement in people's understanding of the relationship between tumor and immunity has been achieved, and immunotherapy of tumors has developed rapidly. Among them, oncolytic virus (OV) therapy has attracted attention as a new type of tumor immunotherapy (Lichty B D, Breitbach C J, Stojdl D F, et al. Going viral with cancer immunotherapy [J]. Nat Rev Cancer, 2014, 14 (8): 559-567). Oncolytic viruses are a class of viruses with tumorphilic properties that are capable of selectively replicating in tumor cells, while their proliferation in normal cells is limited. Oncolytic viruses can replicate in tumor cells leading to tumor cell lysis and death, and the amplified virus can continue to infect surrounding tumor cells, creating a cascade effect. In addition, during the process of lysing tumor cells, the oncolytic viruses can also release tumor antigens, stimulating the body to produce anti-tumor antibodies with specific anti-tumor immunity, and further enhancing the oncolytic effect of the oncolytic viruses. Oncolytic viruses are the most popular novel gene therapy drugs in the field of malignant tumor treatment. Especially in the local control treatment of solid tumors, the infection and proliferation of oncolytic virus leads to tumor ablation at the injection site, and the lysis of tumor cells leads to the release of tumor antigens from tumor cells, thereby inducing systemic anti-tumor immune response to fight tumors in other areas in the body, which may be a key immune response for the systemic control of tumor spread and metastasis (Russell S J, Peng K W, Bell J C. Oncolytic virotherapy [J]. Nat Biotechnol, 2012, 30 (7): 658-670).

The current oncolytic viruses can be divided into more than ten kinds according to the type of virus. Among them, the oncolytic herpes simplex virus type I (HSV-1) has become the first choice for genetic engineering tumor treatment drugs at home and abroad, because the used virus vector has large gene-carring capacity, short replication cycle, high infection efficiency, ability of inserting multiple therapeutic genes and other advantages.

HSV-1 virus belongs to herpesvirus family and is a type of enveloped DNA virus that causes herpes on lips, eyes and facial skin in human beings. According to epidemiological studies, more than 60% of the population have been infected with HSV-1 virus. The genome of HSV-1 virus consists of double-stranded linear DNA of 152 kb, which comprises two fragments ligated to each other: long and short fragments (Macdonald S J, Mostafa H H, Morrison L A, et al. Genome sequence of herpes simplex virus 1 strain KOS [J]. J Virol, 2012, 86 (11): 6371-6372). The long fragment (L region) accounts for about 82% of the genome, while the short fragment (S region) accounts for about 18% of the genome, and the long and short fragments are ligated together by a junction region. The L region comprises a pair of inverted repeat segments, the segment therebetween is referred to as a unique segment $U_L$; the S region also has a pair of inverted repeat segments, and the segment therebetween is referred to as a unique segment $U_S$. At present, the whole genome sequencing of the HSV-1 KOS strain has been completed. The genome of the KOS strain comprises a total of 152011 nucleotide bases, and comprises a total of 72 genes encoding proteins, wherein the unique segment $U_L$ comprises 56 genes, the unique segment $U_S$ comprises 12 genes, and the $U_L$ terminal inverted repeat segment ($TR_L$) and the $U_L$ intermediate inverted repeat sequence ($IR_L$) each comprises three identical genes (ICP34.5, ICP0, and LAT, respectively), the $U_S$ terminal inverted repeat segment ($TR_S$) and the $U_S$ intermediate inverted repeat sequence ($IR_S$) each comprises one identical gene (ICP4).

When HSV-1 is abundantly replicated, HSV-1 synthesizes proteins in a cascade-regulating manner at transcriptional level. These proteins can be classified into three types: α, β and γ according to the time order of their synthesis. HSV-1 virus first transcribes α-type genes that encode five immediate-early proteins (IE proteins), including ICP0, ICP4, ICP22, ICP27 and ICP47, which in turn activate β and γ type genes at transcriptional level, and promote the expression of early (E) and late (L) proteins of the virus. Immediate-early protein ICP0 can independently activate all types of viral genes (i.e., IE, E and L) as well as a variety of cellular genes (in some cases, synergistic activation of ICP4 may be required). ICP0 not only interacts with multiple intracellular transcription factors or regulatory proteins and activates transcription of certain genes in host cell; but also regulates viral genome expression and viral gene transcription through its ubiquitin ligase E3 functional domain (Kawaguchi Y, Bruni R, Roizman B. Interaction of herpes simplex virus 1 alpha regulatory protein ICP0 with elongation factor 1delta: ICP0 affects translational machinery [J]. J Virol, 1997, 71 (2): 1019-1024). ICP4 and ICP27 are the immediate early proteins necessary for viral replication (DeLuca N A, McCarthy A M, Schaffer P A. Isolation and characterization of deletion mutants of herpes simplex virus type 1 in the gene encoding immediate-early regulatory protein ICP4 [J]. J Virol, 1985, 56 (2): 558-570; Sacks W R, Greene C C, Aschman D P, et al. Herpes simplex virus type 1 ICP27 is an essential regulatory protein [J]. J Virol, 1985, 55 (3): 796-805). ICP27 is a multifunctional regulatory protein that promotes transcription of viral genes by interacting with RNA polymerase II. ICP27 is able to interact with ICP4 to activate early and late gene expression. ICP27 also indirectly promotes viral DNA replication by upregulating viral replication-associated genes. In addition, ICP27 also has the function of inhibiting cellular primordial RNA splicing and promoting viral mRNA translocation and translation. ICP34.5 can reverse the action of antiviral protein PKR, allowing host and viral protein synthesis to continue, thereby facilitating viral replication. In addition, ICP34.5 can also evade the host's antiviral response by regulating PP1 phosphatase activity (Randall G, Roizman B. Transcription of the derepressed open reading frame P of herpes simplex virus 1 precludes the expression of the antisense gamma (1) 34.5 gene and may account for the attenuation of the mutant virus [J]. J Virol, 1997, 71 (10): 7750-7757).

To date, a variety of oncolytic HSV-1 viral vectors have been in the preclinical or clinical research phase, including HSV1716, which was obtained by knockout of ICP34.5 gene in R3616 mutant strain (derived from HSV-1 F strain) (MacKie R M, Stewart B, Brown S M. Intralesional injection of herpes simplex virus 1716 in metastatic melanoma [J]. Lancet, 2001, 357(9255): 525-526; and Papanastassiou V, Rampling R, Fraser M, et al. The potential for efficacy of the modified (ICP 34.5(−)) herpes simplex virus HSV1716 following intratumoural injection into human malignant glioma: a proof of principle study [J]. Gene Ther, 2002, 9(6): 398-406); G207, which was obtained by double knockout of ICP34.5/ICP6 genes in R3616 mutant strain (Markert J M, Medlock M D, Rabkin S D, et al. Conditionally replicating herpes simplex virus mutant, G207 for the treatment of malignant glioma: results of phase I trial [J]. Gene Ther, 2000, 7(10): 867-874; and Markert J M, Razdan S N, Kuo H C, et al. A phase 1 trial of oncolytic HSV-1, G207, given in combination with radiation for recurrent GBM demonstrates safety and radiographic response [J]. Mol Ther, 2014, 22(5): 1048-1055); NV1020, which was obtained by deleting a single copy of ICP34.5/ICP0/ICP4/UL56 gene in R7020 mutant strain (derived from HSV-1 F strain) (Gutermann A, Mayer E, von Dehn-Rothfelser K, et al. Efficacy of oncolytic herpesvirus NV1020 can be enhanced by combination with chemotherapeutics in colon carcinoma cells [J]. Hum Gene Ther, 2006, 17(12): 1241-1253; and Geevarghese S K, Geller D A, de Haan H A, et al. Phase I/II study of oncolytic herpes simplex virus NV1020 in patients with extensively pretreated refractory colorectal cancer metastatic to the liver [J]. Hum Gene Ther, 2010, 21(9): 1119-1128); and T-VEC, which was obtained by double knockout of ICP34.5/ICP47 gene in the clinical HSV-1 isolate JS1 (Liu B L, Robinson M, Han Z Q, et al. ICP34.5 deleted herpes simplex virus with enhanced oncolytic, immune stimulating, and anti-tumour properties [J]. Gene Ther, 2003, 10(4): 292-303). In Amgen Company, USA, the recombinant HSV-1 virus T-VEC has made a breakthrough in the phase III clinical trial of patients with advanced melanoma, becoming the first oncolytic virus type therapeutic drug approved by FDA. However, the data suggest that this clinical trial only reached a primary endpoint of duration response rate (DRR) but did not reach a secondary endpoint of improved overall survival (OS), although the T-VEC treatment group showed a strong favorable trend (Andtbacka R H, Kaufman H L, Collichio F, et al. Talimogene Laherparepvec Improves Durable Response Rate in Patients With Advanced Melanoma [J]. J Clin Oncol, 2015, 33(25): 2780-2788). This is mainly because T-VEC has strong toxic side effects, and its initial intratumoral therapeutic dose is only $10^6$ PFU virus, which result in the significant decrease of tumor treatment effect and leads the patients to miss the best time for oncolytic treatment.

Although the oncolytic therapy of herpes simplex virus type I has achieved certain results in recent years, the analysis of recombinant HSV-1 virus that has entered the clinical study of cancer treatment shows that because different oncolytic viruses have different genetic modifications, different oncolytic effects and safety properties, their tumor indications and tumor treatment effects are different (Eager R M, Nemunaitis J. Clinical development directions in oncolytic virus therapy [J]. Cancer Gene Ther, 2011, 18(5): 305-317). In general, the existing oncolytic viruses have significant toxic and side effects, poor safety, and limited therapeutic dose of oncolytic virus, which pose severe challenges for tumor treatment researches (Liu T C, Galanis E, Kim D. Clinical trial results with oncolytic virotherapy: a century of promise, a decade of progress [J]. Nat Clin Pract Oncol, 2007, 4(2): 101-117). The therapeutic effect of oncolytic virus is positively correlated with the dose of virus administered. If the specificity and safety of oncolytic virus are not high enough, the necessary dose of the oncolytic virus may have to be limited so as to avoid serious side effects to the body. This seriously affects the clinical treatment effect of the oncolytic virus and leads to certain safety hazards. Taking T-VEC of Amgen in the United States as an example, the toxicity/side effects thereof are important factors limiting the clinical effects of T-VEC. Although scientists have been experimenting with it, no oncolytic virus has been found so far that can replicate at high levels in tumor cells and kill tumor cells without causing serious side effects on normal cells. Therefore, there is still a need to develop new oncolytic viruses to achieve low toxicity and high effectiveness of oncolytic virus therapy.

In order to overcome the above-mentioned drawbacks of the recombinant herpes simplex virus in gene therapy of tumors in the prior art, the inventors of the present application constructed a novel recombinant herpes simplex virus which can not only replicate at a high level in a tumor cell and exhibit a high lethality on the tumor cell, but also has a significantly reduced side effect (especially neurotoxicity). Therefore, the recombinant herpes simplex virus of the present invention not only maintains a high therapeutic effect of oncolytic virus, but also greatly improves the safety of the oncolytic virus.

Contents of the Invention

In the present invention, the scientific and technical terms used herein have the meanings commonly understood by those skilled in the art, unless otherwise stated. Moreover, the cell culture, molecular genetics, nucleic acid chemistry, and immunology laboratory procedures used herein are all routine steps widely used in the corresponding arts. Also, for a better understanding of the present invention, definitions and explanations of related terms are provided below.

As used herein, the term "recombinant HSV virus" refers to an engineered HSV virus comprising an artificially introduced mutation as compared to a wild-type HSV virus. It should be understood that the recombinant HSV virus of the present invention is not limited to its production manner. For example, the recombinant HSV virus of the present invention can be produced by homologous recombination or by culturing a host cell infected with the recombinant HSV virus.

As used herein, the term "viral vector" refers to a nucleic acid delivery vehicle that is constructed based on the viral genome and is capable of carrying an exogenous nucleotide sequence. In general, the viral vector is capable of self-replicating and/or expressing the genes (endogenous and exogenous) comprised therein in a suitable host cell. The viral vector may comprise a genome of an intact wild type virus, or a viral genome that has been mutated or modified. However, for safety reasons, the viral vector generally preferably comprises a mutated or modified viral genome. Since the viral vector of the present invention is derived from the viral genome of HSV, the viral vector of the present invention may also be referred to as an HSV viral vector.

As used herein, the expression "does/do not express a functional protein of interest" means that when a cell is infected with a virus or viral vector or viral genome, the virus or viral vector or viral genome is unable to produce or express an protein of interest with biologically functional activity. For example, the virus or viral vector or viral genome may not produce or express the protein of interest at all due to a gene deletion, or may produce or express a protein of interest without the biologically functional activity due to a loss-of-function mutation.

As used herein, the term "loss-of-function mutation" refers to a mutation that results in the loss of biologically functional activity of a protein encoded and expressed by the mutated gene. Loss-of-function mutation includes, but is not limited to, missense mutation, nonsense mutation, frameshift mutation, base deletion, base substitution, base addition, and any combination thereof (e.g., deletion or substitution or addition of a gene fragment), as long as the gene comprising the loss-of-function mutation cannot produce or express a protein having the biologically functional activity.

As used herein, the term "essential gene" refers to a gene that is essential for maintaining the survival and replication of an HSV virus. Specific examples of such essential genes include, but are not limited to, ICP27 gene (see, e.g., GenBank No. AFE62883.1), ICP4 gene (see, e.g., GenBank No. AFE62888.1), VP5 gene (see, e.g., GenBank No. AFE62846.1), gL gene (see, e.g., GenBank No. AFE62828.1), gH gene (see, e.g., GenBank No. AFE62849.1), gD gene (see, e.g., GenBank No. AFE62894.1), gK gene (see, e.g., GenBank No. AFE62882.1), gB gene (see, e.g., GenBank No. AFE62855.1), gN gene (see, e.g., GenBank No. AFE62878.1), UL5 gene (see, e.g., GenBank No. AFE62832.1), UL6 gene (see, e.g., GenBank No. AFE62833.1), UL8 gene (see, e.g., GenBank No. AFE62835.1), UL9 gene (see eg GenBank No. AFE62836.1), UL12 gene (see, e.g., GenBank No. AFE62839.1), UL25 gene (see, e.g., GenBank No. AFE62852.1), UL26 gene (see, e.g., GenBank No. AFE62853.1), UL28 gene (see, e.g., GenBank No. AFE62856.1), UL29 gene (see, e.g., GenBank No. AFE62857.1), UL30 gene (see, e.g., GenBank No. AFE62858.1), UL33 gene (see, e.g., GenBank No. AFE62861.1), UL36 gene (see, e.g., GenBank No. AFE62864.1), UL38 gene (see, e.g., GenBank No. AFE62866.1), UL42 gene (see, e.g., GenBank No. AFE62870.1), UL48 gene (see, e.g., GenBank No. AFE62876.1), UL52 gene (see, e.g., GenBank No. AFE62881.1). For a detailed description of the essential genes for the HSV virus, see, for example, Roizman B, Knipe D M. Herpes simplex viruses and their replication. In: Knipe D M, Howley P M, editors. Fields Virology. $2^{nd}$ ed. Vol 2. Philadelphia, Pa. Lippincot, Williams and Wilkins, 2001: 2399-2460; Subak-Sharpe J H, Dargan D J. HSV molecular biology: general aspects of herpes simplex virus molecular biology. Virus Genes, 1998, 16(3): 239-251.

As used herein, the term "non-essential gene" refers to a gene that is not required to maintain the survival and replication of an HSV virus. In general, such genes in the HSV viral genome can be knocked out (deleted) or mutated without affecting the survival and replication ability of the HSV virus. Specific examples of such essential genes include, but are not limited to, UL3 gene (see, e.g., GenBank No. AFE62830.1), UL4 gene (see, e.g., GenBank No. AFE62831.1), UL14 gene (see, e.g., GenBank No. AFE62841.1), UL16 gene (see, e.g., GenBank No. AFE62843.1), UL21 gene (see, e.g., GenBank No. AFE62848.1), UL24 gene (see, e.g., GenBank No. AFE62851.1), UL31 gene (see, e.g., GenBank No. AFE62859. 1), UL32 gene (see, e.g., GenBank No. AFE62860.1), US3 gene (see, e.g., GenBank No. AFE62891.1), UL51 gene (see, e.g., GenBank No. AFE62880.1), UL55 gene (see, e.g., GenBank No. AFE62884.1), UL56 gene (see, e.g., GenBank No. AFE62885.1), US2 gene (see, e.g., GenBank No. AFE62890.1), US12 gene (see, e.g., GenBank No. AFE62901.1; i.e., ICP47 gene), and LAT gene (see, e.g., GenBank No. JQ673480.1). For a detailed description of the non-essential genes of the HSV virus, see, for example, Roizman B, Knipe D M. Herpes simplex viruses and their replication. In: Knipe D M, Howley P M, editors. Fields Virology. $2^{nd}$ ed. Vol 2. Philadelphia, Pa.: Lippincot, Williams and Wilkins, 2001: 2399-2460; Subak-Sharpe J H, Dargan D J. HSV molecular biology: general aspects of herpes simplex virus molecular biology. Virus Genes, 1998, 16(3): 239-251.

As used herein, the term "ICP0 protein" refers to an infected cell protein 0 of an HSV virus, which is encoded by the RL2 gene and is one of the immediate early gene products of the HSV virus. The amino acid sequence of the ICP0 protein is known and can be seen, for example, in the public database NCBI (AFE62827.1).

As used herein, the term "ICP34.5 protein" refers to an infected cell protein 34.5 of an HSV virus, which is encoded by the RL1 gene and is one of the immediate early gene products of the HSV virus. The amino acid sequence of the ICP34.5 protein is known and can be seen, for example, in the public database NCBI (AFE62826.1).

As used herein, the term "ICP27 protein" refers to an infected cell protein 27 of an HSV virus, which is encoded by the UL54 gene. The amino acid sequence of the ICP27 protein is known and can be seen, for example, in the public database NCBI (AFE 62883.1).

As used herein, the term "ICP4 protein" refers to an infected cell protein 4 of an HSV virus, which is encoded by the RS1 gene. The amino acid sequence of the ICP4 protein is known and can be seen, for example, in the public database NCBI (AFE62888.1).

As used herein, the term "VP5 protein" refers to a major capsid protein of an HSV virus, which is encoded by the UL19 gene. The amino acid sequence of the VP5 protein is known and can be seen, for example, in the public database NCBI (AFE62846.1).

As used herein, the term "ICP0 gene" refers to a nucleotide sequence encoding an ICP0 protein in an HSV viral genome. As used herein, the term "ICP34.5 gene" refers to a nucleotide sequence encoding an ICP34.5 protein in an HSV viral genome. As used herein, the term "ICP27 gene"

refers to a nucleotide sequence encoding an ICP27 protein in an HSV viral genome. As used herein, the term "ICP4 gene" refers to a nucleotide sequence encoding an ICP4 protein in an HSV viral genome. As used herein, the term "VP5 gene" refers to a nucleotide sequence encoding a VP5 protein in an HSV viral genome.

As used herein, the term "exogenous nucleotide sequence" refers to an artificially introduced nucleotide sequence that is foreign to an original sequence. Exogenous nucleotide sequences include, but are not limited to, any gene not found in the viral genome. However, in certain instances, preferably, the exogenous nucleotide sequence encodes a polypeptide having therapeutic use, such as an immunomodulatory polypeptide, a cytokine, a chemokine, an antibody, and a cytotoxic peptide.

As used herein, the term "immunomodulatory polypeptide" refers to a polypeptide that modulates a function of an immune cell, examples of which include, but are not limited to, CD40L, OX40L, inducible costimulatory molecules (ICOS), FTL3L, LIGHT, CD137L, CD70, 4-1BB, GITR, and CD28 (see, for example, Khalil D N, Smith E L, Brentj ens R J, et al. The future of cancer treatment: immunomodulation, CARs and combination immunotherapy [J]. Nat Rev Clin Oncol, 2016, 13 (5): 273-290).

As used herein, the term "cytokine" has the meanings well known to those skilled in the art. However, in the method of the present invention, when the recombinant virus of the present invention is used to treat a tumor, it is particularly preferred that the cytokine is a cytokine which can be used for tumor treatment. Examples of "cytokine" include, but are not limited to, interleukins (e.g., IL-2, IL-12, and IL-15), interferons (e.g., IFNα, IFNβ, IFNγ), tumor necrosis factors (e.g., TNFα), colony stimulating factors (e.g., GM-CSF), and any combination thereof (see, for example, Ardolino M, Hsu J, Raulet D H. Cytokine treatment in cancer immunotherapy [J]. Oncotarget, 2015, 6 (23): 19346-19347).

As used herein, the term "chemokine" has the meanings well known to those skilled in the art. However, in the method of the present invention, when the recombinant virus of the present invention is used to treat a tumor, it is particularly preferred that the cytokine is a chemokine capable of being used for tumor treatment. Examples of "chemokine" include, but are not limited to, CCL2, RANTES, CCL7, CCL9, CCL10, CCL12, CCL15, CCL19, CCL21, CCL20, XCL-1, and any combination thereof (Homey B, Muller A, Zlotnik A. CHEMOKINES: AGENTS FOR THE IMMUNOTHERAPY OF CANCER? [J]. Nat Rev Immunol, 2002, 2: 175-184).

As used herein, the term "cytotoxic peptide" refers to a polypeptide that is toxic to a cell or induces apoptosis, examples of which include, but are not limited to, thymidine kinase TK (TK/GCV), TRAIL and FasL (see, e.g., Candolfi M, King G D, Muhammad A G, et al. Evaluation of proapototic transgenes to use in combination with Flt3L in an immune-stimulatory gene therapy approach for Glioblastoma multiforme (GBM) [J]. FASEB J, 2008, 22: 1077.13).

The term "antibody" as used herein has the meanings well known to those skilled in the art. However, in the method of the present invention, when the recombinant virus of the present invention is used to treat a tumor, it is particularly preferable that the antibody is an antibody which can be used for tumor treatment. Examples of "antibody" include, but are not limited to, anti-PD-1 antibodies, anti-PD-L1 antibodies, anti-TIGIT antibodies, anti-BTLA antibodies, anti-CTLA-4 antibodies, anti-Tim-3 antibodies, anti-Lag-3 antibodies, anti-CD137 antibodies, anti-OX40 antibodies, anti-GITR antibodies, anti-CD73 antibodies, anti-KIR antibodies, anti-ICOS antibodies, anti-CSF1R antibodies, anti-EGFR antibodies, anti-VEGFR antibodies, anti-HER2 antibodies and anti-PDGFR antibodies (see, e.g., Khalil D N, Smith E L, Brentjens R J, et al. The future of cancer treatment: immunomodulation, CARs and combination immunotherapy [J]. Nat Rev Clin Oncol, 2016, 13 (5): 273-290; and Hughes P E, Caenepeel S, Wu L C. Targeted Therapy and Checkpoint Immunotherapy Combinations for the Treatment of Cancer [J]. Trends Immunol, 2016, 37 (7): 462-476).

The term "pharmaceutically acceptable carrier and/or excipient" as used herein refers to a carrier and/or excipient that is pharmacologically and/or physiologically compatible with a subject and an active ingredient, which is well known in the art (see, for example, Remington's Pharmaceutical Sciences. Edited by Gennaro A R, 19th ed. Pennsylvania: Mack Publishing Company, 1995), and includes, but is not limited to, pH adjusting agents, surfactants, adjuvants, ionic strength enhancers. For example, pH adjusting agents include, but are not limited to, phosphate buffers; surfactants include, but are not limited to, cationic, anionic or nonionic surfactants, such as Tween-80; adjuvants include, but are not limited to, aluminum adjuvants (e.g., aluminum hydroxides), Freund's adjuvant (e.g., complete Freund's adjuvant); ionic strength enhancers include, but are not limited to, sodium chloride.

As used herein, the term "effective amount" refers to an amount sufficient to achieve, or at least partially achieve, a desired effect. For example, a prophylactically effective amount refers to an amount sufficient to prevent, control, or delay an onset of a disease; a therapeutically effective amount for a disease refers to an amount sufficient to cure or at least partially control the disease and complications thereof in a patient already suffering from the disease. Determination of such effective amounts is well within the capabilities of those skilled in the art. For example, the amount effective for therapeutic use depends on the severity of a disease to be treated, the overall condition of patient's own immune system, the general condition of patient such as age, weight and gender, the mode of administration of drug, other treatments simultaneously applied, and so on.

In order to overcome the safety issues and side effects of existing recombinant HSV viruses for tumor therapy, the inventors of the present application constructed a novel recombinant HSV virus that does not express functional ICP0 and ICP34.5 proteins (e.g., double copy of ICP0 and ICP34.5 genes were deleted). The recombinant HSV virus of the present invention has a high level of replication ability in a tumor cell and is capable of effectively killing various tumor cells, but shows significantly reduced replication ability and killing ability in a normal cell. Furthermore, it has also been discovered that the recombinant HSV virus of the invention shows significantly reduced neurotoxicity in an animal and can be administered to an animal at a significantly increased dose. Therefore, as compared with the existing recombinant HSV viruses, the recombinant HSV virus of the present invention not only maintains high oncolytic ability, but also shows significantly improved safety, therefore can be administered at a higher dose and has broad application prospects.

Recombinant HSV Virus

Thus, in one aspect, the invention provides a recombinant HSV virus, which does not express a functional ICP0 protein and ICP34.5 protein.

As well known to those skilled in the art, the functional expression of a protein of interest (e.g., ICP0 protein and/or ICP34.5 protein) can be prevented by modifying a gene encoding the protein of interest. For example, a loss-of-function mutation may be introduced into a gene encoding a protein of interest (e.g., ICP0 protein and/or ICP34.5 protein), or a gene encoding a protein of interest (e.g., ICP0 protein and/or ICP34.5 protein) may be deleted or substituted with an exogenous nucleotide sequence (e.g., nucleotide sequence encoding a foreign protein), thereby preventing the functional expression of the protein of interest.

It is known to those skilled in the art that the genome of HSV virus comprises two copies of ICP0 gene and two copies of ICP34.5 gene. Therefore, in order to prevent the functional expression of ICP0 protein and ICP34.5 protein in the recombinant HSV virus, it is necessary to simultaneously modify the two copies of the ICP0 gene and the two copies of the ICP34.5 gene. However, it would be readily understood that the modifications of the two copies of the ICP0 gene and the two copies of the ICP34.5 gene (4 nucleotide segments) are independent between each other, and may be the same or different.

Thus, in certain preferred embodiments, the recombinant HSV virus has a genome in which the two copies of the ICP0 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein);

the two copies of the ICP34.5 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, the genome of the recombinant HSV virus comprises the following modifications:

the two copies of the ICP0 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein);

the two copies of the ICP34.5 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, one copy of the ICP0 gene comprises a loss-of-function mutation (e.g., addition, deletion, and/or substitution of one or more bases), and the other copy of the ICP0 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP0 gene is deleted and the other copy of the ICP0 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP0 gene is substituted with an exogenous nucleotide sequence (e.g., a nucleotide sequence encoding a foreign protein), and the other copy of the ICP0 gene comprises a loss-of-function mutation (e.g., addition, deletion, and/or substitution of one or more bases) or deleted or substituted with an exogenous nucleotide sequence (e.g., a nucleotide sequence encoding a foreign protein).

In certain preferred embodiments, the two copies of the ICP0 gene each independently comprises a loss-of-function mutation (e.g., addition, deletion, and/or substitution of one or more bases). In certain preferred embodiments, the two copies of the ICP0 gene comprises the same loss-of-function mutation. In certain preferred embodiments, the two copies of the ICP0 gene comprises different loss-of-function mutations. For example, in certain preferred embodiments, the first copy of ICP0 gene comprises a first loss-of-function mutation and the second copy of ICP0 gene comprises a second loss-of-function mutation. The first loss-of-function mutation and the second loss-of-function mutation may be the same or different.

In certain preferred embodiments, the two copies of the ICP0 gene are deleted.

In certain preferred embodiments, the two copies of the ICP0 gene each is independently substituted with an exogenous nucleotide sequence (e.g., a nucleotide sequence encoding a foreign protein). In certain preferred embodiments, the two copies of the ICP0 gene are substituted with the same exogenous nucleotide sequence (e.g., a nucleotide sequence encoding a foreign protein). In certain preferred embodiments, the two copies of the ICP0 gene are substituted with different exogenous nucleotide sequences (e.g., nucleotide sequences encoding foreign proteins). For example, in certain preferred embodiments, the first copy of ICP0 gene is substituted with a first exogenous nucleotide sequence and the second copy of ICP0 gene is substituted with a second exogenous nucleotide sequence. The first exogenous nucleotide sequence and the second exogenous nucleotide sequence may be the same or different.

In certain preferred embodiments, one copy of the ICP34.5 gene comprises a loss-of-function mutation (e.g., addition, deletion, and/or substitution of one or more bases), and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP34.5 gene is deleted and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP34.5 gene is substituted with an exogenous nucleotide sequence (e.g., a nucleotide sequence encoding a foreign protein) and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, the two copies of the ICP34.5 gene each independently comprises a loss-of-function mutation (e.g., addition, deletion, and/or substitution of one or more bases). In certain preferred embodiments, the two copies of the ICP34.5 gene comprise the same loss-of-function mutation. In certain preferred embodiments, the two copies of the ICP34.5 gene comprise different loss-of-function mutations. For example, in certain preferred embodiments, the first copy of the ICP34.5 gene comprises a third loss-of-function mutation and the second copy of the ICP34.5 gene comprises a fourth loss-of-function mutation. The third loss-of-function mutation and the fourth loss-of-function mutation may be the same or different.

In certain preferred embodiments, the two copies of the ICP34.5 gene are deleted.

In certain preferred embodiments, the two copies of the ICP34.5 gene each is independently substituted with an exogenous nucleotide sequence (e.g., a nucleotide sequence encoding a foreign protein). In certain preferred embodiments, the two copies of the ICP34.5 gene are substituted with the same exogenous nucleotide sequence (e.g., a nucleotide sequence encoding a foreign protein). In certain preferred embodiments, the two copies of the ICP34.5 gene are substituted with different exogenous nucleotide sequences (e.g., nucleotide sequences encoding foreign proteins). For example, in certain preferred embodiments, the first copy of the ICP34.5 gene is substituted with a third exogenous nucleotide sequence and the second copy of the ICP34.5 gene is substituted with a fourth exogenous nucleotide sequence. The third exogenous nucleotide sequence and the fourth exogenous nucleotide sequence may be the same or different.

In certain preferred embodiments, the two copies of the ICP0 gene each independently comprises a loss-of-function mutation (e.g., addition, deletion, and/or substitution of one or more bases), and the two copies the ICP34.5 gene each independently comprises a loss-of-function mutation (e.g., addition, deletion, and/or substitution of one or more bases). For example, in certain preferred embodiments, the first copy of the ICP0 gene comprises a first loss-of-function mutation, the second copy of the ICP0 gene comprises a second loss-of-function mutation; and the first copy of the ICP34.5 gene comprises a third loss-of-function mutation, the second copy of the ICP34.5 gene comprises a fourth loss-of-function mutation. The first loss-of-function mutation, the second loss-of-function mutation, the third loss-of-function mutation, and the fourth loss-of-function mutation may be the same or different.

In certain preferred embodiments, the two copies of the ICP0 gene each independently comprises a loss-of-function mutation (e.g., addition, deletion, and/or substitution of one or more bases), and the two copies the ICP34.5 gene are deleted. For example, in certain preferred embodiments, the first copy of the ICP0 gene comprises a first loss-of-function mutation, the second copy of the ICP0 gene comprises a second loss-of-function mutation; and the two copies of the ICP34.5 gene are deleted. The first loss-of-function mutation and the second loss-of-function mutation may be the same or different.

In certain preferred embodiments, the two copies of the ICP0 gene each independently comprises a loss-of-function mutation (e.g., addition, deletion, and/or substitution of one or more bases), and the two copies the ICP34.5 gene each is independently substituted with an exogenous nucleotide sequence (e.g., a nucleotide sequence encoding a foreign protein). For example, in certain preferred embodiments, the first copy of the ICP0 gene comprises a first loss-of-function mutation, the second copy of the ICP0 gene comprises a second loss-of-function mutation; and, the first copy of the ICP34.5 gene is substituted with a third exogenous nucleotide sequence, and the second copy of the ICP34.5 gene is substituted with a fourth exogenous nucleotide sequence. The first loss-of-function mutation and the second loss-of-function mutation may be the same or different. The third exogenous nucleotide sequence and the fourth exogenous nucleotide sequence may be the same or different.

In certain preferred embodiments, the two copies of the ICP0 gene are deleted; and the two copies of the ICP34.5 gene each independently comprises a loss-of-function mutation (e.g., addition, deletion and/or substitution of one or more bases). For example, in certain preferred embodiments, the two copies of the ICP0 gene are deleted; and the first copy of the ICP34.5 gene comprises a third loss-of-function mutation and the second copy of the ICP34.5 gene comprises a fourth loss-of-function mutation. The third loss-of-function mutation and the fourth loss-of-function mutation may be the same or different.

In certain preferred embodiments, the two copies of the ICP0 gene are deleted; and the two copies of the ICP34.5 gene are deleted. In such embodiments, the recombinant HSV virus does not express the ICP0 protein and the ICP34.5 protein. In certain preferred embodiments, the genome of the recombinant HSV virus has deletions of the base sequence between nt510 and nt5439 and the base sequence between nt120802 and nt125731 of the wild-type HSV-1 viral genome.

In certain preferred embodiments, the two copies of the ICP0 gene are deleted; and the two copies of the ICP34.5 gene each is independently substituted with an exogenous nucleotide sequence (e.g., a nucleotide sequence encoding a foreign protein). For example, in certain preferred embodiments, the two copies of the ICP0 gene are deleted; and the first copy of the ICP34.5 gene is substituted with a third exogenous nucleotide sequence, the second copy of ICP34.5 gene is substituted with a fourth exogenous nucleotide sequence. The third exogenous nucleotide sequence and the fourth exogenous nucleotide sequence may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 gene each independently comprise a loss-of-function mutation (e.g., addition, deletion, and/or substitution of one or more bases). For example, in certain preferred embodiments, the first copy of the ICP0 gene is substituted with a first exogenous nucleotide sequence and the second copy of the ICP0 gene is substituted with a second exogenous nucleotide sequence; the first copy of the ICP34.5 gene comprises a third loss-of-function mutation, and the second copy of the ICP34.5 gene comprises a fourth loss-of-function mutation. The first exogenous nucleotide sequence and the second exogenous nucleotide sequence may be the same or different. The third loss-of-function mutation and the fourth loss-of-function mutation may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 gene is deleted. For example, in certain preferred embodiments, the first copy of the ICP0 gene is substituted with a first exogenous nucleotide sequence and the second copy of the ICP0 gene is substituted with a second exogenous nucleotide sequence; the two copies of the ICP34.5 gene are deleted. The first exogenous nucleotide sequence and the second exogenous nucleotide sequence may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 genes each is independently substituted with an exogenous nucleotide sequence (e.g., a nucleotide sequence encoding a foreign protein). For example, in certain preferred embodiments, the first copy of the ICP0 gene is substituted with a first exogenous nucleotide sequence and the second copy of the ICP0 gene is substituted with a second exogenous nucleotide sequence; the first copy of the ICP34.5 gene is substituted with a third exogenous nucleotide sequence and the second copy of the ICP34.5 gene is substituted with a fourth exogenous nucleotide sequence. The first exogenous nucleotide sequence, the second exogenous nucleotide sequence, the third exogenous nucleotide sequence, and the fourth exogenous nucleotide sequence may be the same or different.

In certain preferred embodiments, the first loss-of-function mutation, the second loss-of-function mutation, the third loss-of-function mutation, and the fourth loss-of-function mutation each is independently selected from missense mutation, nonsense mutation, frameshift mutation, base deletion, base substitution, base addition, and any combination thereof (e.g., deletion or substitution or addition of a gene fragment).

In certain preferred embodiments, the first exogenous nucleotide sequence, the second exogenous nucleotide sequence, the third exogenous nucleotide sequence, and the fourth exogenous nucleotide sequence each independently encodes an exogenous protein selected from the group consisting of fluorescent proteins, immunomodulatory polypeptides, cytokines, chemokines, antibodies, and cytotoxic peptides.

In certain preferred embodiments, the fluorescent protein is selected from the group consisting of green fluorescent protein (e.g., a green fluorescent protein having the amino acid sequence set forth in SEQ ID NO: 7), red fluorescent protein, blue fluorescent protein, yellow fluorescent protein, and any combination thereof.

In certain preferred embodiments, the immunomodulatory polypeptide is selected from the group consisting of CD40L, OX40L, inducible costimulatory molecule (ICOS), FTL3L, LIGHT, CD137L, CD70, 4-1BB, GITR, CD28, and any combination thereof.

In certain preferred embodiments, the cytokine is selected from the group consisting of interleukin (e.g., IL-2, IL-12, and IL-15), interferon (e.g., IFNα, IFNβ, IFNγ), tumor necrosis factor (e.g., TNFα), colony stimulating factor (e.g., GM-CSF), and any combination thereof.

In certain preferred embodiments, the chemokine is selected from the group consisting of CCL2, RANTES, CCL7, CCL9, CCL10, CCL12, CCL15, CCL19, CCL21, CCL20, XCL-1, and any combination thereof.

In certain preferred embodiments, the cytotoxic peptide is selected from the group consisting of thymidine kinase TK (TK/GCV), TRAIL, FasL, and any combination thereof.

In certain preferred embodiments, the antibody is selected from the group consisting of anti-PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody, anti-EGFR antibody, anti-VEGFR antibody, anti-HER2 antibody, anti-PDGFR antibody, and any combination thereof.

In the past five years, antibody drugs against PD-1 have achieved great clinical success and have been approved by the FDA for the treatment of solid tumor patients such as melanoma and lung cancer. However, clinical studies have shown that anti-PD-1 antibodies are only effective in about 30% of solid tumor patients. This may be because T cells are difficult to penetrate into a solid tumor and cannot act on a tumor cell inside the solid tumor together with the anti-PD-1 antibody. Without being bound by any theory, oncolytic HSV viruses not only directly target and kill tumor cells, but also induce immune cells (such as T cells) to infiltrate tumors. Therefore, the combination use of the recombinant HSV virus of the present invention and the anti-PD-1 antibody may be particularly advantageous for improving the effect of tumor treatment, and has great application prospects in tumor immunotherapy. Accordingly, in certain preferred embodiments, the foreign protein is an anti-PD-L1 antibody, an anti-PD-1 antibody, or any combination thereof. For example, the foreign protein is an anti-PD-1 single chain antibody.

In certain preferred embodiments, the recombinant HSV virus is a recombinant HSV-1 virus, a recombinant HSV-2 virus, or an HSV-1/HSV-2 chimeric virus (i.e., a recombinant HSV virus which genome comprises both the DNA derived from HSV-1 and the DNA derived from HSV-2). In certain preferred embodiments, the recombinant HSV virus is derived from an HSV-1 strain KOS.

In certain preferred embodiments, the recombinant HSV virus is capable of expressing a functional UL43 protein, a functional UL41 protein (i.e., vhs protein), a functional UL48 protein (i.e., VMW65 protein), or any combination thereof. In certain preferred embodiments, the recombinant HSV virus is capable of expressing a functional UL43 protein. In certain preferred embodiments, the recombinant HSV virus is capable of expressing a functional UL41 protein. In certain preferred embodiments, the recombinant HSV virus is capable of expressing a functional UL48 protein. In certain preferred embodiments, the recombinant HSV virus is capable of expressing a functional UL43 protein and a functional UL41 protein. In certain preferred embodiments, the recombinant HSV virus is capable of expressing a functional UL43 protein and a functional UL48 protein. In certain preferred embodiments, the recombinant HSV virus is capable of expressing a functional UL41 protein and a functional UL48 protein. In certain preferred embodiments, the recombinant HSV virus is capable of expressing a functional UL43 protein, a functional UL41 protein, and a functional UL48 protein.

In certain preferred embodiments, the genome of the recombinant HSV virus comprises a UL43 gene capable of expressing a functional UL43 protein, a UL41 gene (i.e., a vhs gene) capable of expressing a functional UL41 protein, and/or a UL48 gene (i.e., the VMW65 gene) capable of expressing a function UL48 protein. In certain preferred embodiments, the genome of the recombinant HSV virus comprises a UL43 gene capable of expressing a functional UL43 protein. In certain preferred embodiments, the genome of the recombinant HSV virus comprises a UL41 gene capable of expressing a functional UL41 protein. In certain preferred embodiments, the genome of the recombinant HSV virus comprises a UL48 gene capable of expressing a functional UL48 protein. In certain preferred embodiments, the genome of the recombinant HSV virus comprises a UL43 gene capable of expressing a functional UL43 protein, and a UL41 gene capable of expressing a functional UL41 protein. In certain preferred embodiments, the genome of the recombinant HSV virus comprises a UL43 gene capable of expressing a functional UL43 protein, and a UL48 gene capable of expressing a functional UL48 protein. In certain preferred embodiments, the genome of the recombinant HSV virus comprises a UL41 gene capable of expressing a functional UL41 protein, and a UL48 gene capable of expressing a functional UL48 protein. In certain preferred embodiments, the genome of the recombinant HSV virus comprises a UL43 gene capable of expressing a functional UL43 protein, a UL41 gene capable of expressing a functional UL41 protein, and a UL48 gene capable of expressing a functional UL48 protein.

In certain preferred embodiments, the genome of the recombinant HSV virus comprises a UL43 gene, a UL41 gene (i.e., a vhs gene), and/or a UL48 gene (i.e., a VMW65 gene), and the UL43 gene, the UL41 gene and/or the UL48 gene do not comprise a loss-of-function mutation. In certain preferred embodiments, the genome of the recombinant HSV virus comprises a UL43 gene that does not comprise a loss-of-function mutation. In certain preferred embodiments, the genome of the recombinant HSV virus comprises a UL41 gene that does not comprise a loss-of-function mutation. In certain preferred embodiments, the genome of the recombinant HSV virus comprises a UL48 gene that does not comprise a loss-of-function mutation. In certain preferred embodiments, the genome of the recombinant HSV virus comprises a UL43 gene and a UL41 gene that do not comprise a loss-of-function mutation. In certain preferred embodiments, the genome of the recombinant HSV virus comprises a UL43 gene and a UL48 gene that do not comprise a loss-of-function mutation. In certain preferred embodiments, the genome of the recombinant HSV virus comprises a UL41 gene and a UL48 gene that do not comprise a loss-of-function mutation. In certain preferred embodiments, the genome of the recombinant HSV virus comprises a UL43 gene, a UL41 gene, and a UL48 gene that do not comprise a loss-of-function mutation.

In certain preferred embodiments, the genome of the recombinant HSV virus further comprises a modification in which one or more non-essential genes are deleted or mutated (e.g., comprise a loss-of-function mutation, or are substituted with an exogenous nucleotide sequence). In certain preferred embodiments, the non-essential gene is selected from the group consisting of UL3 gene, UL4 gene, UL14 gene, UL16 gene, UL21 gene, UL24 gene, UL31 gene, UL32 gene, US3 gene, UL51 gene, UL55 gene, UL56 Gene, US2 gene, US12 gene (i.e., ICP47 gene), LAT gene, nucleotide fragment corresponding to nt5853-nt7485 of JQ673480.1, and any combination thereof. In certain preferred embodiments, in the genome of the recombinant HSV virus, the UL3 gene is deleted or mutated (e.g., comprises a loss-of-function mutation, or is substituted with an exogenous nucleotide sequence). In certain preferred embodiments, in the genome of the recombinant HSV virus, the UL4 gene is deleted or mutated (e.g., comprises a loss-of-function mutation, or is substituted with an exogenous nucleotide sequence). In certain preferred embodiments, in the genome of the recombinant HSV virus, the UL14 gene is deleted or mutated (e.g., comprises a loss-of-function mutation, or is substituted with an exogenous nucleotide sequence). In certain preferred embodiments, in the genome of the recombinant HSV virus, the UL16 gene is deleted or mutated (e.g., comprises a loss-of-function mutation, or is substituted with an exogenous nucleotide sequence). In certain preferred embodiments, in the genome of the recombinant HSV virus, the UL21 gene is deleted or mutated (e.g., comprises a loss-of-function mutation, or is substituted with an exogenous nucleotide sequence). In certain preferred embodiments, in the genome of the recombinant HSV virus, the UL24 gene is deleted or mutated (e.g., comprises a loss-of-function mutation, or is substituted with an exogenous nucleotide sequence). In certain preferred embodiments, in the genome of the recombinant HSV virus, the UL31 gene is deleted or mutated (e.g., comprises a loss-of-function mutation, or is substituted with an exogenous nucleotide sequence). In certain preferred embodiments, in the genome of the recombinant HSV virus, the UL32 gene is deleted or mutated (e.g., comprises a loss-of-function mutation, or is substituted with an exogenous nucleotide sequence). In certain preferred embodiments, in the genome of the recombinant HSV virus, the US3 gene is deleted or mutated (e.g., comprises a loss-of-function mutation, or is substituted with an exogenous nucleotide sequence). In certain preferred embodiments, in the genome of the recombinant HSV virus, the UL51 gene is deleted or mutated (e.g., comprises a loss-of-function mutation, or is substituted with an exogenous nucleotide sequence). In certain preferred embodiments, in the genome of the recombinant HSV virus, the UL55 gene is deleted or mutated (e.g., comprises a loss-of-function mutation, or is substituted with an exogenous nucleotide sequence). In certain preferred embodiments, in the genome of the recombinant HSV virus, the UL56 gene is deleted or mutated (e.g., comprises a loss-of-function mutation, or is substituted with an exogenous nucleotide sequence). In certain preferred embodiments, in the genome of the recombinant HSV virus, the US2 gene is deleted or mutated (e.g., comprises a loss-of-function mutation, or is substituted with an exogenous nucleotide sequence). In certain preferred embodiments, in the genome of the recombinant HSV virus, the US12 gene is deleted or mutated (e.g., comprises a loss-of-function mutation, or is substituted with an exogenous nucleotide sequence). In certain preferred embodiments, in the genome of the recombinant HSV virus, the LAT gene is deleted or mutated (e.g., comprises a loss-of-function mutation, or is substituted with an exogenous nucleotide sequence). In certain preferred embodiments, in the genome of the recombinant HSV virus, a nucleotide fragment corresponding to nt5853-nt7485 of JQ673480.1 is deleted or mutated (e.g., comprises a loss-of-function mutation, or is substituted by an exogenous nucleotide sequence).

In certain preferred embodiments, the genome of the recombinant HSV virus further comprises one or more of the following modifications: deletion or mutation in one or more of UL55 gene, US2 gene, LAT gene, and nucleotide fragment corresponding to nt5853-nt7485 of JQ673480.1 (for example, comprising a loss-of-function mutation, or being substituted with an exogenous nucleotide sequence). In certain preferred embodiments, the genome of the recombinant HSV virus further comprises the following modification: deletion or mutation of UL55 gene, US2 gene, LAT gene, or nucleotide fragment corresponding to nt5853-nt7485 of JQ673480.1 (for example, comprising a loss-of-function mutation or being substituted with an exogenous nucleotide sequence).

In certain preferred embodiments, the essential gene of the recombinant HSV virus is not deleted and does not comprise a loss-of-function mutation. In certain preferred embodiments, the coding sequence for the essential gene of the recombinant HSV virus is not deleted or mutated. In certain preferred embodiments, the recombinant HSV virus is capable of expressing all essential genes. In certain preferred embodiments, the genome of the recombinant HSV virus comprises all essential genes, and none of the essential genes comprises a loss-of-function mutation. In certain preferred embodiments, the genome of the recombinant HSV virus comprises all essential genes, and none of the coding sequences of the essential genes comprises a mutation. In general, the essential genes are essential for survival and replication of HSV viruses, and therefore, in the recombinant HSV virus, none of the essential genes comprises a loss-of-function mutation. However, it is readily understood that the promoter of such an essential gene can be engineered (for example, the native promoter of the essential gene can be substituted with a tumor-specific promoter, such as a promoter of hTERT), thereby further enhancing the safety of the recombinant HSV virus without affecting the function/properties of the recombinant HSV virus of the invention. Thus, in certain preferred embodiments, in the genome of the recombinant HSV virus, a native promoter of one or more essential genes is substituted with a tumor-specific promoter, such as a promoter of hTERT. In certain preferred embodiments, the essential gene is selected from the group consisting of ICP27 gene, ICP4 gene, VP5 gene, gL gene, gH gene, gD gene, gK gene, gB gene, gN gene, UL5 gene, UL6 gene, UL8 gene, UL9 gene, UL12 gene, UL25 gene, UL26 gene, UL28 gene, UL29 gene, UL30 gene, UL33 gene, UL36 gene, UL38 gene, UL42 gene, UL48 gene, UL52 gene, and any combination thereof.

In certain preferred embodiments, the genome of the recombinant HSV virus comprises all other genes of the wild-type HSV virus, except for the two copies of the ICP0 gene and the two copies of the ICP34.5 gene as described above, and none of the other genes comprises a loss-of-function mutation. However, it is readily understood that a promoter of the other genes can be engineered (e.g., a native promoter can be substituted with a tumor-specific promoter, such as a promoter of hTERT), thereby further enhancing the safety of the recombinant HSV virus without affecting the functions/properties of the recombinant HSV virus of the invention. Thus, in certain preferred embodiments, the genome of the recombinant HSV virus further comprises a modification in which a native promoter of one or more HSV genes is substituted with a tumor-specific promoter, such as a promoter of hTERT. In certain preferred embodiments, the HSV gene is selected from the group consisting of VP5 gene, ICP27 gene, and ICP4 gene.

In certain preferred embodiments, the genome of the recombinant HSV virus further comprises one or more modifications selected from the group consisting of:

(1) substitution of a native promoter of the VP5 gene with a tumor-specific promoter, such as a promoter of hTERT;

(2) substitution of a native promoter of the ICP27 gene with a tumor-specific promoter, such as a promoter of hTERT;

(3) substitution of a native promoter of the ICP4 gene with a tumor-specific promoter, such as a promoter of hTERT;

(4) deletion or mutation of one or more of the UL55 gene, the US2 gene, the LAT gene, and the nucleotide fragment corresponding to nt5853-nt7485 of JQ673480.1 (for example, comprising a loss-of-function mutation, or being substituted with an exogenous nucleotide sequence).

In certain preferred embodiments, the hTERT promoter has a sequence set forth in SEQ ID NO: 5.

In addition, the recombinant HSV viruses of the invention can also be modified to carry one or more exogenous nucleotide sequences. For example, in certain preferred embodiments, the genome of the recombinant HSV virus further comprises a fifth exogenous nucleotide sequence. In certain preferred embodiments, the fifth exogenous nucleotide sequence encodes a foreign protein selected from the group consisting of fluorescent protein, immunomodulatory polypeptide, cytokine, chemokine, antibody, and cytotoxic peptide.

In the present application, a loss-of-function mutations can be introduced into the various viral genes as above-mentioned by techniques well known in the art. For example, a loss-of-function mutation can be introduced into a viral gene by deletion, substitution or insertion of a base so as to functionally inactivate the viral gene. In certain exemplary embodiments, the viral gene is functionally inactivated by deletion (e.g., deletion of the entire gene or a portion thereof). In such embodiments, at least 25%, at least 50%, at least 75%, or 100% of a sequence of a viral gene of interest may be deleted, or at least 10 bp, at least 100 bp, or at least 1000 bp of a sequence of a viral gene of interest may be deleted. In certain exemplary embodiments, a frameshift mutation is caused by insertion or deletion of a base so as to functionally inactive the viral gene. In certain exemplary embodiments, the viral gene is functionally inactivated by replacing the entire gene of interest or a portion thereof with an exogenous nucleotide sequence.

Viral Vector

In another aspect, the invention provides a viral vector comprising the genome of the recombinant HSV virus according to the invention or consisting of the genome of the recombinant HSV virus according to the invention.

In another aspect, the invention provides a viral vector comprising or consisting of a mutated HSV genome that does not express functional ICP0 protein and ICP34.5 protein.

In certain preferred embodiments, in the mutated HSV genome, the two copies of the ICP0 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein);

the two copies of the ICP34.5 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, the mutated HSV genome comprises the following modifications:

the two copies of the ICP0 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein);

the two copies of the ICP34.5 gene each independently comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, one copy of the ICP0 gene comprises a loss-of-function mutation (e.g., addition, deletion, and/or substitution of one or more bases), and the other copy of the ICP0 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP0 gene is deleted and the other copy of the ICP0 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP0 gene is substituted with an exogenous nucleotide sequence (e.g., a nucleotide sequence encoding a foreign protein), and the other copy of the ICP0 gene comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, the two copies of the ICP0 gene each independently comprises a loss-of-function mutation (e.g., addition, deletion, and/or substitution of one or more bases). In certain preferred embodiments, the two copies of the ICP0 gene comprise the same loss-of-function mutation. In certain preferred embodiments, the two copies of the ICP0 gene comprise different loss-of-function mutations. For example, in certain preferred embodiments, the first copy of the ICP0 gene comprises a first loss-of-function mutation and the second copy of the ICP0 gene comprises a second loss-of-function mutation. The first loss-of-function mutation and the second loss-of-function mutation may be the same or different.

In certain preferred embodiments, the two copies of the ICP0 gene are deleted. In certain preferred embodiments, the two copies of the ICP0 gene each is independently substituted with an exogenous nucleotide sequence (e.g., a nucleotide sequence encoding a foreign protein). In certain preferred embodiments, the two copies of the ICP0 gene are substituted with the same exogenous nucleotide sequence (e.g., a nucleotide sequence encoding a foreign protein). In certain preferred embodiments, the two copies of the ICP0 gene are substituted with different exogenous nucleotide sequences (e.g., nucleotide sequences encoding foreign proteins). For example, in certain preferred embodiments, the first copy of the ICP0 gene is substituted with a first exogenous nucleotide sequence and the second copy of the ICP0 gene is substituted with a second exogenous nucleotide sequence. The first exogenous nucleotide sequence and the second exogenous nucleotide sequence may be the same or different.

In certain preferred embodiments, one copy of the ICP34.5 gene comprises a loss-of-function mutation (e.g., addition, deletion, and/or substitution of one or more bases), and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP34.5 gene is deleted and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein). In certain preferred embodiments, one copy of the ICP34.5 gene is substituted with an exogenous nucleotide sequence (e.g., a nucleotide sequence encoding a foreign protein) and the other copy of the ICP34.5 gene comprises a loss-of-function mutation (e.g., addition, deletion, and/or substitution of one or more bases) or is deleted or substituted with an exogenous nucleotide sequence (e.g., a nucleotide sequence encoding a foreign protein).

In certain preferred embodiments, the two copies of the ICP34.5 gene each independently comprises a loss-of-function mutation (e.g., addition, deletion, and/or substitution of one or more bases). In certain preferred embodiments, the two copies of the ICP34.5 gene comprise the same loss-of-function mutation. In certain preferred embodiments, the two copies of the ICP34.5 gene comprise different loss-of-function mutations. For example, in certain preferred embodiments, the first copy of the ICP34.5 gene comprises a third loss-of-function mutation and the second copy of the ICP34.5 gene comprises a fourth loss-of-function mutation. The third loss-of-function mutation and the fourth loss-of-function mutation may be the same or different.

In certain preferred embodiments, the two copies of the ICP34.5 gene are deleted.

In certain preferred embodiments, the two copies of the ICP34.5 gene each is independently substituted with an exogenous nucleotide sequence (e.g., a nucleotide sequence encoding a foreign protein). In certain preferred embodiments, the two copies of the ICP34.5 gene are substituted with the same exogenous nucleotide sequence (e.g., a nucleotide sequence encoding a foreign protein). In certain preferred embodiments, the two copies of the ICP34.5 gene are substituted with different exogenous nucleotide sequences (e.g., nucleotide sequences encoding foreign proteins). For example, in certain preferred embodiments, the first copy of the ICP34.5 gene is substituted with a third exogenous nucleotide sequence and the second copy of the ICP34.5 gene is substituted with a fourth exogenous nucleotide sequence. The third exogenous nucleotide sequence and the fourth exogenous nucleotide sequence may be the same or different.

In certain preferred embodiments, the two copies of the ICP0 gene each independently comprises a loss-of-function mutation (e.g., addition, deletion, and/or substitution of one or more bases), and the two copies of the ICP34.5 gene each independently comprises a loss-of-function mutation (e.g., addition, deletion, and/or substitution of one or more bases). For example, in certain preferred embodiments, the first copy of the ICP0 gene comprises a first loss-of-function mutation, the second copy of the ICP0 gene comprises a second loss-of-function mutation; and the first copy of the ICP34.5 gene comprises a third loss-of-function mutation, the second copy of the ICP34.5 gene comprises a fourth loss-of-function mutation. The first loss-of-function mutation, the second loss-of-function mutation, the third loss-of-function mutation, and the fourth loss-of-function mutation may be the same or different.

In certain preferred embodiments, the two copies of the ICP0 gene each independently comprises a loss-of-function mutation (e.g., addition, deletion, and/or substitution of one or more bases), and the two copies of the ICP34.5 gene are deleted. For example, in certain preferred embodiments, the first copy of the ICP0 gene comprises a first loss-of-function mutation, the second copy of the ICP0 gene comprises a second loss-of-function mutation; and, the two copies of ICP34.5 gene are deleted. The first loss-of-function mutation and the second loss-of-function mutation may be the same or different.

In certain preferred embodiments, the two copies of the ICP0 gene each independently comprises a loss-of-function mutation (e.g., addition, deletion, and/or substitution of one or more bases), and the two copies of the ICP34.5 gene each is independently substituted with an exogenous nucleotide sequence (e.g., a nucleotide sequence encoding a foreign protein). For example, in certain preferred embodiments, the first copy of the ICP0 gene comprises a first loss-of-function mutation, the second copy of the ICP0 gene comprises a second loss-of-function mutation; and, the first copy of the ICP34.5 gene is substituted with a third exogenous nucleotide sequence, and the second copy of the ICP34.5 gene is substituted with a fourth exogenous nucleotide sequence. The first loss-of-function mutation and the second loss-of-function mutation may be the same or different. The third exogenous nucleotide sequence and the fourth exogenous nucleotide sequence may be the same or different.

In certain preferred embodiments, the two copies of the ICP0 gene are deleted; and the two copies of the ICP34.5 gene each independently comprises a loss-of-function mutation (e.g., addition, deletion, and/or substitution of one or more bases). For example, in certain preferred embodiments, the two copies of the ICP0 gene are deleted; and the first copy of the ICP34.5 gene comprises a third loss-of-function mutation and the second copy of the ICP34.5 gene comprises a fourth loss-of-function mutation. The third loss-of-function mutation and the fourth loss-of-function mutation may be the same or different.

In certain preferred embodiments, the two copies of the ICP0 gene are deleted; and the two copies of the ICP34.5 gene are deleted. In such embodiments, the viral vector does not comprise a gene encoding ICP0 protein and a gene encoding ICP34.5 protein. In certain preferred embodiments, the mutated HSV genome lacks a base sequence between nt510 and nt5439 and a base sequence between nt120802 and nt125731 of the wild-type HSV-1 viral genome.

In certain preferred embodiments, the two copies of the ICP0 gene are deleted; and the two copies of the ICP34.5 gene each is independently substituted with an exogenous nucleotide sequence (e.g., a nucleotide sequence encoding a foreign protein). For example, in certain preferred embodiments, the two copies of the ICP0 gene are deleted; and the first copy of the ICP34.5 gene is substituted with a third exogenous nucleotide sequence, the second copy of ICP34.5 gene is substituted with a fourth exogenous nucleotide sequence. The third exogenous nucleotide sequence and the fourth exogenous nucleotide sequence may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 gene each independently comprises a loss-of-function mutation (e.g., addition, deletion, and/or substitution of one or more bases). For example, in certain preferred embodiments, the first copy of the ICP0 gene is substituted with a first exogenous nucleotide sequence and the second copy of the ICP0 gene is substituted with a second exogenous nucleotide sequence; the first copy of the ICP34.5 gene comprises a third loss-of-function mutation, and the second copy of the ICP34.5 gene comprises a fourth loss-of-function mutation. The first exogenous nucleotide sequence and the second exogenous nucleotide sequence may be the same or different. The third loss-of-function mutation and the fourth-function loss-of-function mutation may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 gene are deleted. For example, in certain preferred embodiments, the first copy of the ICP0 gene is substituted with a first exogenous nucleotide sequence and the second copy of the ICP0 gene is substituted with a second exogenous nucleotide sequence; the two copies of the ICP34.5 gene are deleted. The first exogenous nucleotide sequence and the second exogenous nucleotide sequence may be the same or different.

In certain preferred embodiments, the two copies of the ICP0 gene each is independently substituted with an exogenous nucleotide sequence (e.g., a nucleotide sequence encoding a foreign protein), and the two copies of the ICP34.5 gene each is independently substituted with an exogenous nucleotide sequence (e.g., a nucleotide sequence encoding a foreign protein). For example, in certain preferred embodiments, the first copy of the ICP0 gene is substituted with a first exogenous nucleotide sequence and the second copy of the ICP0 gene is substituted with a second exogenous nucleotide sequence; the first copy of the ICP34.5 gene is substituted with a third exogenous nucleotide sequence and the second copy of the ICP34.5 gene is substituted with a fourth exogenous nucleotide sequence. The first exogenous nucleotide sequence, the second exogenous nucleotide sequence, the third exogenous nucleotide sequence, and the fourth exogenous nucleotide sequence may be the same or different.

In certain preferred embodiments, the first loss-of-function mutation, the second loss-of-function mutation, the third loss-of-function mutation, and the fourth loss-of-function mutation each is independently selected from the group consisting of missense mutation, nonsense mutation, frameshift mutation, base deletion, base substitution, base addition, and any combination thereof (e.g., deletion or substitution or addition of gene fragment).

In certain preferred embodiments, the first exogenous nucleotide sequence, the second exogenous nucleotide sequence, the third exogenous nucleotide sequence, and the fourth exogenous nucleotide sequence each independently encodes an exogenous protein selected from the group consisting of fluorescent protein, immunomodulatory polypeptide, cytokine, chemokine, antibody, and cytotoxic peptide.

In certain preferred embodiments, the fluorescent protein is selected from the group consisting of green fluorescent protein (e.g., green fluorescent protein having an amino acid sequence set forth in SEQ ID NO: 7), red fluorescent protein, blue fluorescent protein, yellow fluorescent protein, and any combination thereof.

In certain preferred embodiments, the immunomodulatory polypeptide is selected from the group consisting of CD40L, OX40L, inducible costimulatory molecules (ICOS), FTL3L, LIGHT, CD137L, CD70, 4-1BB, GITR, CD28, and any combination thereof.

In certain preferred embodiments, the cytokine is selected from the group consisting of interleukin (e.g., IL-2, IL-12, and IL-15), interferon (e.g., IFNα, IFNβ, IFNγ), tumor necrosis factor (e.g., TNFα), colony stimulating factor (e.g., GM-CSF), and any combination thereof.

In certain preferred embodiments, the chemokine is selected from the group consisting of CCL2, RANTES, CCL7, CCL9, CCL10, CCL12, CCL15, CCL19, CCL21, CCL20, XCL-1, and any combination thereof.

In certain preferred embodiments, the cytotoxic peptide is selected from the group consisting of thymidine kinase TK (TK/GCV), TRAIL, FasL, and any combination thereof.

In certain preferred embodiments, the antibody is selected from the group consisting of anti-PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody, anti-EGFR antibody, anti-VEGFR antibody, anti-HER2 antibody, anti-PDGFR antibody, and any combination thereof.

In certain preferred embodiments, the foreign protein is an anti-PD-L1 antibody, an anti-PD-1 antibody, or any combination thereof. For example, the foreign protein is an anti-PD-1 single chain antibody.

In certain preferred embodiments, the mutated HSV genome is derived from an HSV-1 virus, an HSV-2 virus, or an HSV-1/HSV-2 chimeric virus (i.e., a recombinant HSV virus which genome comprises both an DNA derived from HSV-1 and an DNA derived from HSV-2). In certain preferred embodiments, the mutated HSV genome is derived from a genome of HSV-1 strain KOS. In certain preferred embodiments, the mutated HSV genome is derived from a genome set forth in GenBank: JQ673480.1.

In certain preferred embodiments, the mutated HSV genome is capable of expressing a functional UL43 protein, a functional UL41 protein (i.e., a vhs protein), a functional UL48 protein (i.e., a VMW65 protein), or any combination thereof. In certain preferred embodiments, the mutated HSV genome is capable of expressing a functional UL43 protein. In certain preferred embodiments, the mutated HSV genome is capable of expressing a functional UL41 protein. In certain preferred embodiments, the mutated HSV genome is capable of expressing a functional UL48 protein. In certain preferred embodiments, the mutated HSV genome is capable of expressing a functional UL43 protein and a functional UL41 protein. In certain preferred embodiments, the mutated HSV genome is capable of expressing a functional UL43 protein and a functional UL48 protein. In certain preferred embodiments, the mutated HSV genome is capable of expressing a functional UL41 protein and a functional UL48 protein. In certain preferred embodiments, the mutated HSV genome is capable of expressing a functional UL43 protein, a functional UL41 protein, and a functional UL48 protein.

In certain preferred embodiments, the mutated HSV genome comprises a UL43 gene capable of expressing a functional UL43 protein, a UL41 gene (i.e., a vhs gene) capable of expressing a functional UL41 protein, and/or a UL48 gene (i.e., a VMW65 gene) capable of expressing a functional UL48 protein. In certain preferred embodiments, the mutated HSV genome comprises a UL43 gene capable of expressing a functional UL43 protein. In certain preferred embodiments, the mutated HSV genome comprises a UL41 gene capable of expressing a functional UL41 protein. In certain preferred embodiments, the mutated HSV genome comprises a UL48 gene capable of expressing a functional UL48 protein. In certain preferred embodiments, the mutated HSV genome comprises a UL43 gene capable of expressing a functional UL43 protein, and a UL41 gene capable of expressing a functional UL41 protein. In certain preferred embodiments, the mutated HSV genome comprises a UL43 gene capable of expressing a functional UL43 protein, and a UL48 gene capable of expressing a functional UL48 protein. In certain preferred embodiments, the mutated HSV genome comprises a UL41 gene capable of expressing a functional UL41 protein, and a UL48 gene capable of expressing a functional UL48 protein. In certain preferred embodiments, the mutated HSV genome comprises a UL43 gene capable of expressing a functional UL43 protein, a UL41 gene capable of expressing a functional UL41 protein, and a UL48 gene capable of expressing a functional UL48 protein.

In certain preferred embodiments, the mutated HSV genome comprises a UL43 gene, a UL41 gene (i.e., a vhs gene), and/or a UL48 gene (i.e., a VMW65 gene), and the UL43 gene, the UL41 gene, and/or the UL48 gene do not comprise a loss-of-function mutation. In certain preferred embodiments, the mutated HSV genome comprises a UL43 gene that does not comprise a loss-of-function mutation. In certain preferred embodiments, the mutated HSV genome comprises a UL41 gene that does not comprise a loss-of-function mutation. In certain preferred embodiments, the mutated HSV genome comprises a UL48 gene that does not comprise a loss-of-function mutation. In certain preferred embodiments, the mutated HSV genome comprises a UL43 gene and a UL41 gene that do not comprise a loss-of-function mutation. In certain preferred embodiments, the mutated HSV genome comprises a UL43 gene and a UL48 gene that do not comprise a loss-of-function mutation. In certain preferred embodiments, the mutated HSV genome comprises a UL41 gene and a UL48 gene that do not comprise a loss-of-function mutation. In certain preferred embodiments, the mutated HSV genome comprises a UL43 gene, a UL41 gene, and a UL48 gene that do not comprise a loss-of-function mutation.

In certain preferred embodiments, the mutated HSV genome further comprises a modification in which one or more non-essential genes are deleted or mutated (e.g., comprise a loss-of-function mutation, or are substituted with an exogenous nucleotide sequence). In certain preferred embodiments, the non-essential gene is selected from the group consisting of UL3 gene, UL4 gene, UL14 gene, UL16 gene, UL21 gene, UL24 gene, UL31 gene, UL32 gene, US3 gene, UL51 gene, UL55 gene, UL56 Gene, US2 gene, US12 gene (i.e., ICP47 gene), LAT gene, nucleotide fragment corresponding to nt5853-nt7485 of JQ673480.1, and any combination thereof. In certain preferred embodiments, in the mutated HSV genome, the UL3 gene is deleted or mutated (e.g., comprises a loss-of-function mutation, or is substituted with an exogenous nucleotide sequence). In certain preferred embodiments, in the mutated HSV genome, the UL4 gene is deleted or mutated (e.g., comprises a loss-of-function mutation, or is substituted with an exogenous nucleotide sequence). In certain preferred embodiments, in the mutated HSV genome, the UL14 gene is deleted or mutated (e.g., comprises a loss-of-function mutation, or is substituted with an exogenous nucleotide sequence). In certain preferred embodiments, in the mutated HSV genome, the UL16 gene is deleted or mutated (e.g., comprises a loss-of-function mutation, or is substituted with an exogenous nucleotide sequence). In certain preferred embodiments, in the mutated HSV genome, the UL21 gene is deleted or mutated (e.g., comprises a loss-of-function mutation, or is substituted with an exogenous nucleotide sequence). In certain preferred embodiments, in the mutated HSV genome, the UL24 gene is deleted or mutated (e.g., comprises a loss-of-function mutation, or is substituted with an exogenous nucleotide sequence). In certain preferred embodiments, in the mutated HSV genome, the UL31 gene is deleted or mutated (e.g., comprises a loss-of-function mutation, or is substituted with an exogenous nucleotide sequence). In certain preferred embodiments, in the mutated HSV genome, the UL32 gene is deleted or mutated (e.g., comprises a loss-of-function mutation, or is substituted with an exogenous nucleotide sequence). In certain preferred embodiments, in the mutated HSV genome, the US3 gene is deleted or mutated (e.g., comprises a loss-of-function mutation, or is substituted with an exogenous nucleotide sequence). In certain preferred embodiments, in the mutated HSV genome, the UL51 gene is deleted or mutated (e.g., comprises a loss-of-function mutation, or is substituted with an exogenous nucleotide sequence). In certain preferred embodiments, in the mutated HSV genome, the UL55 gene is deleted or mutated (e.g., comprises a loss-of-function mutation, or is substituted with an exogenous nucleotide sequence). In certain preferred embodiments, in the mutated HSV genome, the UL56 gene is deleted or mutated (e.g., comprises a loss-of-function mutation, or is substituted with an exogenous nucleotide sequence). In certain preferred embodiments, in the mutated HSV genome, the US2 gene is deleted or mutated (e.g., comprises a loss-of-function mutation, or is substituted with an exogenous nucleotide sequence). In certain preferred embodiments, in the mutated HSV genome, the US12 gene is deleted or mutated (e.g., comprises a loss-of-function mutation, or is substituted with an exogenous nucleotide sequence). In certain preferred embodiments, in the mutated HSV genome, the LAT gene is deleted or mutated (e.g., comprises a loss-of-function mutation, or is substituted with an exogenous nucleotide sequence). In certain preferred embodiments, in the mutated HSV genome, a nucleotide fragment of nt5853-nt7485 corresponding to JQ673480.1 is deleted or mutated (e.g., comprises a loss-of-function mutation, or is substituted with an exogenous nucleotide sequence).

In certain preferred embodiments, the mutated HSV genome further comprises one or more of the following modifications: deletion or mutation of one or more of UL55 gene, US2 gene, LAT gene, and nucleotide fragment corresponding to nt5853-nt7485 of JQ673480.1 (for example, comprising a loss-of-function mutation, or being substituted with an exogenous nucleotide sequence). In certain preferred embodiments, the mutated HSV genome further comprises a modification: deletion or mutation of UL55 gene, US2 gene, LAT gene, or nucleotide fragment corresponding to nt5853-nt7485 of JQ673480.1 (for example, comprising a loss-of-function mutation or being substituted with an exogenous nucleotide sequence).

In certain preferred embodiments, the essential gene in the mutated HSV genome is not deleted and does not comprise a loss-of-function mutation. In certain preferred embodiments, the coding sequence of the essential gene in the mutated HSV genome is not deleted or mutated. In certain preferred embodiments, the mutated HSV genome is capable of expressing all essential genes. In certain preferred embodiments, the mutated HSV genome comprises all essential genes, and none of the essential genes comprises a loss-of-function mutation. In certain preferred embodiments, the mutated HSV genome comprises all essential genes, and none of the coding sequences of the essential genes comprises a mutation. In general, the essential genes are essential for survival and replication of the HSV virus, and therefore, in the genome of the recombinant HSV virus, none of the essential genes comprises a loss-of-function mutation. However, it is readily understood that a promoter of such essential gene can be engineered (for example, a native promoter of the essential gene is substituted with a tumor-specific promoter, such as a promoter of hTERT), thereby further enhancing the safety of the recombinant HSV virus without affecting the functions/properties of the recombinant HSV virus of the invention. Thus, in certain preferred embodiments, in the mutated HSV genome, a native promoter of one or more of the essential genes is substituted with a tumor-specific promoter, such as a promoter of hTERT. In certain preferred embodiments, the essential gene is selected from the group consisting of ICP27 gene, ICP4 gene, VP5 gene, gL gene, gH gene, gD gene, gK gene, gB gene, gN gene, UL5 gene, UL6 gene, UL8 Gene, UL9 gene, UL12 gene, UL25 gene, UL26 gene, UL28 gene, UL29 gene, UL30 gene, UL33 gene, UL36 gene, UL38 gene, UL42 gene, UL48 gene, UL52 gene, and any combination thereof.

In certain preferred embodiments, the mutated HSV genome comprises all other genes of the wild-type HSV virus, except for the two copies of the ICP0 gene and the two copies of the ICP34.5 gene as described above, and none of the other genes comprises a loss-of-function mutation. However, it is readily understood that a promoter of the other genes can be engineered (e.g., a native promoter can be substituted with a tumor-specific promoter, such as a promoter of hTERT), thereby further enhancing the safety of the recombinant HSV virus without affecting the functions/properties of the recombinant HSV virus of the invention. Thus, in certain preferred embodiments, the mutated HSV genome further comprises the following modification: a native promoter of one or more of HSV genes is substituted with a tumor-specific promoter, such as a promoter of hTERT. In certain preferred embodiments, the HSV gene is selected from the group consisting of VP5 gene, ICP27 gene, and ICP4 gene.

In certain preferred embodiments, the mutated HSV genome further comprises one or more modifications selected from the group consisting of:

(1) substitution of a native promoter of the VP5 gene with a tumor-specific promoter, such as a promoter of hTERT;

(2) substitution of a native promoter of the ICP27 gene with a tumor-specific promoter, such as a promoter of hTERT;

(3) substitution of a native promoter of the ICP4 gene with a tumor-specific promoter, such as a promoter of hTERT;

(4) deletion or mutation of one or more of the UL55 gene, the US2 gene, the LAT gene, and the nucleotide fragment corresponding to nt5853-nt7485 of JQ673480.1 (for example, comprising a loss-of-function mutation, or being substituted with an exogenous nucleotide sequence).

In certain preferred embodiments, the hTERT promoter has the sequence set forth in SEQ ID NO: 5.

In addition, the mutated HSV genome can also be modified to carry one or more exogenous nucleotide sequences. For example, in certain preferred embodiments, the mutated HSV genome further comprises a fifth exogenous nucleotide sequence. In certain preferred embodiments, the fifth exogenous nucleotide sequence encodes a foreign protein selected from the group consisting of fluorescent protein, immunomodulatory polypeptide, cytokine, chemokine, antibody, and cytotoxic peptide.

Host Cell

In another aspect, the invention provides a host cell, which is infected with a recombinant HSV virus according to the invention, or comprises the genome of the recombinant HSV virus according to the invention, or is transfected with a viral vector according to the invention. Such host cell includes, but is not limited to, prokaryotic cell such as *E. coli* cell, and eukaryotic cell such as yeast cell, insect cell, plant cell, and animal cell (e.g., mammalian cell, such as mouse cell, human cell, etc.). The recombinant HSV virus of the present invention has high replication ability in a tumor cell, but only replicates at a low level in a normal cell. Thus, in certain particularly preferred embodiments, the cell is a tumor cell. Such tumor cell includes, but is not limited to, lung cancer cell (e.g., H1299, H520, H1975, NCI-H358, and A549); liver cancer cell (e.g., Huh7, Hep3B, HepG2, GSG7701, SMMC7721, Hepal-6, BEL7404, PLC/PRF and QGY7703); breast cancer cell (e.g., MADMB231, MCF7 and MADMB468); osteosarcoma cell (e.g., U2OS and SAOS2); ovarian cancer cell (e.g., SKOV3 and CAOV3); cervical cancer cell (e.g., SiHA and Hela); prostate cancer cell (e.g., PC-3); glioma cell (e.g., U87MG); melanoma cells (e.g., A375); colorectal cancer cell (e.g., HCT116) and pancreatic cancer cell (e.g., Panc-1).

Preparation

In another aspect, the invention relates to a method of preparing a recombinant HSV virus of the invention, comprising:

(1) cultivating a host cell according to the present invention;

(2) collecting and lysing the host cell after the host cell has undergone a lesion, to obtain a lysate of the host cell; and (3) recovering the recombinant HSV virus of the present invention from the lysate.

Pharmaceutical Composition

In another aspect, the invention relates to a pharmaceutical composition comprising the recombinant HSV virus according to the invention, or the genome of the recombinant HSV virus according to the invention, or the viral vector according to the invention, and a pharmaceutically acceptable carrier or excipient. The pharmaceutical composition of the present invention can be used for treatment of a tumor, such as lung cancer, liver cancer, breast cancer, osteosarcoma, ovarian cancer, prostate cancer, glioma, melanoma, colorectal cancer, and pancreatic cancer.

The pharmaceutical composition of the invention may be administered by methods well known in the art such as, but not limited to, administration by injection. In certain preferred embodiments, the pharmaceutical composition of the invention is administered by injection (e.g., intratumoral injection). In certain preferred embodiments, the pharmaceutical composition of the invention is an injectable solution or a lyophilized powder.

In certain preferred embodiments, the recombinant HSV virus or the genome of the recombinant HSV virus or the viral vector is present in a therapeutically effective amount (e.g., an amount therapeutically effective in tumor treatment). In certain preferred embodiments, the pharmaceutical composition of the invention is presented in a unit dosage form. For example, but not intended to limit the invention, the amount of the recombinant HSV virus comprised in per unit dose of the pharmaceutical composition may be $10^2$-$10^9$ pfu, such as $10^2$-$10^3$ pfu, $10^3$-$10^4$ pfu, $10^4$-$10^5$ pfu, $10^5$-$10^6$ pfu, $10^6$-$10^7$ pfu, $10^7$-$10^8$ pfu, or $10^8$-$10^9$ pfu.

Use/Method of Use

The recombinant HSV virus of the present invention can be used in treatment of various tumors. Accordingly, in another aspect, the present invention relates to a method of treating a tumor, comprising administering to a subject in need thereof a therapeutically effective amount of the recombinant HSV virus of the invention or the viral vector of the invention or the pharmaceutical composition of the invention. In certain preferred embodiments, the tumor includes, but is not limited to, lung cancer, liver cancer, breast cancer, osteosarcoma, ovarian cancer, prostate cancer, glioma, melanoma, colorectal cancer, and pancreatic cancer. In certain preferred embodiments, the subject is a mammal, such as a human. In certain preferred embodiments, the recombinant HSV virus of the invention or the viral vector of the invention or the pharmaceutical composition of the invention is administered to the subject by injection (e.g., intratumoral injection).

In another aspect, the invention relates to a use of the recombinant HSV virus of the invention or the viral vector of the invention in manufacture of a pharmaceutical composition for treating a tumor in a subject. In certain preferred embodiments, the tumor includes, but is not limited to, lung cancer, liver cancer, breast cancer, osteosarcoma, ovarian cancer, prostate cancer, glioma, melanoma, colorectal cancer, and pancreatic cancer. In certain preferred embodiments, the subject is a mammal, such as a human. In certain preferred embodiments, the pharmaceutical composition is administered by injection (e.g., intratumoral injection). In certain preferred embodiments, the pharmaceutical composition is an injectable solution or a lyophilized powder.

Advantageous Effects of the Invention

Compared with the recombinant herpes simplex viruses of the prior art, the recombinant HSV virus of the present invention has the following beneficial technical effects: the recombinant HSV virus of the present invention has a high level of replication ability in tumor cells, and is capable of effectively killing various tumor cells, but has a significantly reduced level of replication and killing ability in normal cells. Furthermore, it has also been shown that the recombinant HSV virus of the invention has a significantly reduced level of neurotoxicity in animals and can be administered to an animal at a significantly increased dose. Therefore, compared with the existing recombinant HSV viruses, the recombinant HSV virus of the present invention not only maintains a high level of oncolytic ability, but also has a significantly improved level of safety, thus can be administered at a higher dose, and has broad application prospects.

Description of Sequence Information

Information on the sequences involved in the present invention is provided in Table 1.

TABLE 1

| SEQ ID NO: | Sequence information Description |
|---|---|
| 1 | GenBank: nt33 to nt5876 or JQ673480.1 |
| 2 | Gene sequence of LacZ |
| 3 | GenBank: nt112861 to nt113422 of JQ673480.1 |
| 4 | GenBank: nt113590 to nt115194 of JQ673480.1 |
| 5 | hTERT core promotor sequence |
| 6 | GenBank: nt510 (125731) to nt5439 (120802) of JQ673480.1 |
| 7 | Amino acid sequence of GFP |
| 8 | Amino acid sequence of PD-1 scFv |
| 9-16 | Primer sequences |
| 17 | GenBank: nt91088-nt92557 of JQ673480.1 |
| 18 | GenBank: nt94721-nt95968 of JQ673480.1 |
| 19 | GenBank: nt103527-nt104999 of JQ673480.1 |
| 20 | GenBank: nt115418-nt115978 of JQ673480.1 |

TABLE 1-continued

| | |
|---|---|
| 21 | GenBank: nt133911-nt134786 of JQ673480.1 |
| 22 | GenBank: nt4781-nt7062 of JQ673480.1 |
| 23 | GenBank: nt5853-nt7485 of JQ673480.1 |

```
SEQ ID NO: 1
GCAAAAAAGGCGGGCGGCGGTCCGGGCGGCGTGCGCGCGCGGCGGGCGTGGGGGCGGGC
CGCGGGAGCGGGGGAGGAGCGGGGGAGGAGCGGGGGGAGGAGCGGGGGGAGGAGCGGGGGA
GGAGCGGGGGAGGAGCGGGGGAGGAGCGGGGGAGGAGCGGGGGAGGAGCGGGGGAGG
AGCGGGGGAGGAGCGGGGGAGGAGCGGGGGAGGAGCGGGGGAGGAGCGGGGGAGGAG
CGGGGGAGGAGCGGGGGAGGAGCGGGGGAGGAGCGGCCAGACCCCGGAAACGGGCCCCCC
CAAAACACACCCCCGGGGGTCGCGCGCGGCCCTTTAAAGGCGGGCGGCGGGCAGCCCGGGCC
CCCGCGGCCGAGACTAGCGAGTTAGACAGGCAAGCACTACTCGCCTCTGCACGCACATGCTTGCC
TGTCAAACTCTACCACCCCGGCACGCTCTCTGTCTCCATGGCCCGCCGCCGCCATCGCGGCCCCG
CCGCCCCCGGCCGCCCGGGCCCACGGGCGCGGTCCCAACCGCACAGTCCCAGGTAACCTCCACGC
CCAACTCGGAACCCGTGGTCAGGAGCGCGCCCGCGGCCGCCCGCGCCGCCCCCGCAGTGGG
CCCCCGCCTTCTTGTTCGCTGCTGCTGCGCCAGTGGCTCCACGTTCCCGAGTCCGCGTCCGACGAC
GACGACGACGACTGGCCGGACAGCCCCCCGCCCGAGCCGGCGCCAGAGGCCCGGCCCACCGCCG
CCGCCCCCGCCCCGGTCCCACCGCCCGGCGCGGGCCCGGGGGCGGGGCTAACCCCTCCCAC
CCCCCCTCACGCCCCTTCCGCCTTCCGCGCGCCTCGCCCTCCGCCTGCGCGTCACGCAGAGCAC
CTGGCGCGCCTGCGCCTGCGACGCGCGGGCGGGAGGGGGCGCCGAAGCCCCCCGCGACCCCCG
CGACCCCCGCGACCCCCACGCGGGTGCGCTTCTCGCCCCACGTCCGGGTGCGCCACCTGGTGGTC
TGGGCCTCGGCCGCCCGCCTGGCGCGCCGCGGCTCGTGGGCCCGCGAGCGGGCCGACCGGGCTCG
GTTCCGGCGCCGGGTGGCGGAGGCCGAGGCGGTCATCGGGCCGTGCCTGGGGCCCGAGGCCCGT
GCCCGGGCCCTGGCCCGCGGAGCCGGCCCGGCGAACTCGGTCTAACGTTACACCCGAGGCGGCCT
GGGTCTTCCGCGGAGCTCCCGGGAGCTCCGCACCAAGCCGCTCTCCGGAGAGACGATGGCAGGA
GCCGCGCATATATACGCTTGGAGCCGGCCCGCCCCCGAGGCGGGCCCGCCCTCGGAGGGCGGGA
CTGGCCAATCGGCGGCCGCCAGCGCGGCGGGGCCCGGCCAACCAGCGTCCGCGAGTCGTCGGG
GCCCGGCCCACTGGGCGGTAACTCCCGCCCAGTGGGCCGGGCCGCCCACTTCCCGGTATGGTAAT
TAAAAACTTGCAGAGGCCTTGTTCCGCTTCCCGGTATGGTAATTAGAAACTCATTAATGGGCGGC
CCCGGCCGCCCTTCCCGCTTCCGGCAATTCCCGCGGCCCTTAATGGGCAACCCCGGTATTCCCCGC
CTCCCGCGCGCGCGTAACCACTCCCCTGGGGTTCCGGGTTATGTTAATTGCTTTTTTTGGCGGAAC
ACACGGCCCTCGCGCATTGGCCGCGGGTCGCTCAATGAACCGCATTGGTCCCCTGGGGTTCC
GGGTATGGTAATGAGTTTCTTCGGGAAGGCGGGAAGCCCCGGGGCACCGACGCAGGCCAAGCCC
CTGTTGCGTCGGCGGGAGGGGCATGCTAATGGGGTTCTTTGGGGGACACCGGGTTGGTCCCCCAA
ATCGGGGGCCGGGCCGTGCATGCTAATGATATTCTTTGGGGGCGCCGGGTTGGTCCCCGGGGACG
GGGCCGCCCCGCGGTGGGCCTGCCTCCCCTGGGACGCGCGGCCATTGGGGGAATCGTCACTGCCG
CCCCTTTGGGGAGGGGAAAGGCGTGGGGTATAAGTTAGCCCTGGCCCGACGGTCTGGTCGCATTT
GCACCTCGGCACTCGGAGCGAGACGCAGCAGCCAGGCAGACTCGGGCCGCCCCCTCTCCGCATCA
CCACAGAAGCCCCGCCTACGTTGCGACCCCAGGGACCCTCCGTCAGCGACCCTCCAGCCGCATA
CGACCCCCATGGAGCCCCGCCCCGGAGCGAGTACCCGCCGGCCTGAGGGCCGCCCCCAGCGCGGA
GGTGAGGGGCCGGGCGCCATGTCTGGGGCGCCATGTTGGGGGCGCCATGTTGGGGGCGCCAT
GTTGGGGGACCCCCGACCCTTACACTGGAACCGGCCGCCATGTTGGGGGACCCCCACTCATACAC
GGGAGCCGGGCGCCATGTTGGGGCGCCATGTTAGGGGCGTGGAACCCCGTGACACTATATATAC
AGGGACCGGGGGCGCCATGTTAGGGGGCGCGGAACCCCCTGACCCTATATATACAGGGACCGGG
GTCGCCCTGTTAGGGGTCGCCATGTGACCCCCTGACTTTATATATACAGACCCCCAACACCTACAC
ATGGCCCCTTTGACTCAGACGCAGGGCCCGGGGTCGCCGTGGGACCCCCCTGACTCATACACAGA
GACACGCCCCCACAACAAACACACAGGGACCGGGGTCGCCGTGTTAGGGGGCGTGGTCCCCACT
GACTCATACGCAGGGCCCCCTTACTCACACGCATCTAGGGGGGGTGGGAGGAGCCGCCCGCCATA
TTTGGGGGACGCCGTGGGACCCCCGACTCCGGTGCGTCTGGAGGGCGGGAGAAGAGGGAAGAAG
AGGGGTCGGGATCCAAAGGACGGACCCAGACCACCTTTGGTTGCAGACCCCTTTCTCCCCCCTCTT
CCGAGGCCAGCAGGGGGCAGGACTTTGTGAGGCGGGGGGGGAGGGGGAACTCGTGGGCGCTGA
TTGACGCGGGAAATCCCCCCATTCTTACCCGCCCCCCTTTTTTCCCCTCAGCCCGCCCCGGATGT
CTGGGTGTTTCCCTGCGACCGAGACCTGCCGGACAGCAGCGACTCGGAGGCGGAGACCGAAGTG
GGGGGGCGGGGGACGCCGACCACCATGACGACGACTCCGCCTCCGAGGCGGACAGCACGGACA
CGGAACTGTTCGAGACGGGGCTGCTGGGGCCGCAGGGCGTGGATGGGGGGCGGTCTCGGGGGGG
GAGCCCCCCCGCGAGGAAGACCCCGGCAGTTGCGGGGGCGCCCCCCTCGAGAGGAGCGGGGGG
AGCGACGAGGGCGACGTGTGCGCCGTGTGCACGGATGAGATCGCGCCCCACCTGCGCTGCGACA
CCTTCCCGTGCATGCACCGCTTCTGCATCCCGTGCATGAAAACCTGGATGCAATTGCGCAACACCT
GCCCGCTGTGCAACGCCAAGCTGGTGTACCTGATAGTGGGCGTGACGCCCAGCGGGTCGTTCAGC
ACCATCCCGATCGTGAACGACCCCCAGACCCGGCATGGAGGCCGAGGAGGCCGTCAGGGCGGGCA
CGGCCGTGGACTTTATCTGGACGGGCAATCAGCGGTTCGCCCCGCCGGTACCTGACCCTGGGGGGG
CACACGGTGAGGGCCCTGTCGCCCACCCACCCTGAGCCCACCACGGACGAGGATGACGACGACCT
GGACGACGGTGAGGCGGGGGGGCGGCGAGGACCCTGGGGAGGAGGAGGAGGGGGGGGGAGG
GAGGAATAGGCGGGCGGCGGGCGAGGAAAGGGCGGGCCGGGAGGGGGCGTAACCTGATCGC
GCCCCCCGTTGTCTCTTGCAGCAGACTACGTACCGCCCGCCCCCCCGCCCGCCCCCCCC
CACGCAGAGGCGCCGCCGCGCCCCCCGTGACGGGCGGGGCGTCTCACGCAGCCCCCCAGCCGGC
CGCGGCTCGGACAGCGCCCCCCTCGGCGCCCATCGGGCCACACGGCAGCAGTAACACTAACACCA
CCACCAACAGCAGCGGCGGCGGCGGCTCCCGCCAGTCGCGAGCCGCGGTGCCGCGGGGGCGTC
TGGCCCCTCCGGGGGGTTGGGGTTGTTGAAGCGGAGGCGGGGCGCCGAGGGGCCGGGACGGGC
CCCCTTGTCAACAGACCCGCCCCCCTTGCAAACAACAGAGACCCCATAGTGATCAGCGACTCCCC
CCCGGCCTCTCCCCACAGGCCCCCGCGGCGCCCATGCCAGGCTCCGCCCCCGCCCCGGTCCCCC
CGCGTCCGCGGCCGCGTCGGGCCCCGCGCGCCCCGCGCGGCCGTGCCCCGTGTGTGCGGGCGC
CGCCTCCGGGGCCCGGCCCCGCCGCCCCCGCCCCGGGGCGGAGCCGGCCGCCGCCCCCGGGAC
GCGCGCCGTGTGCCCCAGTCGCACTCGTCCCTGGCTCAGGCCGCGAACCAAGAACAGAGTCTGTG
CCGGGCGCGTGCGACGGTGGCGCGCGGCTCGGGGGGCCGGGCGTGGAGGGTGGACACGGGCCC
TCCCGCGGCGCCGCCCCCTCCGGCGCCGCCCCCTCCGGCGCCCCCCGCTCCCTCCGCCGCCTCT
GTCGAGCAGGAGGCGGCGGTGCGTCCGAGGAAGAGGCGCGGGTCGGGCCAGGAAAACCCCTCCC
CCCAGTCCACGCGTCCCCCCCTCGCGCCGGCAGGGGCCAAGAGGGCGGCGACGCACCCCCCCTCC
```

TABLE 1-continued

```
GACTCAGGGCCGGGGGGCGCGGCCAGGGAGGGCCCGGGACCCCCCTGACGTCCTCGGCGGCCT
CCGCCTCTTCCTCCTCCGCCTCTTCCTCCTCGGCCCCGACTCCCGCGGGGGCCACCTCTTCCGCCAC
CGGGGCCGCGTCCTCCTCCGCTTCCGCCTCCTCGGGCGGGGCCGTCGGTGCCCTGGGAGGGAGAC
AAGAGGAAACCTCCCTCGGCCCCCGCGCTGCTTCTGGGCCGCGGGGGGCCGAGGAAGTGTGCCCGG
AAGACGCGCCACGCGGAGACTTCCGGGGCCGTCCCCGCGGGCGGCCTCACGCGCTACCTGCCCAT
CTCGGGGGTCTCTAGCGTGGTCGCCCTGTCGCCTTACGTGAACAAGACGATCACGGGGGACTGCC
TGCCCATCCTGGACATGGAGACGGGGAACATCGGGGCGTACGTGGTCCTGGTGGACCAGACGGG
AAACATGGCGACCCGGCTGCGGGCCGGTCCCCGGCTGGAGCCGCCGCACCCTGCTCCCCGAGA
CCGCGGGTAACCACGTGACGCCCCCGAGTACCCGACGGCCCCCGCGTCGGAGTGGAACAGCCTC
TGGATGACCCCCGTGGGGAACATGCTGTTCGACCAGGGCACCCTAGTGGGCGCCCTGGACTTCCG
CAGCCTGCGGTCTCGGCACCCGTGGTCCGGGGAGCAGGGGGCGTCGACCCGGGACGAGGGAAAA
CAATAAGGGACGCCCCCGTGTTTGTGGGGAGGGGGGGGTCGGGCGCTGGGTGGTCTCTGGCCGCG
CCCACTACACCAGCCAATCCGTGTCGGGGAGGTGGAAAGTGAAAGACACGGGCACCACACACCA
GCGGGTCTTTTGTGTTGGCCCTAATAAAAAAAACTCAGGGGATTTTTGCTGTCTGTTGGGAAATAA
AGGTTTACTTTTGTATCTTTTCCCTGTCTGTGTTGGATGTATCGCGGGGGTGCGTGGGAGTGGGGG
TGCGTGGGAGTGGGGGTGCGTGGGAGTGGGGGTGCGTGGGAGTGGGGGTGCGTGGGAGTGGGGG
TGCGTGGGAGTGGGGGTGCGTGGGAGTGGGGGTGCGTGGGAGTGGGGGTGCGTGGGAGTGGGGG
TGCCATGTTGGGCAGGCTCTGGTGTT

SEQ ID NO: 2
GTCGTTTTACAACGTCGTGACTGGGAAAACCCTGGCGTTACCCAACTTAATCGCCTTGCAGCACAT
CCCCCTTTCGCCAGCTGGCGTAATAGCGAAGAGGCCCGCACCGATCGCCCTTCCCAACAGTTGCG
CAGCCTGAATGGCGAATGGCGCTTTGCCTGGTTTCCGGCACCAGAAGCGGTGCCGGAAAGCTGGC
TGGAGTGCGATCTTCCTGAGGCCGATACTGTCGTCGTCCCCTCAAACTGGCAGATGCACGGTTAC
GATGCGCCCATCTACACCAACGTGACCTATCCCATTACGGTCAATCCGCCGTTTGTTCCCACGGAG
AATCCGACGGGTTGTTACTCGCTCACATTTAATGTTGATGAAAGCTGGCTACAGGAAGGCCAGAC
GCGAATTATTTTTGATGGCGTTAACTCGGCGTTTCATCTGTGGTGCAACGGGCGCTGGGTCGGTTA
CGGCCAGGACAGTCGTTTGCCGTCTGAATTTGACCTGAGCGCATTTTTACGCGCGGAGAAAACC
GCCTCGCGGTGATGGTGCTGCGCTGGAGTGACGGCAGTTATCTGGAAGATCAGGATATGTGGCGG
ATGAGCGGCATTTTCCGTGACGTCTCGTTGCTGCATAAACCGACTACACAAATCAGCGATTTCCAT
GTTGCCACTCGCTTTAATGATGATTTCAGCCGCGCTGTACTGGAGGCTGAAGTTCAGATGTGCGGC
GAGTTGCGTGACTACCTACGGGTAACAGTTTCTTTATGGCAGGGTGAAACGCAGGTCGCCAGCGG
CACCGCGCCTTTCGGCGGTGAAATTATCGATGAGCGTGGTGGTTATGCCGATCGCGTCACACTAC
GTCTGAACGTCGAAAACCCGAAACTGTGGAGCGCCGAAATCCCGAATCTCTATCGTGCGGTGGTT
GAACTGCACACCGCCGACGGCACGCTGATTGAAGCAGAAGCCTGCGATGTCGGTTTCCGCGAGGT
GCGGATTGAAAATGGTCTGCTGCTGCTGAACGGCAAGCCGTTGCTGATTCGAGGCGTTAACCGTC
ACGAGCATCATCCTCTGCATGGTCAGGTCATGGATGAGCAGACGATGGTGCAGGATATCCTGCTG
ATGAAGCAGAACAACTTTAACGCCGTGCGCTGTTCGCATTATCCGAACCATCCGCTGTGGTACAC
GCTGTGCGACCGCTACGGCCTGTATGTGGTGGATGAAGCCAATATTGAAACCCACGGCATGGTGC
CAATGAATCGTCTGACCGATGATCCGCGCTGGCTACCGGCGATGAGCGAACGCGTAACGCGAATG
GTGCAGCGCGATCGTAATCACCCGAGTGTGATCATCTGGTCGCTGGGGAATGAATCAGGCCACGG
CGCTAATCACGACGCGCTGTATCGCTGGATCAAATCTGTCGATCCTTCCCGCCCGGTGCAGTATGA
AGGCGGCGGAGCCGACACCACGGCCACCGATATTATTTGCCCGATGTACGCGCGCGTGGATGAAG
ACCAGCCCTTCCCGGCTGTGCCGAAATGGTCCATCAAAAAATGGCTTTCGCTACCTGGAGAGACG
CGCCCGCTGATCCTTTGCGAATACGCCCACGCGATGGGTAACAGTCTTGGCGGTTTCGCTAAATAC
TGGCAGGCGTTTCGTCAGTATCCCCGTTTACAGGGCGGCTTCGTCTGGGACTGGGTGGATCAGTCG
CTGATTAAATATGATGAAAACGGCAACCCGTGGTCGGCTTACGGCGGTGATTTTGGCGATACGCC
GAACGATCGCCAGTTCTGTATGAACGGTCTGGTCTTTGCCGACCGCACGCCGCATCCAGCGCTGA
CGGAAGCAAAACACCAGCAGCAGTTTTTCCAGTTCCGTTTATCCGGGCAAACCATCGAAGTGACC
AGCGAATACCTGTTCCGTCATAGCGATAACGAGCTCCTGCACTGGATGGTGGCGCTGGATGGTAA
GCCGCTGGCAAGCGGTGAAGTGCCTCTGGATGTCGCTCCACAAGGTAAACAGTTGATTGAACTGC
CTGAACTACCGCAGCCGGAGAGCGCCGGGCAACTCTGGCTCACAGTACGCGTAGTGCAACCGAA
CGCGACCGCATGGTCAGAAGCCGGGCACATCAGCGCCTGGCAGCAGTGGCGTCTGGCGGAAAAC
CTCAGTGTGACGCTCCCCGCCGCGTCCCACGCCATCCCGCATCTGACCACCAGCGAAATGGATTTT
TGCATCGAGCTGGGTAATAAGCGTTGGCAATTTAACCGCCAGTCAGGCTTTCTTTCACAGATGTGG
ATTGGCGATAAAAAACAACTGCTGACGCCGCTGCGCGATCAGTTCACCCGTGCACCGCTGGATAA
CGACATTGGCGTAAGTGAAGCGACCCGCATTGACCCTAACGCCTGGGTCGAACGCTGGAAGGCG
GCGGGCCATTACCAGGCCGAAAGCAGCGTTGTTGCAGTGCACGGCAGATACACTTGCTGATGCGG
TGCTGATTACGACCGCTCACGCGTGGCAGCATCAGGGGAAAACCTTATTTATCAGCCGGAAAACC
TACCGGATTGATGGTAGTGGTCAAATGGCGATTACCGTTGATGTTGAAGTGGCGAGCGATACACC
GCATCCGGCGCGGATTGGCCTGAACTGCCAGCTGGCGCAGGTAGCAGAGCGGGTAAACTGGCTC
GGATTAGGGCCGCAAGAAAACTATCCGACCGCCTTACTGCCGCCTGTTTTGACCTGGGATCT
GCCATTGTCAGACATGTATACCCCGTACGTCTTCCCGAGCGAAAACGGTCTGCGCTGCGGGACGC
GCGAATTGAATTATGGCCCACACCAGTGGCGCGGCGACTTCCAGTTCAACATCAGCCGCTACAGT
CAACAGCAACTGATGGAAACCAGCCATCGCCATCTGCTGCACGCGGAAGAAGGCACATGGCTGA
ATATCGACGGTTTCCATATGGGGATTGGTGGCGACGACTCCTGGAGCCCGTCAGTATCGGCGGAA
TTCCAGCTGAGCGCCGGTCGCTACCATTACCAGTTGGTCTGGTGTCAAAAATAA

SEQ ID NO: 3
CCACCTGGTGTTTTGTCTCCACCATCGGCCTGACAGAGCTGTATTGTATTCTGCGGCGGGGCCCGG
CCCCCAAGAACGCAGACAAGGCCGCCGCCCCGGGGCGATCCAAGGGGCTGTCGGCGTCTGCGG
GCGCTGTTGTTCCATCATCCTGTCGGGCATCGCAATGCGATTGTTTATATCGCCGTGGTGGCCGG
GGTGGTGCTCGTGGCGCTTCACTACGAGCAGGAGATCCAGAGGCGCCTGTTTGATGTATGACGTC
ACATCCAGGCCGGCGGAAACCGGAACGGCATATGCAAACTGGAAACTGTCCTGTCTTGGGCCCA
CCCACCCGACGCGTCATATGTAAATGAAAATCGTTCCCCGAGGCCATGTGTAGCCTGGATCCCA
ACGACCCCGCCCATGGGTCCCAATTGGCCGTCCCGTTACCAAGACCAACCCAGCCAGCGTATCCA
CCCCCGCCCGGGTCCCCGCGGAAGCGGAACGTGTATGTGATATGCTAATTAAATACATGCCACG
TACTTATGGTGTCTGATTGGTCCTTGTCTGTGCCGGAGGTG
```

TABLE 1-continued

SEQ ID NO: 4
ACCGGTGCGCCACCACCAGAGGCCATATCCGACACCCCAGCCCCGACGGCAGCCGACAGCCCGG
TCATGGCGACTGACATTGATATGCTAATTGACCTCGGCCTGGACCTCTCCGACAGCGATCTGGAC
GAGGACCCCCCCGAGCCGGCGGAGAGCCGCCGCGACGACCTGGAATCGGACAGCAACGGGGAGT
GTTCCTCGTCGGACGAGGACATGGAAGACCCCCACGGAGAGGACGGACCGGAGCCGATACTCGA
CGCCGCTCGCCCGGCGGTCCGCCCGTCTCGTCCAGAAGACCCCGGCGTACCCAGCACCCAGACGC
CTCGTCCGACGGAGCGGCAGGGCCCCAACGATCCTCAACCAGCGCCCCACAGTGTGTGGTCGCGC
CTCGGGCCCGGCGACCGTCTTGCTCCCCCGAGCGGCACGGGGGCAAGGTGGCCCGGCCTCCAACC
CCCACCGACCAAAGCCCAGCCTGCCCGCGGCGGACGCCGTGGGCGTCGCAGGGGTCGGGGTCGC
GGTGGTCCCGGGGCCGCCGATGGTTTGTCGGACCCCCGCCGGCGTGCCCCCAGAACCAATCGCAA
CCCGGGGGGACCCCGCCCCGGGGCGGGGTGGACGGACGGCCCCGGCGCCCCCCATGCGCAGGCG
TGGCGCGGAAGTGAGCAGCCCGACCCACCCGGAGGCCCGCGGACACGGAGCGTGCGCCAAGCAC
CCCCCCCGCTAATGACGCTGGCGATTGCCCCCCCGCCCGCGGACCCCCGCGCCCCGGCCCCGGAG
CGAAAGGCGCCCGCCGCCGACACCATCGACGCCACCACGCGGTTGGTCCTGCGCTCCATCTCCGA
GCGCGCGGCGGTCGACCGCATCAGCGAGAGCTTCGGCCGCAGCGCACAGGTCATGCACGACCCCT
TTGGGGGGCAGCCGTTTCCCGCCGCGAATAGCCCCTGGGCCCCGGTGCTGGCGGGCCAAGGAGGG
CCCTTTGACGCCGAGACCAGACGGGTCTCCTGGGAAACCTTGGTCGCCCACGGCCCGAGCCTCTA
TCGCACTTTTGCCGGCAATCCTCGGGCCGCATCGACCGCAAGGCCATGCGCGACTGCGTGCTGC
GCCAAGAAAATTTCATCGAGGCGCTGGCCTCCGCCGACGAGACGCTGGCGTGGTGCAAGATGTGC
ATCACCACAACCTGCGCTGCGCCCCCAGGACCCCATTATCGGGACGGCCGCGGCGGTGCTGGA
TAACCTCGCCACGCGCCTGCGGCCCTTTCTCCAGTGCTACCTGAAGGCGCGAGGCCTGTGCGGCCT
GGACGAACTGTGTTCGCGGCGGCGTCTGGCGGACATTAAGGACATTGCATCCTTCGTGTTTGTCAT
TCTGGCCAGGCTCGCCAACCGCGTCGAGCGTGGCGTCGCGGAGATCGACTACGCGACCCTTGGTG
TCGGGGTCGGAGAGAAGATGCATTTCTACCTCCCGGGGCCTGCATGGCGGGCCTGATCGAAATC
CTAGACACGCACCGCCAGGAGTGTTCGAGTCGTGTCTGCGAGTTGACGGCCAGTCACATCGTCGC
CCCCCCGTACGTGCACGGCAAATATTTTTATTGCAACTCCCTGTTTTAG

SEQ ID NO: 5
CTGCGCTGTCGGGGCCAGGCCGGGCTCCCAGTGGATTCGCGGGCACAGACGCCCAGGACCGCGCT
TCCCACGTGGCGGAGGGACTGGGGACCCGGGCACCCGTCCTGCCCCTTCACCTTCCAGCTCCGCC
TCCTCCGCGCGGACCCCGCCCCGTCCCGACCCCTCCCGGGTCCCCGGCCCAGCCCCCTCCGGGCCC
TCCCAGCCCCTCCCCTTCCTTTCCGCGGCCCCGCCCTCTCCTCGCGGCGCGAGTTTCAGGCAGC

SEQ ID NO: 6
CATGGCCCGCCGCCGCCATCGCGGCCCCCGCCGCCCCGGCCGCCCGGGCCCACGGGCGCGGTCC
CAACCGCACAGTCCCAGGTAACCTCCACGCCCAACTCGGAACCCGTGGTCAGGAGCGCGCCCGCG
GCCGCCCCGCCGCCGCCCCCCGCCAGTGGGCCCCGCCTTCTTGTTCGCTGCTGCTGCGCCAGTGG
CTCCACGTTCCCGAGTCCGCGTCCGACGACGACGACGACGACTGGCCGGACAGCCCCCCGCCCGA
GCCGGCGCCAGAGGCCCGGCCCACCGCCGCCGCCCCCGCCCCCGGTCCCCACCGCCCGGCGCGG
GCCCGGGGGCGGGGCTAACCCCTCCCACCCCCCCTCACGCCCCTTCCGCCTTCCGCCGCGCCTCG
CCCTCCGCCTGCGCGTCACCGCAGAGCACCTGGCGCGCCTGCGCCTGCGACGCGCGGGCGGGGAG
GGGGCGCCGAAGCCCCCGCGACCCCCGCGACCCCCGCGACCCCCACGCGGGTGCGCTTCTCGCC
CCACGTCCGGGTGCGCCACCTGGTGGTCTGGGCCTCGGCCGCCCGCCTGGCGCGCCGCGGCTCGT
GGGCCCGCGAGCGGGCCGACCGGGCTCGGTTCCGGCGCCGGGTGGCGGAGGCCGAGGCGGTCAT
CGGGCCGTGCCTGGGGCCCGAGGCCCGTGCCCGGGCCCTGGCCCTGCTGCGGCCGGCCGGCGAAC
TCGGTCTAACGTTACACCCGAGGCGGCCTGGGTCTTCCGCGGAGCTCCCGGGAGCTCCGCACCAA
GCCGCTCTCCGGAGAGACGATGGCAGGAGCCGCGCATATATACGCTTGGAGCCGGCCCGCCCCCG
AGGCGGGCCCGCCCTCGGAGGGCGGGACTGGCCAATCGGCGGCCGCCAGCGCGGCGGGGCCCGG
CCAACCAGCGTCCGCCGAGTCGTCGGGGCCCGGCCCACTGGGCGGTAACTCCCGCCCAGTGGGCC
GGGCCGCCCACTTCCCGGTATGGTAATTAAAAAACTTGCAGAGGCCTTGTTCCGCTTCCCGGTATGG
TAATTAGAAACTCATTAATGGGCGGCCCCGGCCGCCCTTCCCGCTTCCGGCAATTCCCGCGGCCCT
TAATGGGCAACCCCGGTATTCCCCGCCTCCCGCGCCGCGTAACCACTCCCCTGGGGTTCCGGGT
TATGTTAATTGCTTTTTTGGCGGAACACACGGCCCCTCGCGCATTGGCCCGCGGTTCGCTCAATGA
ACCCGCATTGGTCCCCTGGGGTTCCGGGTATGGTAATGAGTTTCTTCGGGAAGGCGGGAAGCCCC
GGGGCACCGACGCAGGCCAAGCCCCTGTTGCGTCGGCGGGAGGGGCATGCTAATGGGGTTCTTTG
GGGGACACCGGGTTGGTCCCCCAAATCGGGGGCCGGGCCGTGCATGCTAATGATATTCTTTGGGG
GCGCCGGGTTGGTCCCCGGGGACGGGGCCGCCCCGCGGTGGGCCTGCCTCCCCTGGGACGCGCGG
CCATTGGGGGAATCGTCACTGCCGCCCCTTTGGGGAGGGGAAAGGCGTGGGGTATAAGTTAGCCC
TGGCCCGACGGTCTGGTCGCATTTGCACCTCGGCACTCGGAGCGAGACGCAGCAGCCAGGCAGAC
TCGGGCCGCCCCCTCTCCGCATCACCACAGAAGCCCCGCCTACGTTGCGACCCCCAGGGACCCTC
CGTCAGCGACCCTCCAGCCGCATACGACCCCCATGGAGCCCCGCCCCCGGAGCGAGTACCCGCCGG
CCTGAGGGCCGCCCCCAGCGCGAGGTGAGGGGCCGGGCGCCATGTCTGGGGCGCCATGTTGGGG
GGCGCCATGTTGGGGGGCGCCATGTTGGGGGACCCCCGACCCTTACACTGGAACCGGCCGCCATG
TTGGGGGACCCCCACTCATACACGGGAGCCGGGCGCCATGTTGGGCGCCATGTTAGGGGGCGTG
GAACCCCGTGACACTATATATACAGGGACCGGGGCGCCATGTTAGGGGCGCGGAACCCCCTG
ACCCTATATATACAGGGACCGGGGTCGCCCTGTTAGGGGTCGCCATGTGACCCCCTGACTTTATAT
ATACAGACCCCCAACACCTACACATGGCCCCTTTGACTCAGACGCAGGGCCCGGGGTCGCCGTGG
GACCCCCTGACTCATACACAGAGACACGCCCCCACAACAAACACAGGGACCGGGGTCGCCG
TGTTAGGGGCGTGGTCCCCACTGACTCATACGCAGGGCCCCCTTACTCACACGCATCTAGGGGG
GTGGGGAGGAGCCGCCCGCCATATTTGGGGACGCCGTGGGACCCCCGACTCCGGTGCGTCTGGA
GGGCGGGAGAAGAGGGAAGAAGAGGGGTCGGGATCCAAAGGACGGACCCAGACCACCTTTGGTT
GCAGACCCCTTTCTCCCCCTCTTCCGAGGCCAGCAGGGGGGCAGGACTTTGTGAGGCGGGGGGG
GAGGGGGAACTCGTGGGCGCTGATTGACGCGGGAAATCCCCCCATTCTTACCCGCCCCCCCTTTTT
TCCCCTCAGCCGCCCCGGATGTCTGGGTGTTTCCCTGCGACGAGACCTGCCGGACAGCAGCGA
CTCGGAGGCGGAGACCGAAGTGGGGGGGCGGGGGGACGCCGACCACCATGACGACGACTCCGCC
TCCGAGGCGGACAGCACGGACACGGAACTGTTCGAGACGGGGCTGCTGGGGCCGCAGGGCGTGG
ATGGGGGGCGGTCTCGGGGGGAGCCCCCCCGCGAGGAAGACCCCGGCAGTTGCGGGGCGC
CCCCCCTCGAGAGGACGGGGGAGCGACGAGGGCGACGTGTGCGCCGTGTGCACGGATGAGATC
GCGCCCCACCTGCGCTGCGACACCTTCCCGTGCATGCACCGCTTCTGCATCCCGTGCATGAAAACC

TABLE 1-continued

```
TGGATGCAATTGCGCAACACCTGCCCGCTGTGCAACGCCAAGCTGGTGTACCTGATAGTGGGCGT
GACGCCCAGCGGGTCGTTCAGCACCATCCCGATCGTGAACGACCCCCAGACCCGCATGGAGGCCG
AGGAGGCCGTCAGGGCGGGCACGGCCGTGGACTTTATCTGGACGGGCAATCAGCGGTTCGCCCCG
CGGTACCTGACCCTGGGGGGGCACACGGTGAGGGCCCTGTCGCCCACCCACCCTGAGCCCACCAC
GGACGAGGATGACGACGACCTGGACGACGGTGAGGCGGGGGGGCGGCGAGGACCCTGGGGGAG
GAGGAGGAGGGGGGGGGGAGGGAGGAGGAATAGGCGGGCGGGCGGGCGAGGAAAGGGCGGGCCGG
GGAGGGGGCGTAACCTGATCGCGCCCCCGTTGTCTCTTGCAGCAGACTACGTACCGCCCGCCCC
CCGCCGGACGCCCGCGCCCCCCACGCAGAGGCGCCGCCGCCCCCGTGACGGGCGGGGCG
TCTCACGCAGCCCCCCAGCCGGCCGCGGCTCGGACAGCGCCCCCCTCGGCGCCCATCGGGCCACA
CGGCAGCAGTAACACTAACACCACCACCAACAGCAGCGGCGGCGGCGGCTCCCGCCAGTCGCGA
GCCGCGGTGCCGCGGGGGGCGTCTGGCCCCTCCGGGGGGGTTGGGGTTGTTGAAGCGGAGGCGG
GGCGGCCGAGGGGCCGGACGGGCCCCCTTGTCAACAGACCCGCCCCCCTTGCAAACAACAGAGA
CCCCATAGTGATCAGCGACTCCCCCCCGGCCTCTCCCCACAGGCCCCCCGCGGCGCCCATGCCAG
GCTCCGCCCCCGCCCCGGTCCCCCGCGTCCGCGGCCGCGTCGGGCCCCGCGCGCCCCCGCGCG
GCCGTGGCCCCGTGTGTGCGGGCGCCGCCTCCGGGGCCCGGCCCCGCGCCCCGGCCCCGGGGC
GGAGCCGGCCGCCCGCCCCGCGGACGCGCGCCGTGTGCCCCAGTCGCACTCGTCCCTGGCTCAGG
CCGCGAACCAAGAACAGAGTCTGTGCCGGGCGCGTGCGACGGTGGCGCGGCTCGGGGGGCG
GGGCGTGGAGGGTGGACACGGGCCCTCCCGCGGCGCCGCCCCCTCCGGCGCCGCCCCCTCCGGCG
CCCCCCCGCTCCCCTCCGCCGCCTCTGTCGAGCAGGAGGCGGCGGTGCGTCCGAGGAAGAGGCGC
GGGTCGGGCCAGGAAAACCCCTCCCCCAGTCCACGCGTCCCCCCTCGCGCCGGCAGGGGCCAA
GAGGGCGGCGACGCACCCCCCTCCGACTCAGGGCCGGGGGCGCGCCCAGGAGGGCCCGGG
ACCCCCCTGACGTCCTCGGCGGCCTCCGCCTCTTCCTCCTCCGCCTCTTCCTCCTCGGCCCCGACTC
CCGCGGGGGCCACCTCTTCCGCCACCGGGGCCGCGTCCTCCTCCGCTTCCGCCTCCTCGGGCGGGG
CCGTCGGTGCCCTGGGAGGGAGACAAGAGGAAACCTCCCTCGGCCCCCGCGCTGCTTCTGGGCCG
CGGGGGCCGAGGAAGTGTGCCCGGAAGACGCGCCACGCGGAGACTTCCGGGGCCGTCCCCGCGG
GCGGCCTCACGCGCTACCTGCCCATCTCGGGGGTCTCTAGCGTGGTCGCCCTGTCGCCTTACGTGA
ACAAGACGATCACGGGGGACTGCCTGCCCATCCTGGACATGGAGACGGGGAACATCGGGGCGTA
CGTGGTCCTGGTGGACCAGACGGGAAACATGGCGACCCGGCTGCGGGCCGCGGTCCCCGGCTGG
AGCCGCCGCACCCTGCTCCCCGAGACCGCGGGTAACCACGTGACGCCCCCCGAGTACCCGACGGC
CCCCGCGTCGGAGTGGAACAGCCTCTGGATGACCCCCGTGGGGAACATGCTGTTCGACCAGGGCA
CCCTAGTGGGCGCCCTGGACTTCCGCAGCTGCGGTCTCGGCACCCGTGGTCCGGGGAGCAGGGG
GC

SEQ ID NO: 7
MVSKGEELFTGVVPILVELDGDVNGHKFSVSGEGEGDATYGKLTLKFICTTGKLPVPWPTLVTTLTYG
VQCFSRYPDHMKQHDFFKSAMPEGYVQERTIFFKDDGNYKTRAEVKFEGDTLVNRIELKGIDFKEDG
NILGHKLEYNYNSHNVYIMADKQKNGIKVNFKIRHNIEDGSVQLADHYQQNTPIGDGPVLLPDNHYLS
TQSALSKDPNEKRDHMVLLEFVTAAGITLGMDELYK

SEQ ID NO: 8
DVLMTQTPLFLPVSLGDQASIFCRSSQNIVHINGNTYLEWYLQKPGQFPKLLMYKVSNRFFGVPDRFS
GSGSGTDFTLKISRVEAEDLGVYYCFQGSHVPWTFGGGTKLEIKGGGGSGGGGSGGGGSGGGGSDV
QVQESGPGLVKPSQSLSLTCTVTGSSITSDFAWEWIRQFPGNKLECMGYIGYSGGTIYNPSLKSRISITR
DTSKNQFFLQLNSVTTEDTATYYCARWHGSSHWYFDVWGAGTTVTVSS

SEQ ID NO: 17
CTACTCGTCCCAGAATTTGGCCAGGACGTCCTTGTAGAACGCGGGTGGGGGGGCCTGGGTCCGCA
GCTGCTCCAGAAACCTGTCGGCGATATCAGGGGCCGTGATATGCCGGGTCACAATAGATCGCGCC
AGGTTTTCGTCGCGGATGTCCTGGTAGATAGGCAGGCGTTTCAGAAGAGTCCACGGCCCCCGCTC
CTTGGGGCCGATAAGCGATATGACGTACTTAATGTAGCGGTTCCACCAGCTCGGTGATGGTCA
TGGGATCGGGGAGCCAGTCCAGGGACTCTGGGGCGTCGTGGATGACGTGGCGTCGCCGGCTGGCC
ACATAACTGCGGTGCTCTTCCAGCAGCTGCGCGTTCGGGACCTGGACGAGCTCGGGCGGGGTGAG
TATCTCCGAGGAGGACGACCTGGGGCCGGGGTGGCCCCCGGTAACGTCCCGGGGATCCAGGGGG
AGGTCCTCGTCGTCTTCGTATCCGCCGGCGATCTGTTGGGTTAGAATTTCGGTCCACGAGACGCGC
ATCTCGGTGCCGCCGGCGGCCGGCGGCAAAGGGGGCCTGGTTTCCGTGGAGCGCGAGCTGGTGTG
TTCCCGGCGGATGGCCCGCCGGGTCTGAGAGCGACTCGGGGGGGTCCAGTGACATTCGCGCAGCA
CATCCTCCACGGAGGCGTAGGTGTTATTGGGATGGAGGTCGGTGTGGCAGCGGACAAAGAGGGC
CAGGAACTGGGGGTAGCTCATCTTAAAGTACTTTAGTATATCGCGACAGTTGATCGTGGGAATGT
AGCAGGCGCTAATATCCAACACAATATCACAGCCCATCAACAGGAGGTCAGTGTCTGTGGTGTAC
ACGTACGCGACCGTGTTGGTGTGATAGAGGTTGGCGCAGGCATCGTCCGCCTCCAGCTGACCCGA
GTTAATGTAGGCGTACCCCAGGGCCCGGAGAACGCGAATACAGAACAGATGCGCCAGACGCAGG
GCCGGCTTCGAGGGCGCGGCGGACGGCAGCGCGGCTCCGGACCCGGCCGTCCCCCGGGTCCCCG
AGGCCAGAGAGGTGCCGCCGGCGCATGTTGGAAAAGGCAGAGCTGGGTCTGGAGTCGGTCGAT
GGGGGAAGGCGGTGGAGAGGCGTCCACGTCACTGGCCTCCTCGTCCGTCCGGCATTGGGCCGTCG
TGCGGGCCAGGATGGCCTTGGCTCCAAACACAACCGGCTCCATACAATTGACCCCGCGATCGGTA
ACGAAGATGGGGAAAAGGGACTTTTGGGTAAACACCTTTAATAAGCGACAGAGGCAGTGTAGCG
TAATGGCCTCGCGGTCGTAACTGGGGTATCGGCGCTGATATTTGACCACCAACGTGTACATGACG
TTCCACAGGTCCACGGCGATGGGGGTGAAGTACCCGGCCGGGGCCCCAAGGCCCTGGCGCTTGAC
CAGATGGTGTGTGTGGGCAAACTTCATCATCCCGAACAAACCCAT

SEQ ID NO: 18
ATGCTCCGCAACGACAGCCACCGGGCCGCGTCCCGGAGGACGGCCAGGGACGGGTCGACGACG
GACGGCCACACCTCGCGTGCGTGGGGGCCCTGGCGCGGGGTTCATGCATATCTGGCTTCAGGCC
GCCACGCTGGGTTTTGCGGGATCGGTCGTTATGTCGCGCGGGCCGTACGCGAATGCCGCGTCTGG
GCGTTCGCCGTCGGGTGCGCCGTGCTGGCGTTTATGCGCGCACCCCCTCCCCTCGCGCGGCCCAC
CGCGCGGATATACGCCTGGCTCAAACTGGCGGCCGGTGGAGCGCCCCTTGTTCTGTGGAGTCTCG
GGGAGCCCGGAACGCAGCCGGGGCCCCGGGCCCGGCCACCCAGTGCCTGGCGCTGGGCGCCGC
CTATGCGGCGCTCCTGGTGCTCGCCGATGACGTCTATCCGCTCTTTCTCCTCGCCCCGGGGCCCCT
GTTCGTCGGCACCCTGGGGATGGTCGTCGGCGGGCTGACGATCGGAGGCAGCGCGCGCTACTGGT
GGATCGGTGGGCCCGCCGCGGCCGCCTTGGCCGCGGCGGTGTTGGCGGGCCCGGGGGCGACCAC
```

TABLE 1-continued

CGCCAGGGACTGCTTCTCCAGGGCGTGCCCCGACCACCGCCGCGTCTGCGTCATCGTCGCAGGCG
AGTCTGTTTCCCGCCGCCCCCGGAGGACCCAGAGCGACCCGGGGACCCCGGGCCACCGTCCCCC
CCGACACCCCAACGATCCCAGGGGCCGCCGGCCGATGAGGTCGCACCGGCCGGGGTAGCGCGGC
CCGAAAACGTCTGGGTGCCCGTGGTCACCTTTCTGGGGGCGGGCGCGCTCGCCGTCAAGACGGTG
CGAGAACATGCCCGGGAAACGCCGGGCCCGGGCCTGCCGCTGTGGCCCCAGGTGTTTCTCGGAGG
CCATGTGGCGGTGGCCCTGACGGAGCTGTGTCAGGCGCTTATGCCCTGGGACCTTACGGACCCGC
TGCTGTTTGTTCACGCCGGACTGCAGGTCATCAACCTCGGGTTGGTGTTTCGGTTTTCCGAGGTTG
TCGTGTATGCGGCGCTAGGGGGTGCCGTGTGGATTTCGTTGGCGCAGGTGCTGGGGCTCCGGCGT
CGCCTGCACAGGAAGGACCCCGGGGACGGGGCCCGGTTGGCGGCGACGCTTCGGGGCCTCTTCTT
CTCCGTGTACGCGCTGGGGTTTGGGGTGGGGGCGCTGCTGTGCCCTCCGGGGTCAACGGGCGGGT
GGTCGGGCGATTGA

SEQ ID NO: 19
CTACCCACCGTACTCGTCAATTCCAAGGGCATCGGTAAACATCTGCTCAAACTCGAAGTCGGCCA
TATCCAGAGCGCCGTAGGGGGCGGAGTCGTGGGGGGTAAATCCCGGACCCGGGGAATCCCCGTC
CCCCAACATGTCCAGATCGAAATCGTCTAGCGCGTCGGCATGCGCCATCGCCACGTCCTCGCCGT
CTAAGTGGAGCTCGTCCCCCAGGCTGACATCGGTCGGGGGGGCCGTCGACAGTCTGCGCGTGTGT
CCCGCGGGGAGAAAGGACAGGCGCGGAGCCGCCAGCCCCGCCTCTTCGGGGGCGTCGTCGTCCG
GGAGATCGAGCAGGCCCTCGATGGTAGACCCGTAATTGTTTTTCGTACGCGCGCGGCTGTACGCG
TGTTCCCGCATGACCGCCTCGGAGGGCGAGGTCGTGAAGCTGGAATACGAGTCCAACTTCGCCCG
AATCAACACCATAAAGTACCCAGAGGCGCGGGCCTGGTTGCCATGCAGGGTGGGAGGGGTCGTC
AACGGCGCCCCTGGCTCCTCCGTAGCCGCGCTGCGCACCAGCGGGAGGTTAAGGTGCTCGCGAAT
GTGGTTTAGCTCCCGCAGCCGGCGGGCCTCGATTGGCACTCCCCGGACGGTGAGCGCTCCGTTGA
CGAACATGAAGGGCTGGAACAGACCCGCCAACTGACGCCAGCTCTCCAGGTCGCAACAGAGGCA
GTCAAACAGGTCGGGCGCATCATCTGCTCGGCGTACGCGGCCCATAGGATCTCGCGGGTCAAAA
ATAGATACAAATGCAAAAACAGAACACGCGCCAGACGAGCGGTCTCTCGGTAGTACCTGTCCGC
GATCGTGGCGCGCAGCATTTCTCCCAGGTCGCGATCGCGTCCGCGCATGTGCGCCTGGCGGTGCA
GCTGCCGGACGCTGGCGCGCAGGTACCGGTACAGGGCCGAGCAGAAGTTGGCCAACACGGTTCG
ATAGCTCTCCTCCCGCGCCCGTAGCTCGGCGTGGAAGAAACAGAGAGCGCTTCGTAGTAGAGCC
CGAGGCCGTCGCGGGTGGCCGGAAGCGTCGGGAAGGCCACGTCGCCGTGGGCGCGAATGTCGAT
TTGGGCGCGTTCGGGGACGTACGCGTCCCCCCATTCCACCACATCGCTGGGCAGCGTTGATAGGA
ATTTACACTCCCGGTACAGGTCGGCGTTGGTCGGTAACGCCGAAAACAAATCCTCGTTCCAGGTA
TCGAGCATGGTACATAGCGCGGGCCCGCGCTAAAGCCCAAGTCGTCGAGGAGACGGTTAAAGA
GGGCGGCGGGGGGGACGGGCATGGGCGGGAGGGCATGAGCTGGGCCTGGCTCAGGCGCCCCGT
TGCGTACAGCGGAGGGGCCGCCGGGGTGTTTTTGGGACCCCCGGCCGGGCGGGGGGTGGTGGC
GAAGCGCCGTCCGCGTCCATGTCGGCAAACAGCTCGTCGACCAAGAGGTCCAT

SEQ ID NO: 20
ATGACAGCGACCCCCTCACCAACCTGTTCTTACGGGCCCCGGACATAACCCACGTGGCCCCCCC
TTACTGCCTCAACGCCACCTGGCAGGCCGAAACGGCCATGCACACCAGCAAAACGGACTCCGCTT
GCGTGGCCGTGCGGAGTTACCTGGTCCGCGCCTCCTGTGAGACCAGCGGCACAATCCACTGCTTTT
TCTTTGCGGTATACAAGGACACCCACCATACCCCTCCGCTGATTACCGAGCTCCGCAACTTTGCGG
ACCTGGTTAACCACCCGCCGGTCCTACGCGAACTGGAGGATAAGCGCGGGGTGCGGCTGCGGTGT
GCGCGGCCGTTTAGCGTCGGGACGATTAAGGACGTCTCTGGGTCCGGCGCGTCCTCGGCGGGAGA
GTACACGATAAACGGGATCGTGTACCACTGCCACTGTCGGTATCCGTTCTCAAAAACATGCTGGA
TGGGGGCCTCCGCGGCCCTACAGCACCTGCGCTCCATCAGCTCCAGCGGCATGGCCGCCCGCGCG
GCAGAGCATCGACGCGTCAAGATTAAAATTAAGGCGTGA

SEQ ID NO: 21
CTACAGGGTGGTAACCGGATAGCAGATGTGAGGAAGTCTGGGCCGTTCGCCGCGAACGGCGATC
AGAGGGTCCGTTTCTTGCGGACCACGGCCCGGTGATGTGGGTTGCTCGTCTAAAATCTCGGGCAT
ACCCATACACGCACAACACGGACGCCGCACCGAATGGGACGTCGTAAGGGGGTGGGAGGTAGCT
GGGTGGGGTTTGTGCAGAGCAATCAGGGACCGCAGCCAGCGCATACAATCGCGCTCCCGTCCGTT
GGTCCCGGGCAGGACCACGCCGTACTGGTATTCGTACCGGCTGAGCAGGGTCTCCAGGGGGTGGT
TGGGTGCCGCGGGGAACGGGGTCCACGCCACGGTCCACTCGGGCAAAAACCGAGTCGGCACGGC
CCACGGTTCTCCCACCCACGCGTCTGGGGTCTTGATGGCGATAAATCTTACCCCGAGCCGGATTTT
TTGGGCGTATTCGAGAAACGGCACACACAGATCCGCCGCGCCTACCACCCACAAGTGGTAGAGGC
GAGGGGGGCTGGGTTGGTCTCGGTGCAACAGTCGGAAGCACGCCACGGCGTCCACGACCTCGGT
GCTCTCCAAGGGGCTGTCCTCCGCAAACAGGCCCGTGGTGGTGTTTGGGGGGCAGCGACAGGACC
TAGTGCGCACGATCGGGCGGGTGGGTTTGGGTAAGTCCATCAGCGGCTCGGCCAACCGTCGAAGG
TTGGCCGGGCGAACGACGACCGGGGTACCCAGGGGTTCTGATGCCAAAATGCGGCACTGCCTAA
GCAGGAAGCTCCACAGGGCCGGGCTTGCGTCGACGGAAGTCCGGGGCAGGGCGTTGTTCGGTCA
AGGAGGGTCATTACGTTGACGACAACAACGCCCAT

SE ID NO: 22
CCCGGGACCCCCCTGACGTCCTCGGCGGCCTCCGCCTCTTCCTCCTCCGCCTCTTCCTCCTCGGCCC
CGACTCCCGCGGGGGCCACCTCTTCCGCCACCGGGGCCGCGTCCTCCGCCTTCCGCCTCCTCGG
GCGGGGCCGTCGGTGCCCTGGGAGGGAGACAAGAGGGAAACCTCCCTCGGCCCCCGCGCTGCTTCT
GGGCCGCGGGGGCCGAGGAAGTGTGCCCGGAAGACGCGCCACGCGGAGACTTCCGGGGCCGTCC
CCGCGGGCGGCCTCACGCGCTACCTGCCCATCTCGGGGGTCTCTAGCGTGGTCGCCCTGTCGCCTT
ACGTGAACAAGACGATCACGGGGGACTGCCTGCCCATCCTGGACATGGAGACGGGGAACATCGG
GGCGTACGTGGTCCTGGTGGACCAGACGGGAAACATGGCGACCCGGCTGCGGGCCGGGTCCCC
GGCTGGAGCCGCCGCACCCTGCTCCCGAGACCGCGGGTAACCACGTGACGCCCCCGAGTACCC
GACGGCCCCCGCGTCGGAGTGGAACAGCCTCTGGATGACCCCGTGGGAACATGCTGTTCGACCC
AGGGCACCCTAGTGGGCGCCCTGGACTTCCGCAGCCTGCGGTCTCGGCACCCGTGGTCCGGGAG
CAGGGGGCGTCGACCCGGGACGAGGGAAAACAATAAGGGACGCCCCCGTGTTTGTGGGAGGGG
GGGTCGGGCGCTGGGTGGTCTCTGGCCGCGCCCACTACACCAGCCAATCCGTCGGGAGGTG
GAAAGTGAAAGACACGGGCACCACACACCAGCGGGTCTTTTGTGTTGGCCCTAATAAAAAAAACT
CAGGGGATTTTTGCTGTCTGTTGGGAAATAAAGGTTTACTTTTGTATCTTTTCCCTGTCTGTGTTGG
ATGTATCGCGGGGGTGCGTGGGAGTGGGGGTGCGTGGGAGTGGGGGTGCGTGGGAGTGGGGTG

TABLE 1-continued

```
CGTGGGAGTGGGGGTGCGTGGGAGTGGGGGTGCGTGGGAGTGGGGGTGCGTGGGAGTGGGGGTG
CGTGGGAGTGGGGGTGCGTGGGAGTGGGGGTGCCATGTTGGGCAGGCTCTGGTGTTAACCACAG
AGCCGCGGCCCGGGCTGCCTGACCACCGATCCCCGAAAGCATCCTGCCACTGGCATGGAGCCAGA
ACCACAGTGGGTTGGGTGTGGGTGTTAAGTTTCCGCGAGCGCCTGCCCGCCCGGACTGACCTGGC
CTCTGGCCGCCACAAAGGGCGGGGGGGGGGGTTAACTACACTATAGGGCAACAAAGGATGGGAG
GGGTAGCGGGGCGGGACGGGGCGCCCAAAAGGGGGTCGGCCACACCACAGACGTGGGTGTTGGG
GGGTGGGGCGGAGGGGTGGGGGGGGAGACAGAAACAGGAACATAGTTAGAAAACAAGAATGCG
GTGCAGCCAGAGAATCACAGGAGACGAGGGGATGGGCGTGTTGGTTACCAACCCACACCCAGGC
ATGCTCGGTGGTATGAAGGAGGGGGGGCGGTGTTTCTTAGAGACCGCCGGGGGACGTGGGGTTG
GTGTGCAAAGGCACGCGCACCCGCGCCGGCCAGGTGGGCCGGTACCCCATCCCCCCCTCCCCCGA
CCCTTCCCACCCCCGCGTGCCAGAGATCACCCCGGTCCCCGGCACCCGCCACTCCTCCATATCCT
CGCTTTAGGAACAACTTTAGGGGGGGGTACACACGCGCCGTGCATTTCCTTCCACACCCCCCCCT
CCCCCGCACTCCCCCCCCCAGGCAGTAAGACCCAAGCATAGAGAGCCAGGCACAAAAACACAG
GCGGGGTGGGACACATGCCTTCTTGGAGTACGTGGGTCATTGGCGTGGGGGGTTACAGCGACACC
GGCCGACCCCTGGCGGTCTTCCAGCCGGCCCTTAGATAAGGGGGCAGTTGGTGGTCGGACGGGT
AAGTAACAGAGTCTAACTAAGGGTGGGAGGGGGGAAAATAACGGGCTGGTGTGCTGTAACACG
AGCCCACCCGCGAGTGGCGTGGCCGACCTTAGCCTCTGGGGCGCCCCCTGTCGTTTGGGTCCCCCC
CCCTCTATTGGGGAGAAGCAGGTGTCTAACCTACCTGGAAACGCGGCGTCTTTGTTGAACGACAC
CGGGGCGCCCTCGACGAGTGGGATAACGGGGGAGGAAGGGAGGGAGGAGGGTACTGGGGGTGA
AGGGGGGGGGGAGAAGCGAGAACAGGAAAGGCGACGGAGCCCGGCAGAACACCGAGGAAAA
AAAAACCACAGCGCATGC

SEQ ID NO: 23
CCATGTTGGGCAGGCTCTGGTGTTAACCACAGAGCCGCGGCCCGGGCTGCCTGACCACCGATCCC
CGAAAGCATCCTGCCACTGGCATGGAGCCAGAACCACAGTGGGTTGGGTGTGGGTGTTAAGTTTC
CGCGAGCGCCTGCCCGCCCGGACTGACCTGGCCTCTGGCCGCCACAAAGGGCGGGGGGGGGGGT
TAACTACACTATAGGGCAACAAAGGATGGGAGGGGTAGCGGGCGGGACGGGGCGCCCAAAAG
GGGGTCGGCCACACCACAGACGTGGGTGTTGGGGGGTGGGGCGGAGGGGTGGGGGGGGAGACA
GAAACAGGAACATAGTTAGAAAACAAGAATGCGGTGCAGCCAGAGAATCACAGGAGACGAGGG
GATGGGCGTGTTGGTTACCAACCCACACCCAGGCATGCTCGGTGGTATGAAGGAGGGGGGCGG
TGTTTCTTAGAGACCGCCGGGGGACGTGGGGTTGGTGTGCAAAGGCACGCGCACCCGCGCCGGCC
AGGTGGGCCGGTACCCCATCCCCCCCTCCCCCGACCCTTCCCACCCCCGCGTGCCAGAGATCACCC
CGGTCCCCGGCACCCGCCACTCCTCCATATCCTCGCTTTAGGAACAACTTTAGGGGGGGGTACA
CACGCGCCGTGCATTTCCTTCCACACCCCCCCCTCCCCCGCACTCCCCCCCCCAGGCAGTAAGA
CCCAAGCATAGAGAGCCAGGCACAAAAACACAGGCGGGGTGGGACACATGCCTTCTTGGAGTAC
GTGGGTCATTGGCGTGGGGGGTTACAGCGACACCGGCCGACCCCTGGCGGTCTTCCAGCCGGCC
CTTAGATAAGGGGGCAGTTGGTGGTCGGACGGGTAAGTAACAGAGTCTAACTAAGGGTGGGAGG
GGGGGAAAATAACGGGCTGGTGTGCTGTAACACGAGCCCACCCGCGAGTGGCGTGGCCGACCTT
AGCCTCTGGGGCGCCCCCTGTCGTTTGGGTCCCCCCCCCTCTATTGGGGAGAAGCAGGTGTCTAAC
CTACCTGGAAACGCGGCGTCTTTGTTGAACGACACCGGGGCGCCCTCGACGAGTGGGATAACGGG
GGAGGAAGGGAGGGAGGAGGGTACTGGGGGTGAAGGGGGGGGGGAGAAGCGAGAACAGGAA
AGGCGACGGAGCCCGGCAGAACACCGAGGAAAAAAAACCACAGCGCATGCCGGGCCGTTGT
GGGGCCCCGGGCCGGGGCCCCTTGGGTCCGCCGGGGCCCCGGGCCGGGCCGCCACGGGGCCGG
CCGTTGGCGGTAACCCCGAGTGTTCATCTCAGGCCCCGGGCCGGGAACCCGGAAAAGCCTCCGGG
GGGCCTTTTTCGCGTCGCGTGCCGGCGAGCGGGTCCGGACGGGGCCCGGACCGCCGCGGTCGGGG
GCCCCTCGTCCCGGGCCGTACGCGGCCTTCGCCCCGTGAGGGGACAGACGAACGAAACATTCCGG
CGACGGAACGAAAAACACCCCAGACGGGTTAAAGAAACAGAAACCGCAACCCCCACCACCCCCG
AAACGGGGAAAACGAAAAAACAGACCAGCGGCCGGCCGGCGCTTAGGGGGAGGATGTCGCCGA
CGCCCCTTGGCCGCCCCGGCTGCA
```

The embodiments of the present invention will be described in detail below with reference to the accompanying drawings and examples. Those skilled in the art will appreciate that the following drawings and examples are merely illustrative of the invention and are not intended to limit the scope of the invention. The various objects and advantageous aspects of the invention will be apparent to those skilled in the art according to the following detailed descriptions of the drawings and preferred embodiments.

DRAWINGS

Figure 8A:
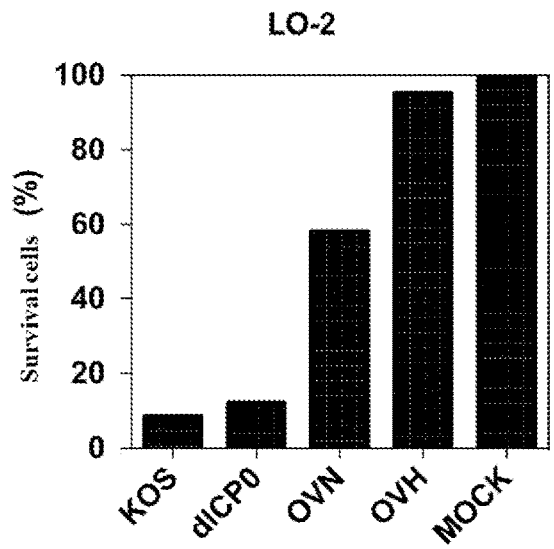
Figure 8B:
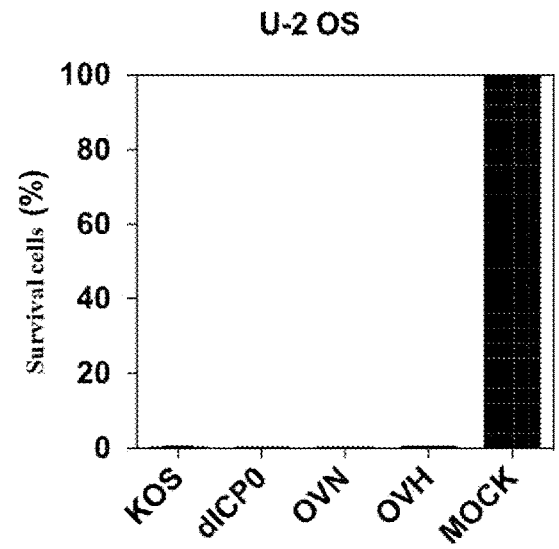

FIGS. 8A and 8B show the cell survival rate after infection of L-O2 cells (FIG. 8A) or U-2 OS cells (FIG. 8B) for 72 h with virus KOS, OVN, OVH or dICP0 at a MOI of 1; wherein MOCK represents cells without being infected with the virus. The results in FIGS. 8A and 8B show that the viruses KOS, OVN, OVH, and dICP0 have substantially comparable cell killing ability in tumor cells (e.g., U-2 OS cells), but viruses OVN and OVH have cell killing ability significantly lower than that of viruses KOS and dICP0 in normal cells (e.g., L-O2 cells).

Figure 9:
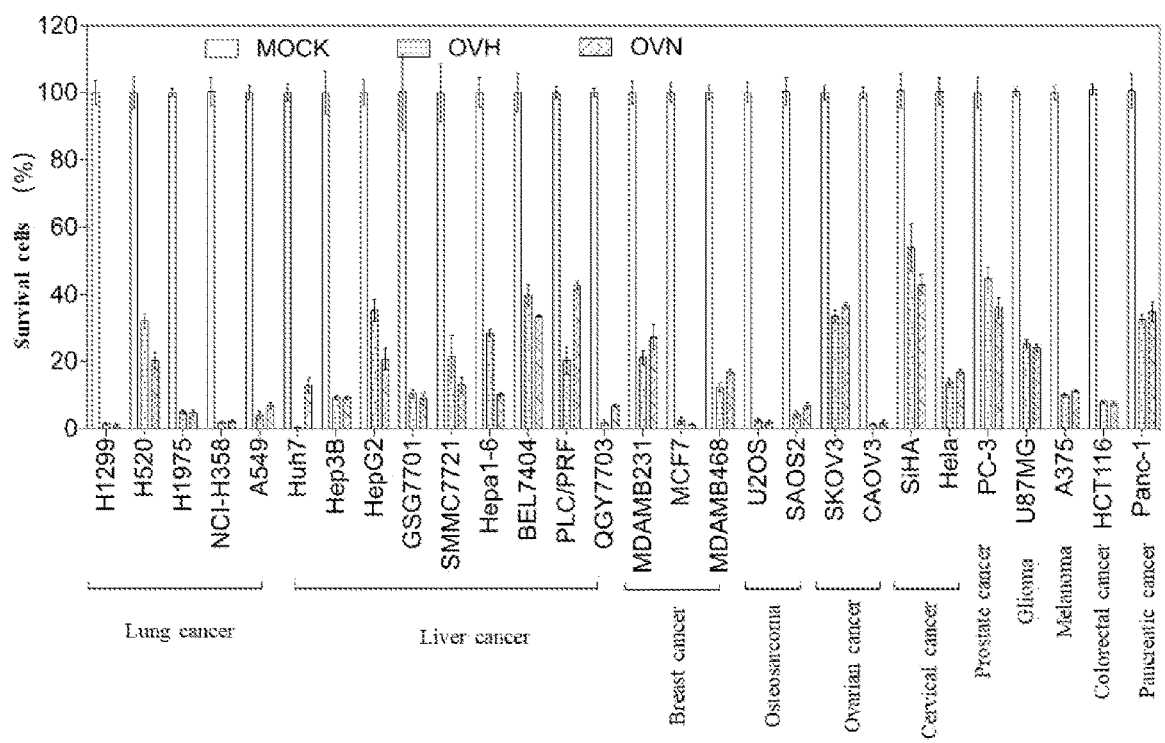

FIG. 9 shows the cell survival rate after infection of various tumor cells with virus OVN or OVH for 48 h; wherein MOCK represents tumor cells without being infected with the virus. The experimental results of FIG. 9 show that the recombinant viruses OVN and OVH can significantly kill a variety of tumor cells.

Figure 10:
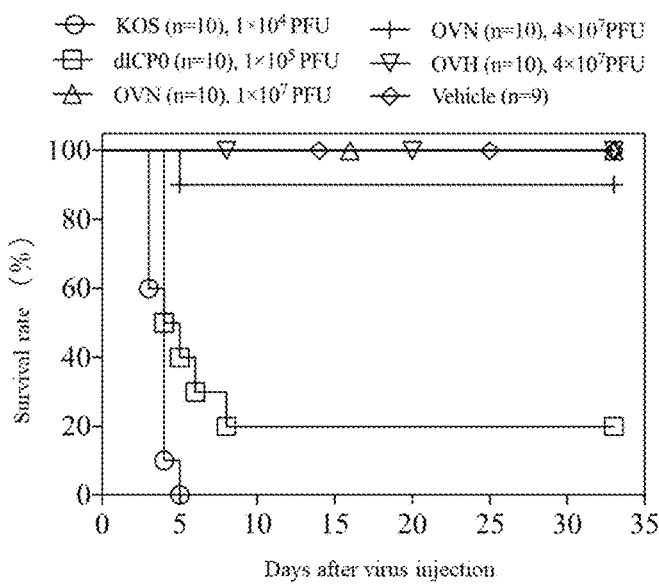

FIG. 10 shows the survival rate of mice after intracranial injection of virus KOS, dICP0, OVN or OVH at a given dose; wherein Vehicle represents mice without being injected with the virus.

Figure 11:
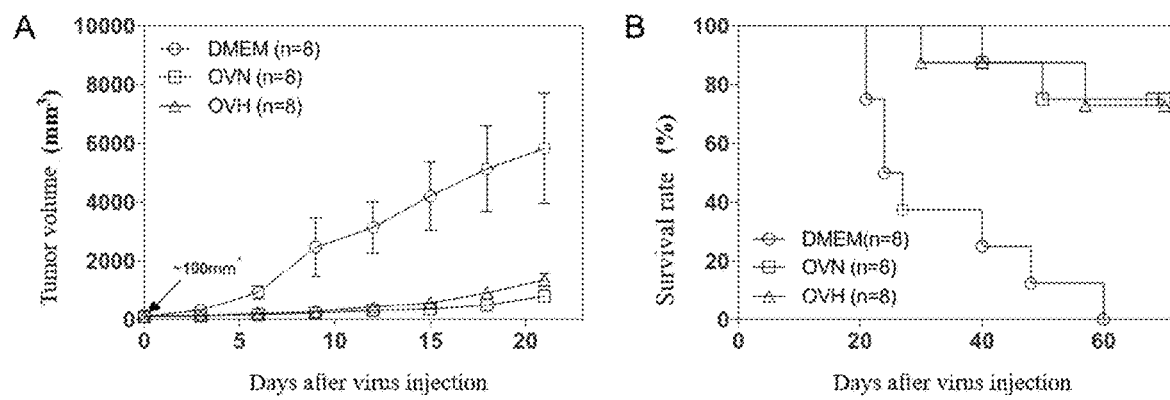

FIG. 11 shows the tumor volume-time curves (FIG. 11A) and survival rate-time curves (FIG. 11B) of nude mice inoculated with Huh7 cells after treatment with OVN or OVH; wherein DMEM represents untreated mice.

Figure 12:
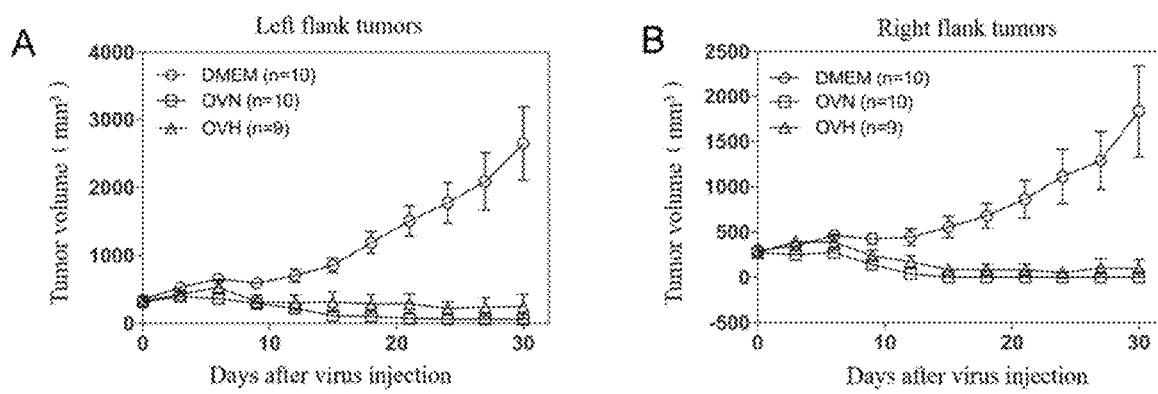

FIG. 12 shows the tumor volume-time curves of tumors on left flank (FIG. 12A) and tumors on right flank (FIG. 12B) of mice (C57BL/6) inoculated with Hepal-6 cells after treatment with OVN or OVH; wherein, DMEM represents untreated mice.

Figure 13:
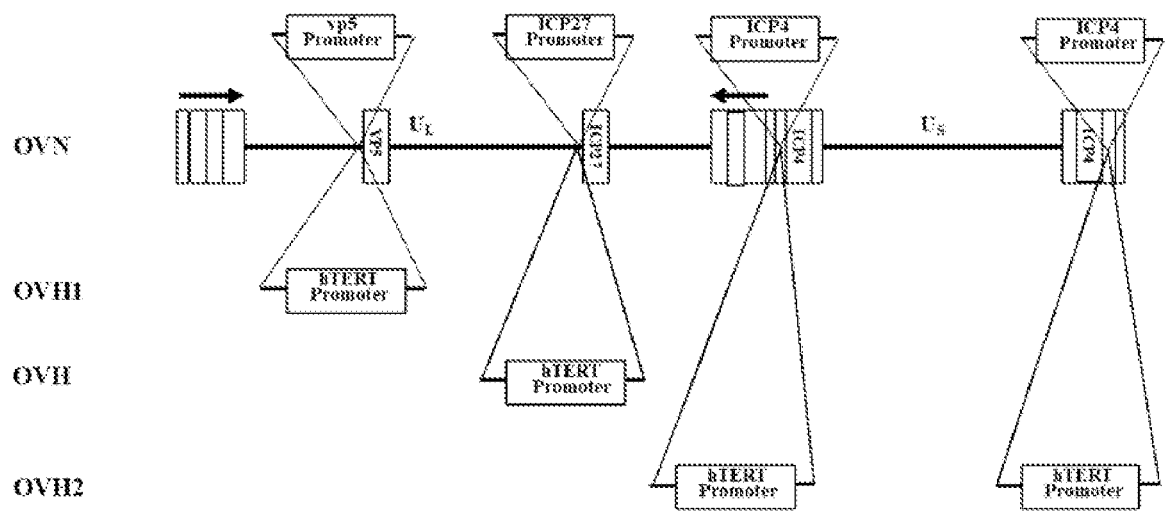

FIG. 13 is a schematic illustration showing the difference in genome structure between recombinant viruses OVH, OVH1 and OVH2 and recombinant virus OVN; wherein, compared with recombinant virus OVN, the native promoter sequence of the ICP27 gene of recombinant virus OVH, the native promoter sequence of the VP5 gene of recombinant virus OVH1, the native promoter sequence of the ICP4 gene of recombinant virus OVH2, were substituted with hTERT core promoter sequence, respectively.

Figure 14:
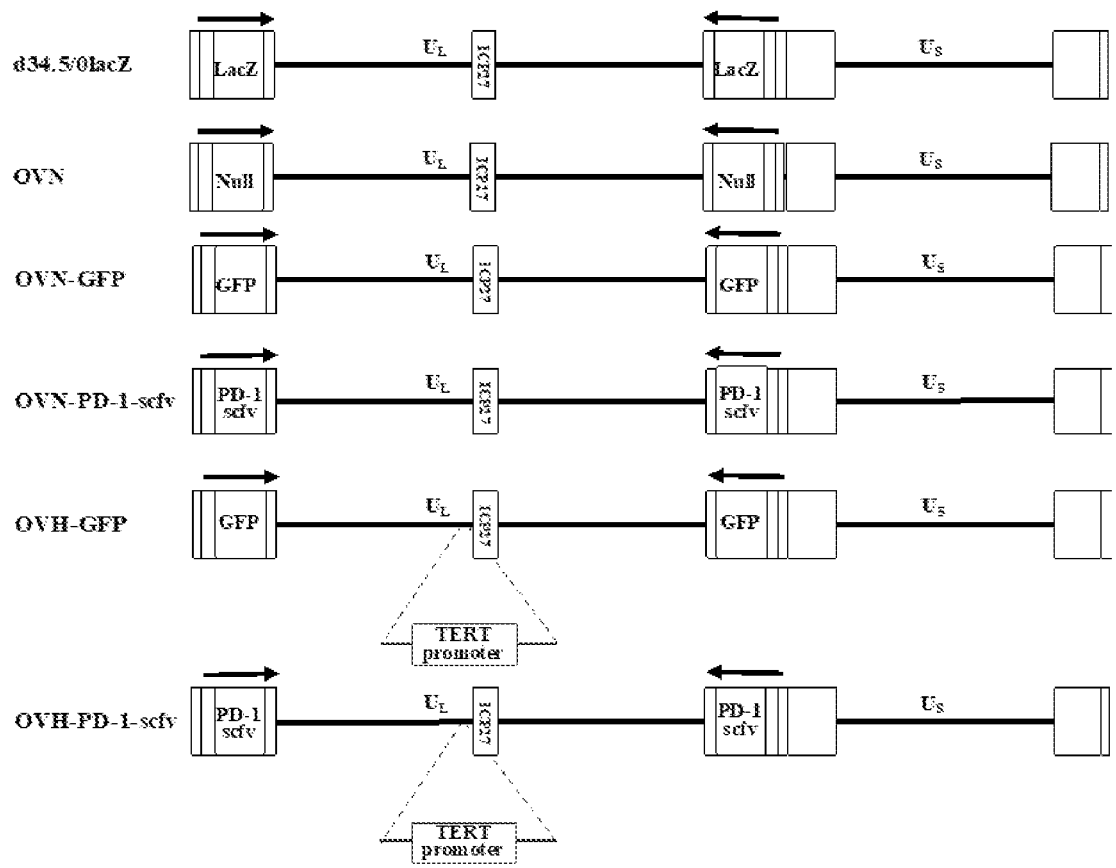

FIG. 14 is a schematic illustration of the genome structure differences among the recombinant viruses d34.5/01acZ, OVN, OVN-GFP, OVN-PD-1-scfv, OVH-GFP and OVH-PD-1-scfv; wherein "NULL" represents deletion.

Figure 15:
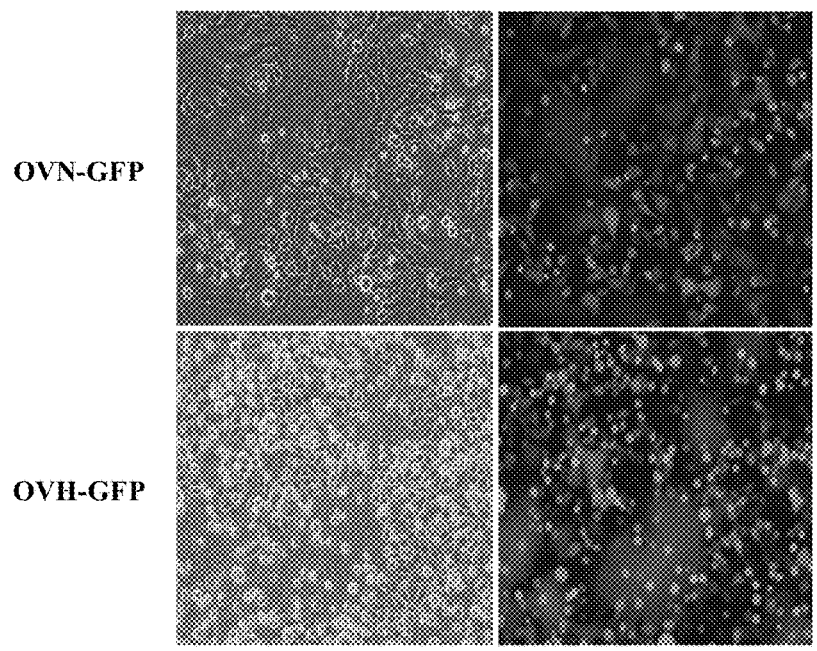

FIG. 15 shows the results of fluorescence microscopic observation of U-2 OS cells infected with the recombinant virus OVN-GFP or OVH-GFP.

Figure 16:
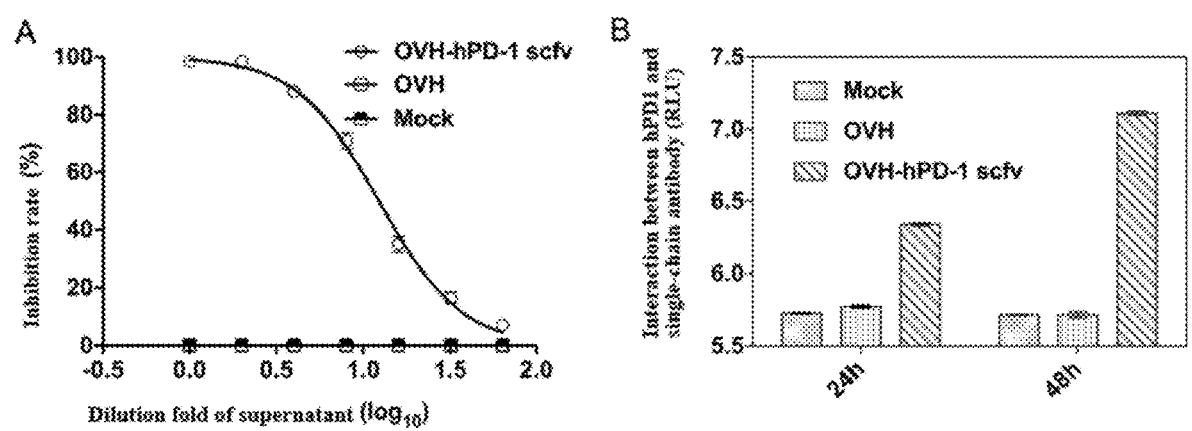

FIG. 16 shows that after infection of U-2 OS cells with the recombinant virus OVH or OVH-PD-1-scfv for 24 h or 48 h, the ability of cell supernatants to inhibit the specific binding of PD-1/PD-L1 (FIG. 16A) and the analysis results of the interaction between the cell supernatants and PD-1 protein (FIG. 16B); wherein MOCK represents tumor cells without being infected with the virus.

Figure 17:
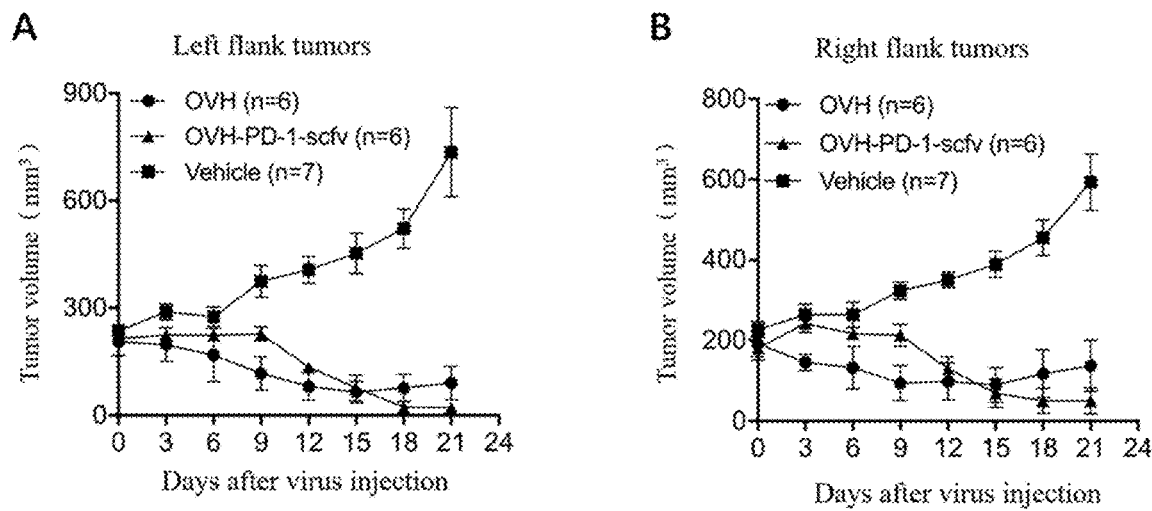

FIG. 17 shows the tumor volume-time curves of tumors on left flank (FIG. 17A) and tumors on right flank (FIG. 17B) of mice (C57BL/6) inoculated with Hepal-6 cells after treatment with OVH or OVH-PD-1-scfv; wherein, Vehicle represents untreated mice.

Figure 18:
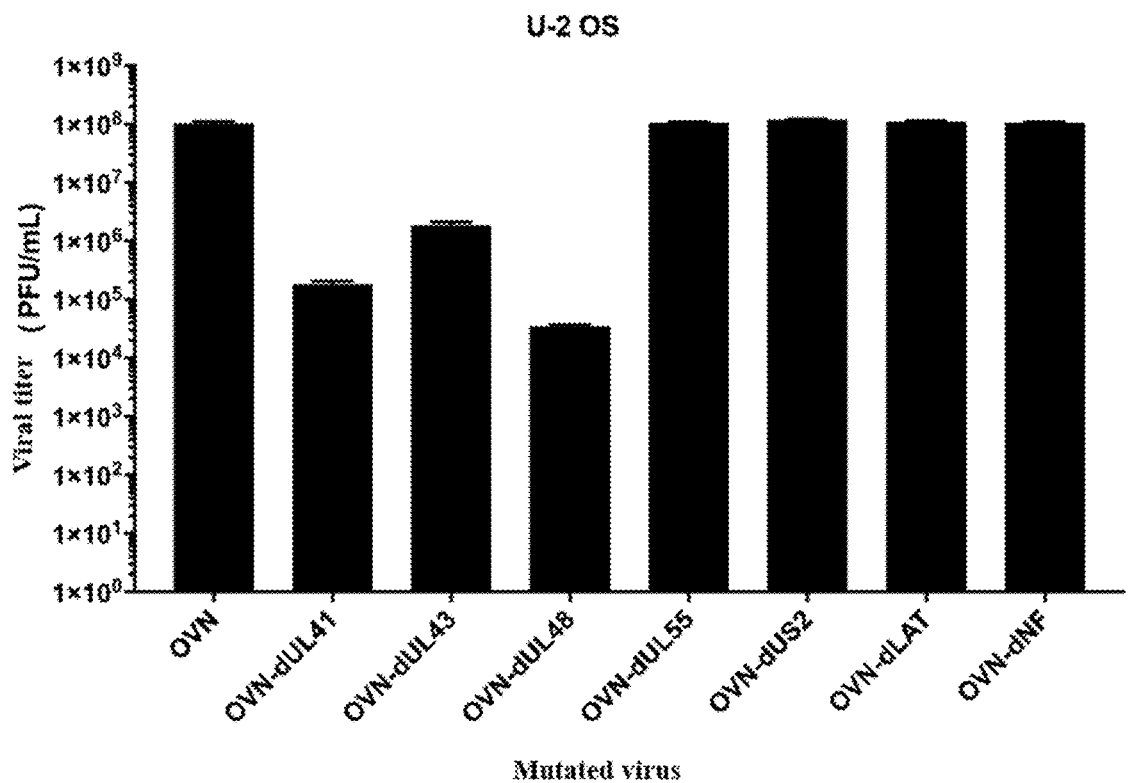

FIG. 18 shows the virus titers after infection of U-2 OS cells for 60 h with virus OVN, OVN-dUL41, OVN-dUL43, OVN-dUL48, OVN-dUL55, OVN-dUS2, OVN-dLAT or OVN-dNF at a MOI of 0.01, respectively.

Figure 19:
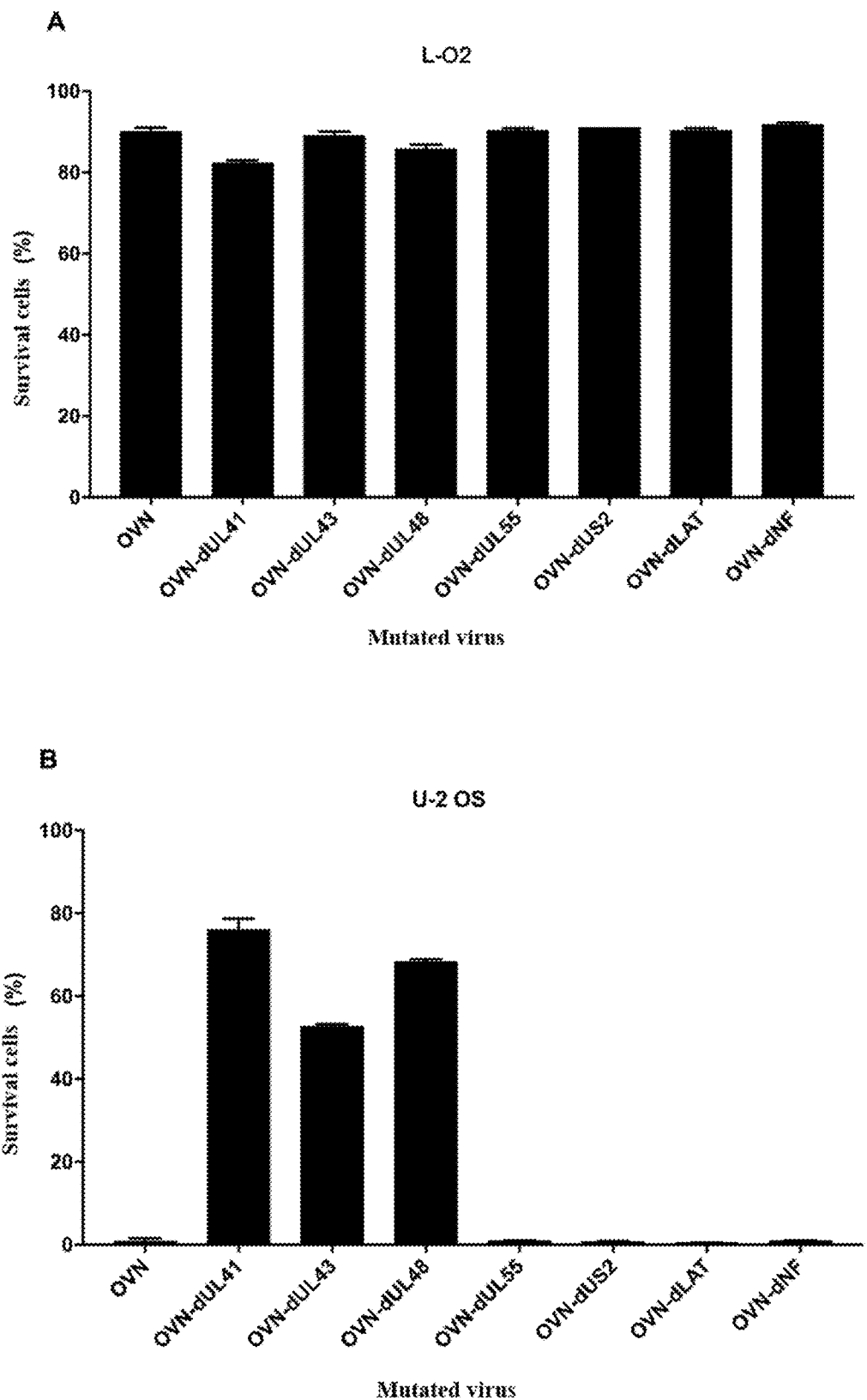

FIG. 19 shows the cell survival rates after infection of normal cells (L-O2 cells, FIG. 19A) or tumor cells (U-2 OS cells, FIG. 19B) for 72 h with the virus OVN, OVN-dUL41, OVN-dUL43, OVN-dUL48, OVN-dUL55, OVN-dUS2, OVN-dLAT or OVN-dNF at a MOI of 0.5, respectively.

SPECIFIC MODELS FOR CARRYING OUT THE INVENTION

The invention is described with reference to the following examples which are intended to illustrate, but not limit the invention.

Unless otherwise specified, the molecular biology experimental methods, virological experimental methods, immunoassays, and zoological experimental methods used in the present application are all experimental methods conventionally used by those skilled in the art. For example, molecular biology experimental methods can be the methods described in: J. Sambrook et al., Molecular Cloning: A Laboratory Manual, 2nd Edition, Cold Spring Harbor Laboratory Press, 1989, and F. M. Ausubel et al., Guide to Molecular Biology Experiments, 3rd edition, John Wiley & Sons, Inc., 1995. The reagents (e.g., enzymes, plasmids, and primers) used in the respective examples were purchased from commercial companies, and various reagents (e.g., enzymes) were used in accordance with the conditions recommended by the manufacturers. Those skilled in the art would understand that the examples are illustrative to the invention, and are not intended to limit the scope of the invention.

Example 1. Construction of Recombinant Virus OVN and OVH (1.1) Culture and Titer Determination of Herpes Simplex Virus Type 1 (HSV-1)

Wild-type HSV-1 strain KOS was purchased from ATCC (Cat. No. VR-1493™), and its whole-genome information has been published in NCBI (GenBank: JQ673480.1). Cultured Vero cells (purchased from ATCC, USA, Cat. No. CCL-81™) were infected with the strain KOS at a MOI of 0.1. After 48 hours, all cells were collected by cell scraper and centrifuged to remove the cell culture medium. The obtained cell precipitate was resuspended in fresh complete medium and stored at −80° C. Subsequently, the cell suspension was repeatedly freeze-thawed (3 times), then centrifuged, and the supernatant was collected to obtain a virus solution. The virus solution was aliquoted and stored at −80° C.

U-2 OS cells (purchased from ATCC, USA, catalogue number HTB-96™) were seeded in 6 cm culture plates at a density of $1 \times 10^6$ cells. After the cells were grown into a monolayer, serial 10-fold dilutions of the virus solution obtained above were performed, and then the cells were infected with virus solutions (500 μl) of different dilution gradients, respectively. After 75 min of infection, the cell culture medium was discarded, 5 mL of fresh complete medium was added, and the cells were further cultured. After 2 h, 10 mL of methylcellulose medium was added, and the plate was placed in an incubator for 2 days. Subsequently, a basal medium comprising 0.01% neutral red was added into the plate and incubation was continued for 12 hr. After the completion of the culture, all the cell culture medium was discarded, and the plaques of the respective culture plates were counted. According to the number of plaques of each culture plate and the dilution factor of the virus solution, the virus titer was calculated according to the following formula: virus titer (PFU/mL)=number of plaques per plate×2×virus dilution factor.

(1.2) Construction of Recombinant Plasmid

The sequence (SEQ ID NO: 1) between the $33^{rd}$ base (nt33) to the $5876^{th}$ base (nt5876) of the wild type HSV-1 virus genome (GenBank: JQ673480.1) was cloned to the commercially available PUC57 vector (Shanghai Shenggong) using restriction enzymes SacI and PstI, thereby obtaining plasmid PUC57-F0. Subsequently, the sequence between the NcoI and SalI cleavage sites in the plasmid PUC57-F0 was substituted with the gene sequence of LacZ (SEQ ID NO: 2) using restriction endonucleases NcoI and SalI, thereby obtaining plasmid PUC57-d34.5/01acZ. Further, the sequence between the NcoI and SalI cleavage sites in the plasmid PUC57-F0 was also cut off, thereby obtaining plasmid PUC57-d34.5/0.

(1.3) Construction and Identification of Recombinant Viruses OVN and OVH

Figure 1A:
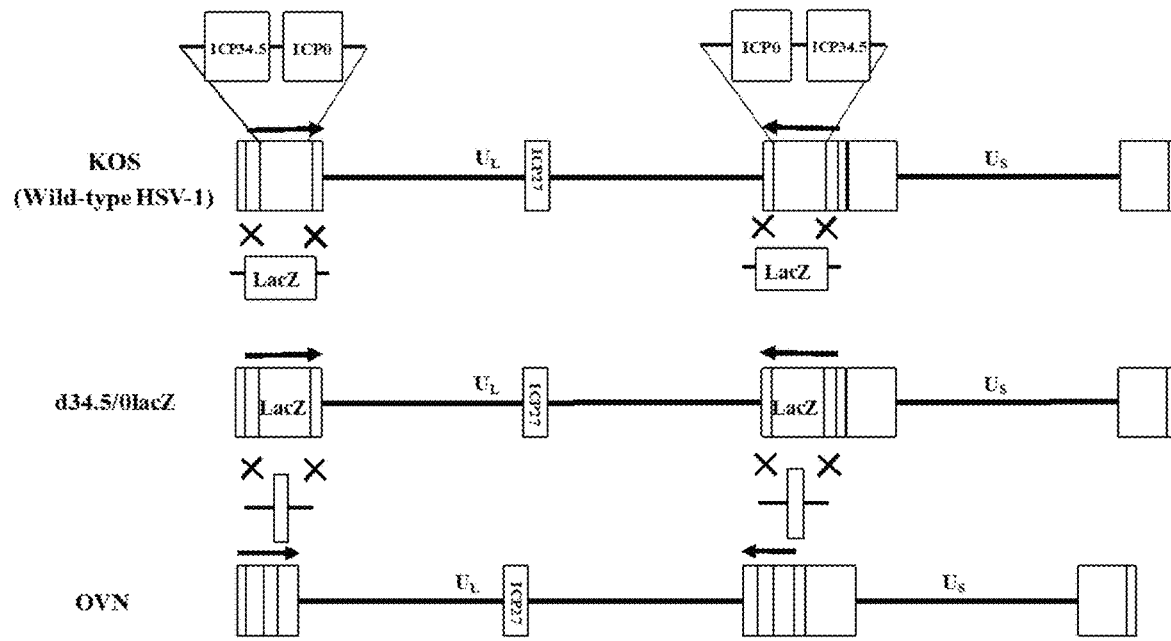
FIG. 1A shows the construction strategy of the recombinant virus OVN.
Figure 1B:
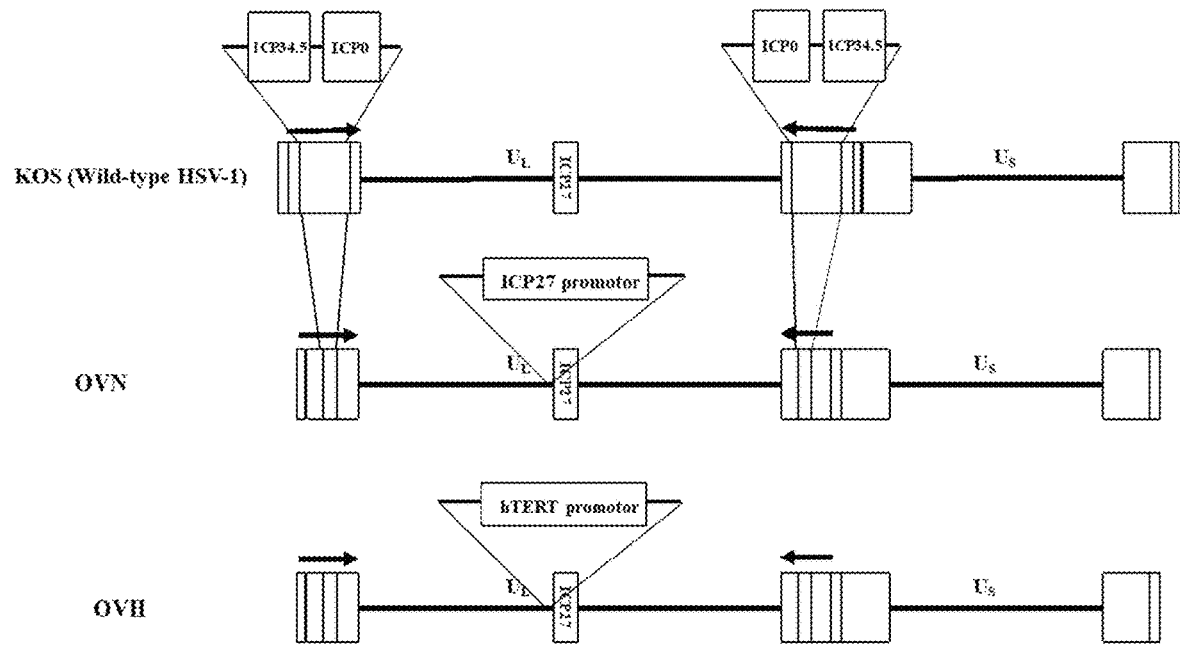
FIG. 1B shows the construction strategy of the recombinant virus OVH.

The construction strategies of the recombinant viruses OVN and OVH are shown in FIG. 1A-1B, respectively.

(1.3.1) Construction of Recombinant Virus d34.5/01acZ

U-2 OS cells were seeded in 24-well plates at a density of 1×10$^5$ cells per well and cultured overnight at 37° C. in a cell culture incubator. The recombinant plasmid PUC57-d34.5/01acZ was transfected into U-2 OS cells using transfection reagent lipofectamine 2000. After 24 h of transfection, the cells were infected with the virus strain KOS at a MOI of 3. After cytopathic effect was observed, the cells were harvested. The harvested cells were lysed by repeated freeze-thaw method, then centrifuged, and the supernatant was collected to obtain a virus solution. The virus titer of the obtained virus solution was measured.

The harvested virus was inoculated into a culture plate in which monolayer of U-2 OS cells were grown. After culturing for 2 days, a basal medium comprising 0.01% neutral red and 100 ug/mL X-gal was uniformly added to the culture plate, and the cells were further cultured for 12 hr. Subsequently, blue plaques appearing on the culture plate were selected, and the virus obtained from the blue plaques was monoclonalized (3 times) to obtain the recombinant virus d34.5/01acZ. After being verified by sequencing, it was found that the two copies of the ICP34.5 and ICP0 genes in the recombinant virus d34.5/01acZ genome were substituted with the lacZ gene as compared to the strain KOS.

(1.3.2) Construction of Recombinant Virus OVN (d34.5/0)

U-2 OS cells were seeded in 24-well plates at a density of 1×10$^5$ cells per well and cultured overnight at 37° C. in a cell culture incubator. The recombinant plasmid PUC57-d34.5/0 was transfected into U-2 OS cells using transfection reagent lipofectamine 2000. After 24 h of transfection, the cells were infected with the recombinant virus d34.5/01acZ at a MOI of 3. After cytopathic effect was observed, the cells were harvested. The harvested cells were lysed by repeated freeze-thaw method, then centrifuged, and the supernatant was collected to obtain a virus solution. The virus titer of the obtained virus solution was measured.

The harvested virus was seeded into a culture plate in which monolayer of U-2 OS cells were grown. After culturing for 2 days, a basal medium comprising 0.01% neutral red and 100 ug/mL X-gal was uniformly added to the culture plate, and the cells were further cultured for 12 hr. Subsequently, white plaques appearing on the culture plate were selected, and the virus obtained from the white plaques was monoclonalized (3 times) to obtain the recombinant virus OVN (d34.5/0). After being verified by sequencing, the two copies of the lacZ gene had been deleted in the recombinant virus OVN (d34.5/0) genome as compared with the recombinant virus d34.5/01acZ; and the sequence of nt510 to nt5439 (SEQ ID NO: 6) and the sequence of nt120802 to nt125731 (SEQ ID NO: 6) of the wild type HSV-1 genome (GenBank: JQ673480.1) were deleted in the recombinant virus OVN (d34.5/0) as compared with the strain KOS.

(1.3.3) Construction of Recombinant Virus OVH

Sequence of base 112861 (nt112861) to 113422 (nt113422) (SEQ ID NO: 3) of the wild-type HSV-1 genome (GenBank: JQ673480.1) was cloned into the commercially available PUC57 vector by using restriction endonucleases SacI and PmeI, thereby obtaining plasmid PUC57-27p0. Subsequently, the sequence of base 113590 (nt113590) to base 115194 (nt115194) (SEQ ID NO: 4) of the wild-type HSV-1 viral genome (GenBank: JQ673480.1) was cloned into the plasmid PUC57-27p0 by using restriction enzymes SpeI and PstI, thereby obtaining plasmid PUC57-27p1. In the plasmid PUC57-27p1, the native promoter sequence of the ICP27 gene (nt113422 to nt113590 of the wild-type HSV-1 genome (GenBank: JQ673480.1)) had been deleted.

Subsequently, the sequence between the PmeI and SpeI cleavage sites in the plasmid PUC57-27p1 was substituted with the LacZ expression sequence (SEQ ID NO: 2), thereby obtaining plasmid PUC57-27p/lacZ. In addition, the sequence between the PmeI and SpeI cleavage sites in the plasmid PUC57-27p1 was substituted for the core promoter sequence of the adult telomerase reverse transcriptase hTERT (SEQ ID NO: 5; see, Takakura M, Kyo S, Kanaya T, et al. Cloning of human telomerase catalytic subunit (hTERT) gene promoter and identification of proximal core promoter sequences essential for transcriptional activation in immortalized and cancer cells [J]. Cancer Res, 1999, 59 (3): 551-557), thereby obtaining plasmid PUC57-27p/htert. In the plasmid PUC57-27p/htert, the ICP27 gene was regulated by a tumor-specific promoter (i.e., the hTERT core promoter).

Subsequently, referring to the construction methods described in (1.3.1) and (1.3.2), the recombinant virus OVN was used as a starting virus, and the hTERT core promoter sequence was introduced into the recombinant virus OVN genome by using the plasmids PUC57-27p/lacZ and PUC57-27p/htert for regulating the ICP27 gene, thereby constructing a recombinant virus OVH. After being verified by sequencing, the native promoter sequence of the ICP27 gene (nt113423 to nt113589 of the wild-type HSV-1 genome (GenBank: JQ673480.1)) had been substituted by the hTERT core promoter (SEQ ID NO: 5) in the recombinant virus OVH genome as compared with the recombinant virus OVN.

(1.4) Comparison of Recombinant Viruses OVN and OVH with Known Recombinant HSV Viruses Currently, a variety of recombinant HSV viruses had been developed for use in tumor therapy, including, for example, HSV1716, NV1020, G207, OncoVex$^{GM-CSF}$ (T-VEC), and the like. The genome modifications comprised in these recombinant HSV viruses and the recombinant viruses OVN and OVH of the present invention are summarized in Table 2 below.

TABLE 2

Genome modifications comprised in various recombinant HSV viruses

| Name | Genetic modification | Country |
| --- | --- | --- |
| HSV1716 | Deletion of dual copies of ICP34.5 | UK |
| NV1020 | Deletion of 15 kb fragment at UL/US junction (i.e., deletion of single copies ICP34.5, ICP0, ICP4 and UL56) | USA |
| G207 | Deletion of dual copies of ICP34.5 and ICP6 | USA |
| OncoVex$^{GM-CSF}$ (T-VEC) | Deletion of dual copies of ICP34.5 and ICP47 | USA |
| OVN | Deletion of dual copies of (ICP34.5 and ICP0) | China |
| OVH | Deletion of dual copies of (ICP34.5 and ICP0), and the native promoter of the ICP27 gene was substituted with the hTERT core promoter | China |

Figure 2:
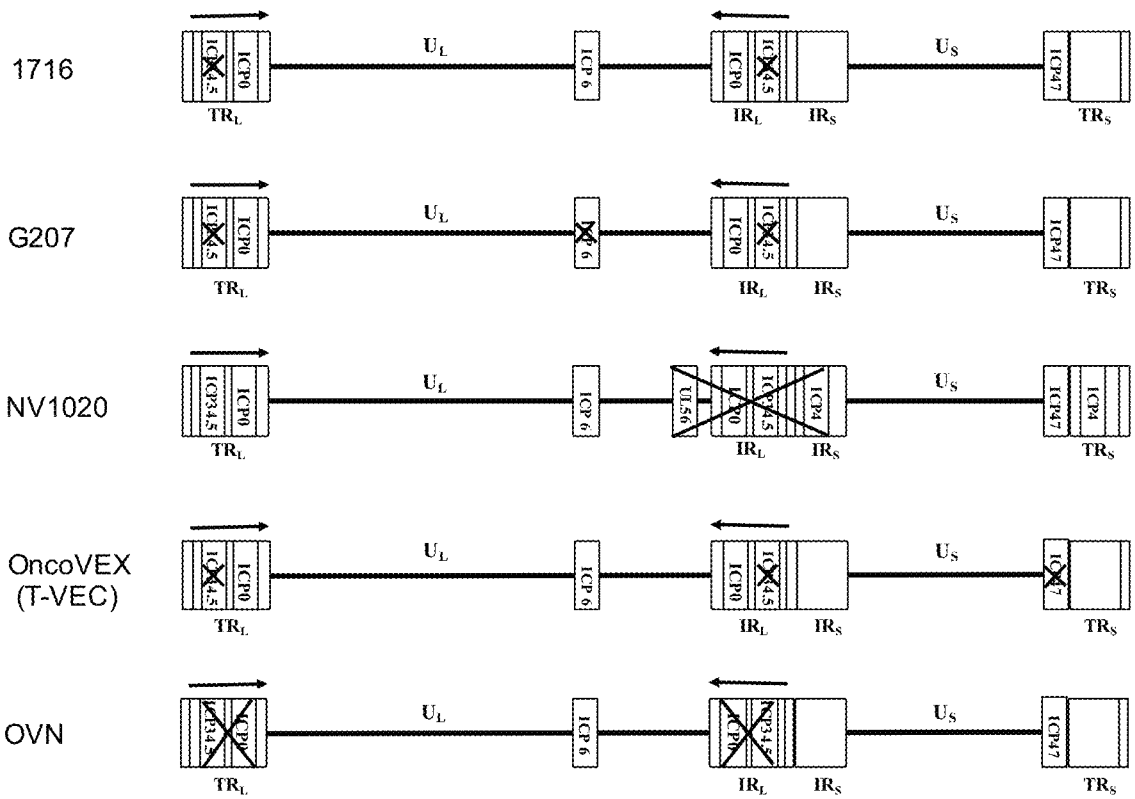
FIG. 2 is a schematic illustration of the genome modifications comprised in the recombinant viruses HSV1716, NV1020, G207, OncoVex$^{GM-CSF}$ (T-VEC) and OVN; wherein the symbol "x" indicates a deletion.

FIG. 2 is a schematic illustration of the genome modifications comprised in recombinant viruses HSV1716, NV1020, G207, OncoVex$^{GM-CSF}$ (T-VEC) and OVN.

Example 2. Characterization of Recombinant Viruses OVN and OVH

Figure 3:
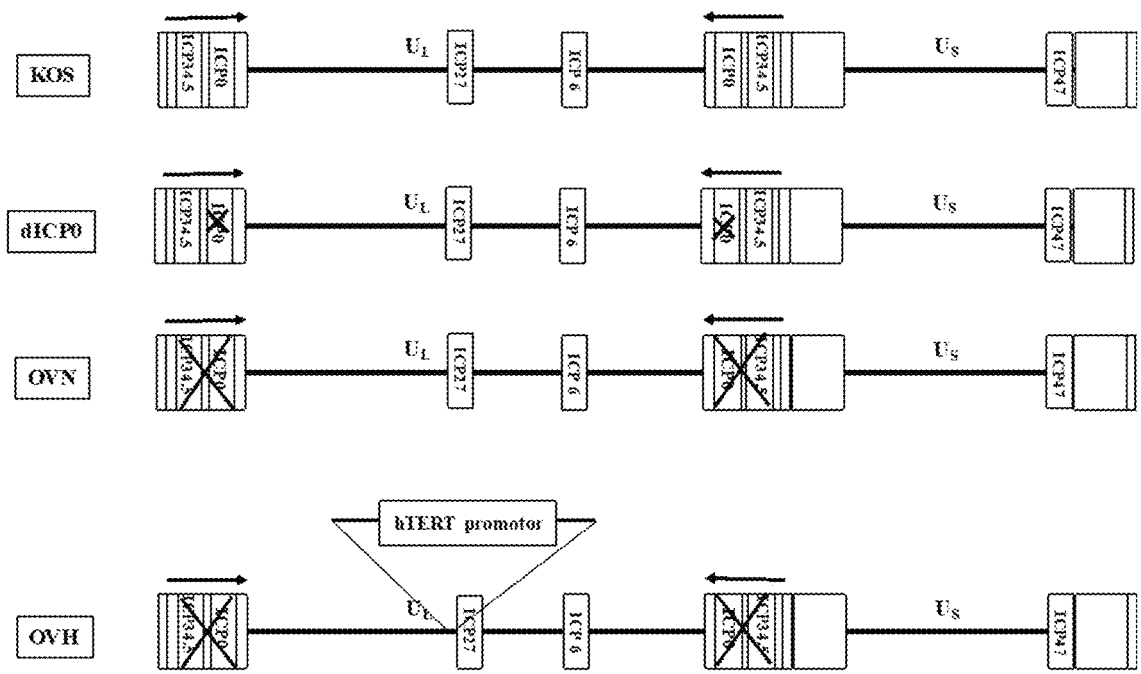
FIG. 3 is a schematic illustration of the genome modifications comprised in the recombinant viruses OVN, OVH and dICP0 in comparison with the virus strain KOS; wherein the symbol "x" indicates a deletion.

The recombinant virus dICP0 was constructed with reference to the method described in Example 1, which had the deletion of two copies of the ICP0 gene as compared to the strain KOS. The virus strain KOS and the recombinant virus dICP0 were used as control viruses to characterize the recombinant viruses OVN and OVH. FIG. 3 is a schematic illustration of the genome modifications comprised in the recombinant viruses OVN, OVH and dICP0 compared to the virus strain KOS; wherein the recombinant virus dICP0 had the deletion of two copies of the ICP0 gene compared to the virus strain KOS; the recombinant virus OVN had the deletion of the two copies of the ICP34.5 gene and the two copies of the ICP0 gene; the recombinant virus OVH had the deletion of the two copies of the ICP34.5 gene and the two copies of the ICP0 gene, and the native promoter of the ICP27 gene was substituted with the hTERT core promoter.

The gene deletions in the recombinant viruses OVN, OVH and dICP0 were verified by PCR. Briefly, the PCR was carried out using primers for specific amplification of ICP0 gene, ICP34.5 gene, ICP27 gene or hTERT core promoter and using the genome of the virus strain KOS, OVN, OVH or dICP0 as a template. The primers used in the PCR are summarized in Table 3.

TABLE 3

Primer sequences

| SEQ ID NO: | Primer name | Sequence (5'-3') |
|---|---|---|
| 9 | ICP0-F | GACGTGTGCGCCGTGTGCACGGATGA |
| 10 | ICP0-R | ACTCTGTTCTTGGTTCGCGGCCTGAGCCA |
| 11 | ICP34.5-F | ATGGCCCGCCGCCGCCATCGC |
| 12 | ICP34.5-R | TTAGACCGAGTTCGCCGGGC |
| 13 | ICP27-F | ATGGCGACTGACATTGATATGCTAATTGA |
| 14 | ICP27-R | CTAAAACAGGGAGTTGCAATAAAAATATTTGC |
| 15 | htertp-F | CTCCCAGTGGATTCGCGGGCACAGAC |
| 16 | htertp-R | CTGCCTGAAACTCGCGCCGCGAGGA |

Figure 4:
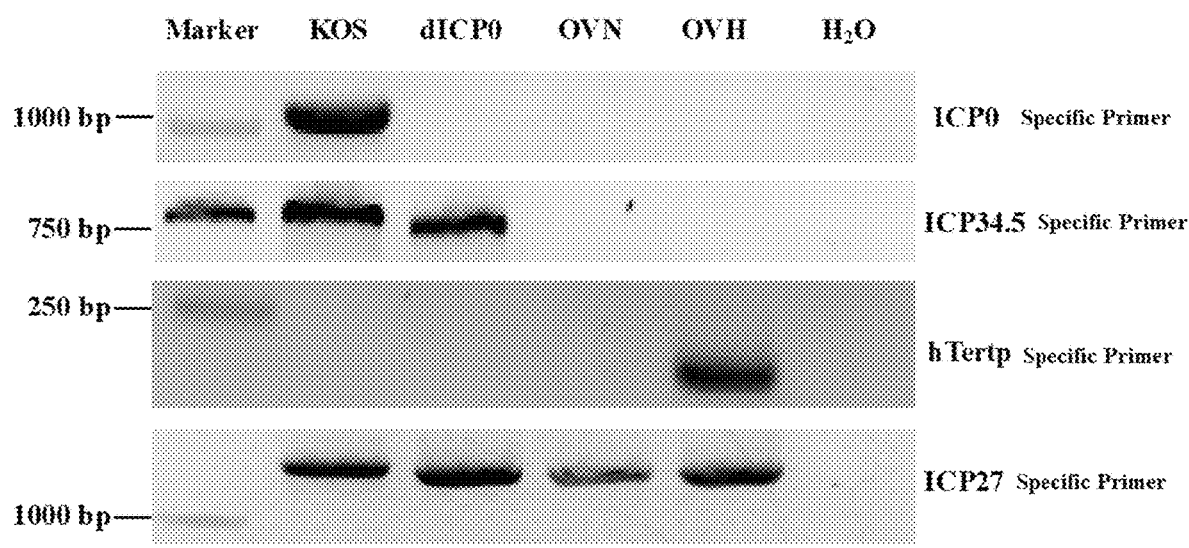
FIG. 4 shows the gel electrophoresis results of products obtained by PCR using the genome of virus strain KOS, OVN, OVH or dICP0 as a template and primers capable of specifically amplifying ICP0 gene, ICP34.5 gene, ICP27 gene or hTERT core promoter.

After the reaction was completed, the PCR product was analyzed by gel electrophoresis. The results are shown in FIG. 4. FIG. 4 shows the gel electrophoresis results of the products obtained by PCR using a genome of virus strain KOS, OVN, OVH or dICP0 as template and primers capable of specifically amplifying ICP0 gene, ICP34.5 gene, ICP27 gene or hTERT core promoter; wherein lane 1 represents a DNA molecular weight marker; lane 2 represents a PCR product using the virus strain KOS genome as template; lane 3 represents a PCR product using the recombinant virus dICP0 genome as template; lane 4 represents a PCR product using the recombinant virus OVN genome as template; Lane 5 represents a PCR product using the recombinant virus OVH genome as template; Lane 6 represents a PCR product using water as template.

The results in FIG. 4 show that the genome of the virus strain KOS comprised the ICP0 gene, the ICP34.5 gene and the ICP27 gene, but did not comprise the hTERT core promoter; the genome of the recombinant virus dICP0 comprised the ICP34.5 gene and the ICP27 gene, but did not comprise the ICP0 gene and the hTERT core promoter; the genome of recombinant virus OVN comprised the ICP27 gene, but did not comprise the ICP34.5 gene, the ICP0 gene and the hTERT core promoter; the genome of the recombinant virus OVH comprised the ICP27 gene and the hTERT core promoter, but did not comprise the ICP34.5 gene and the ICP0 gene.

In addition, the gene expression (mRNA) of cells after infection with KOS, OVN, OVH or dICP0 was also analyzed by using real-time quantitative PCR. Briefly, the U-2 OS host cells were infected with KOS, OVN, OVH and dICP0, respectively. After cytopathic effect was observed, the cells were harvested and total mRNA was extracted. The total mRNA was reverse transcribed into cDNA, and real-time quantitative PCR was carried out using primers specifically amplifying the ICP0 gene, the ICP34.5 gene or the ICP27 gene, respectively. The result is shown in FIG. 5.

Figure 5:
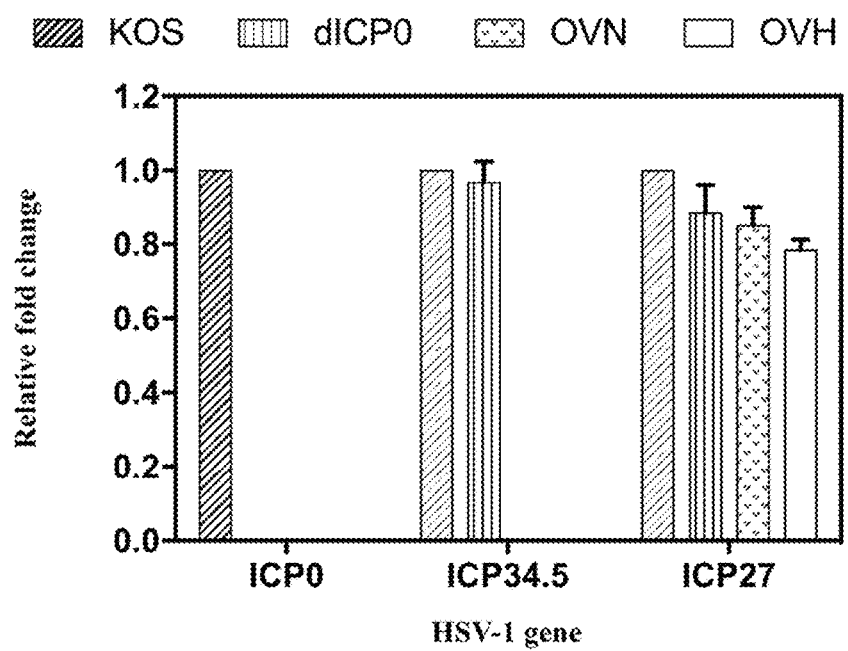
FIG. 5 shows the results of real-time quantitative PCR analysis of IE gene expression (mRNA) of KOS, OVN, OVH or dICP0.

FIG. 5 shows the results of real-time quantitative PCR analysis of IE gene expression (mRNA) of KOS, OVN, OVH or dICP0. The results in FIG. 5 show that the strain KOS was capable of expressing the ICP0 gene, the ICP34.5 gene and the ICP27 gene; the recombinant virus dICP0 was capable of expressing the ICP34.5 gene and the ICP27 gene, but did not express the ICP0 gene; the recombinant virus OVN and OVH were capable of expressing the ICP27 Gene, but expressed neither the ICP34.5 gene nor the ICP0 gene. This indicates that the recombinant virus dICP0 had the deletion of the two copies of the ICP0 gene, and the ICP0 protein could not be expressed after infection of the host cells; and the recombinant viruses OVN and OVH both had the deletion of the two copies of the ICP34.5 gene and the ICP0 gene, and thus the ICP0 protein and the ICP34.5 protein could not be expressed after infection of the host cells.

Example 3. Evaluation of Replication Ability and Killing Ability of Recombinant Virus OVN/OVH Normal cells (L-O2 cells) and tumor cells (U-2 OS cells) in logarithmic growth phase were seeded in 6 cm culture plates at a density of 5-7.5×10$^6$ cells/plate. Subsequently, the cultured cells were infected with the virus KOS, OVN, OVH or dICP0 at a MOI of 1. After 48 hours of infection, the state of the cells was observed under a microscope and photographed. Subsequently, the virus-infected cells were digested, and the survival rate of the cells was calculated by trypan blue staining. Cell survival rate (%)=(number of viable cells after infection with virus)/(number of control cells not infected with virus)×100. A 3-well replicate was set for each group of experiments and the experimental result was the average of 3 independent experiments. In addition, the virus titers at different time points after infection of normal cells (L-O2 cells) and tumor cells (U-2 OS cells) with virus KOS, OVN, OVH or dICP0 were determined with reference to the protocol described in Example 1. A 3-well replicate was set for each group of experiments and the experimental result was the average of 3 independent experiments. The experimental results are shown in FIG. 6-8.

Figure 6:
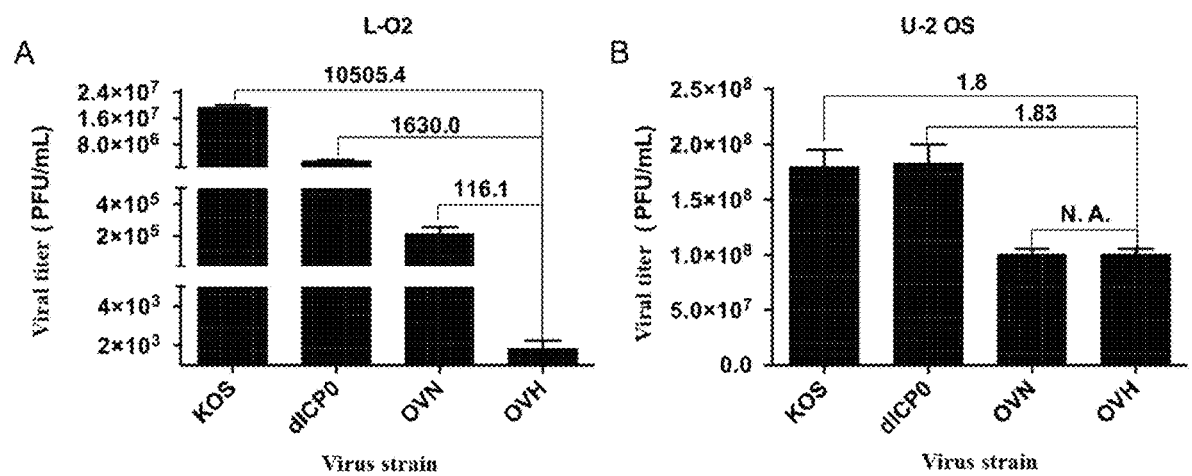
FIG. 6 shows the virus titers after infection of L-O2 cells (FIG. 6A) or U-2 OS cells (FIG. 6B) for 48 h with virus KOS, OVN, OVH or dICP0 at a multiplicity of infection of 1 (i.e. MOI=1).

FIG. 6 shows the virus titers after 48 h of infection of L-O2 cells (FIG. 6A) or U-2 OS cells (FIG. 6B) with virus KOS, OVN, OVH or dICP0 at a MOI of 1. The results in FIG. 6A show that both virus KOS and dICP0 had a high level of replication after infection of L-O2 cells, and their virus titers reached approximately $1.94 \times 10^7$ and $3.01 \times 10^6$ pfu/ml after 48 h of infection; while the replication ability of the virus OVN and OVH were decreased significantly, and their virus titers were only about $2.14 \times 10^5$ and $1.85 \times 10^3$ pfu/ml after 48 h of infection. The results in FIG. 6B show that the viruses KOS, OVN, OVH and dICP0 had a high level of replication after infection of U-2 OS cells, and their virus titers were $1.01-1.83 \times 10^8$ pfu/ml after 48 h of infection. These results indicate that the viruses KOS and dICP0 were capable of replicating at high levels in normal cells (e.g., L-O2 cells) and tumor cells (e.g., U-2 OS cells); whereas the viruses OVN and OVH were only capable of replicating at high levels in tumor cells (e.g., U-2 OS cells) (their replication abilities were only slightly decreased as compared to the viruses KOS and dICP0), and their replication abilities were significantly decreased in normal cells (e.g., L-O2 cells). For example, in L-O2 cells, the replication abilities of the viruses OVN and OVH were decreased by about 90 times and $10^4$ times, respectively, as compared to that of the virus KOS; and the replication abilities of the viruses OVN and OVH were decreased by about 14 times and $1.6 \times 10^3$ times, respectively, as compared to that of the virus dICP0.

Figure 7:
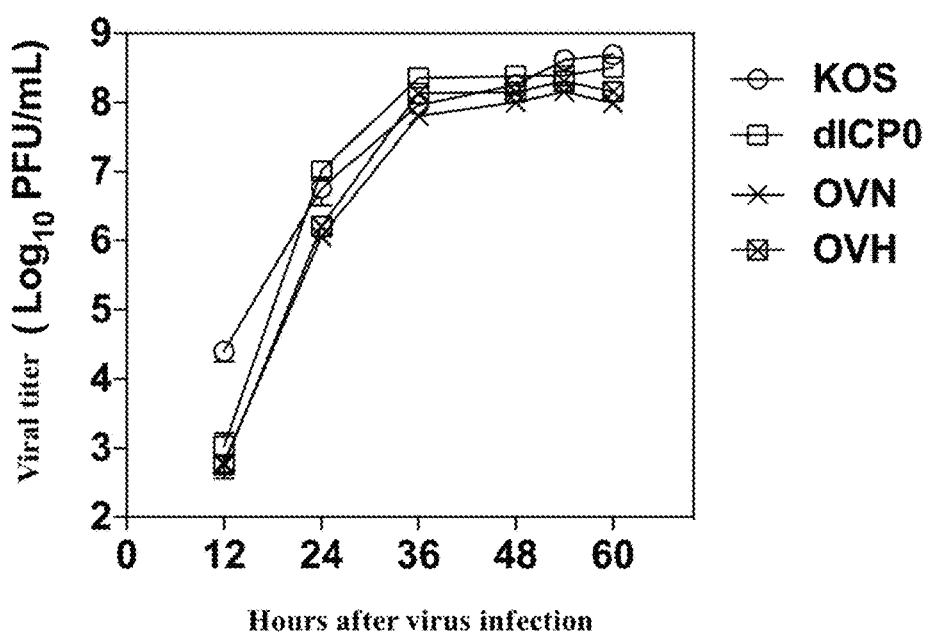
FIG. 7 shows the virus titers at different time points (12 h, 24 h, 36 h, 48 h and 60 h after infection) after infection of monolayer U-2 OS cells with virus KOS, OVN, OVH or dICP0 at a MOI of 0.01. The results in FIG. 7 show that the virus KOS, OVN, OVH or dICP0 has substantially comparable replication ability in tumor cells (e.g., U-2 OS cells).

FIG. 7 shows the virus titers at different time points (12 h, 24 h, 36 h, 48 h and 60 h after infection) after infection of monolayer U-2 OS cells with virus KOS, OVN, OVH or dICP0 at a MOI of 0.01. The results in FIG. 7 show that the virus KOS, OVN, OVH or dICP0 had substantially comparable replication ability in tumor cells (e.g., U-2 OS cells).

FIGS. 8A and 8B shows the cell survival rate after 72 h of infection of L-O2 cells (FIG. 8A) or U-2 OS cells (FIG. 8B) with virus KOS, OVN, OVH or dICP0 at a MOI of 1; wherein MOCK represents the cells without being infected with the virus. The results in FIG. 8A show that after 72 h of infection, the killing abilities of the viruses KOS and dICP0 to L-O2 cells were about 91.5% and 89%, respectively (both of them had significantly killing abilities to L-O2 cells); the killing abilities of the viruses OVN and OVH to L-O2 cells were about 42% and 5%, respectively (their killing abilities to L-O2 cells were significantly decreased). The results in FIG. 8B show that the viruses KOS, OVN, OVH and dICP0 could kill 100% of U-2 OS cells after infection for 72 h (all of them had very strong killing abilities to U-2 OS cells). These results indicate that the viruses KOS and dICP0 had extremely high killing abilities to normal cells (e.g., L-O2 cells) and tumor cells (e.g., U-2 OS cells); while the viruses OVN and OVH only had high killing abilities to tumor cells (e.g., U-2 OS cells) (their killing abilities were substantially the same as those of the viruses KOS and dICP0), but their killing abilities to normal cells (e.g., L-O2 cells) were significantly decreased. For example, in L-O2 cells, the killing abilities of the viruses OVN and OVH were decreased by about 54.1% and 94.5%, respectively, as compared with the virus KOS; and the killing abilities of the viruses OVN and OVH were decreased by about 52.8% and 94.4%, respectively, as compared with the virus dICP0.

The experimental results in FIG. 6-8 show that compared with the wild-type virus KOS and the recombinant virus dICP0, the replication abilities and killing abilities of the recombinant viruses OVN and OVH in normal cells are significantly decreased, while their replication abilities and killing abilities in tumor cells were substantively the same (or only slightly decreased). This indicates that the recombinant viruses OVN and OVH of the present invention are capable of not only maintaining high replication ability and high killing ability (with good antitumor activity) in tumor cells, but also significantly reducing the virulence to normal cells. Therefore, the recombinant viruses OVN and OVH of the present invention are useful for antitumor treatment, and they have higher safety to normal cells and can be used at higher doses.

In addition, the killing abilities of the recombinant viruses OVN and OVH to various tumor cells were also determined with reference to the method described above. Briefly, tumor cells in good state and in logarithmic growth phase were seeded in 6 cm culture plates at a density of $5-7.5 \times 10^6$ cells/plate. Subsequently, the cultured tumor cells were infected with the virus OVN or OVH at a MOI of 1. After 48 hours of infection, the infected tumor cells were digested, and the survival rate of the tumor cells was calculated by trypan blue staining. In this experiment, the cells without being infected with virus were used as controls. Cell survival rate (%)=(number of viable cells after infection with virus)/(number of control cells not infected with virus)×100. A 3-well replicate was set for each group of experiments and the experimental result was the average of 3 independent experiments. The experimental results are shown in FIG. 9.

FIG. 9 shows the results of cell survival rate after infection of various tumor cells with the virus OVN or OVH for 48 h; wherein MOCK represents tumor cells that were not infected with the virus. The experimental results in FIG. 9 show that the recombinant viruses OVN and OVH could significantly kill a variety of tumor cells, including, for example, lung cancer cells H1299, H520, H1975, NCI-H358 and A549 (5 strains); liver cancer cells Huh7, Hep3B, HepG2, GSG7701, SMMC7721, Hepal-6, BEL7404, PLC/PRF, QGY7703 (9 strains); breast cancer cells MADMB231, MCF7, MADMB468 (3 strains); osteosarcoma cells U2OS and SAOS2 (2 strains); ovarian cancer cells SKOV3 and CAOV3 (2 strain); cervical cancer cells SiHA and Hela (2 strains); prostate cancer cell PC-3 (1 strain); glioma cell U87MG (1 strain); melanoma A375 (1 strain); colorectal cancer HCT116 (1 strain) and pancreatic cancer Panc1 (1 strain); and the OVN and OVH had comparable tumor killing abilities. These experimental results show that the recombinant viruses OVN and OVH of the present invention have good killing activity to various tumor cells and can be used for tumor treatment.

Example 4. Evaluation of Neurotoxicity and In Vivo Safety of Recombinant Virus OVN/OVH Herpes viruses are neurotoxic and neurologically latent, with the greatest danger being the ability to infect the central nervous system of humans or animals, leading to serious side effects such as encephalitis. Therefore, the most direct and sensitive way to assess the safety of herpes viruses is to inject the virus intracranially into young mice and assess the direct killing of the mouse central nervous system by the virus. In this example, we evaluated the neurotoxicity and safety of various recombinant HSV-1 viruses in mice using a mouse encephalitis model induced by intracranial injection of virus.

Briefly, 4-6 weeks old BALB/c female mice (n=10) were used as experimental subjects, and 20 μl of virus was slowly injected intracranially at the left anterior lobe of brain, near the junction of coronal suture and sagittal suture. After the injection, the incidence and survival of the mice were observed every day. FIG. 10 shows the survival rate of mice after intracranial injection of virus KOS, dICP0, OVN or OVH at a given dose; wherein Vehicle represents mice without being injected with virus.

The results show that when intracranial injection of $1\times10^4$ PFU of wild-type virus KOS, 100% of the mice developed moderate to severe side effects; after the onset of disease, the mice were often accompanied by symptoms such as hair rising, anorexia, cold, dilatory, and even paralyzed; and 100% of mice died within 4-6 days after virus injection (FIG. 10). When intracranial injection of $1\times10^5$ PFU of virus dICP0, about 80% of mice died within 4-8 days after virus injection, and only 20% of the mice gradually recovered after one week.

When a high dose ($1\times10^7$ PFU) of virus OVN was injected intracranially, no mice (0/10) died during the entire experimental period, and the survival rate of the mice was 100%. This indicates that compared with the wild-type virus KOS and the recombinant virus dICP0, the neurotoxicity of the virus OVN was significantly decreased, the safety in vivo was remarkably improved, and the doses used could be increased by at least 1000 times and 100 times, respectively.

When a higher dose ($4\times10^7$ PFU) of virus OVN was injected intracranially, only one mouse (1/10) died during the entire experimental period, and the mouse survival rate was 90%. This indicates that the virus OVN had a half-lethal dose higher than $4\times10^7$ PFU in mice, and thus had excellent in vivo safety.

When $4\times10^7$ PFU of virus OVH was injected intracranially, no mice (0/10) died during the entire experimental period, and the mouse survival rate was 100%. And, more importantly, the mice did not show any adverse reactions throughout the experimental period. This indicates that the virus OVH had further significantly decreased neurotoxicity and further significantly improved the safety in vivo, as compared to the virus OVN.

The above experimental results show that the viruses OVN and OVH of the present invention have low neurotoxicity, high safety in vivo, and have broad application prospects.

Example 5. Evaluation of Therapeutic Potential of Recombinant Virus OVN/OVH

Tumor cells (Huh7 and Hepal-6) were cultured in complete medium comprising 10% calf serum in a 37° C., 5% $CO_2$ incubator. When the cells were grown to logarithmic growth phase, the cells were digested with 0.05% trypsin and washed with PBS to obtain a cell suspension (cell density of $5\times10^7$/mL) resuspended in PBS.

0.1 mL of Huh7 cell suspension was inoculated subcutaneously into the right flank of each of 5-6 weeks old nude mice. When the tumor on mouse back grew to 6 mm×6 mm (tumor volume was approximately 100 mm³), the mice were grouped (n=8/group) and treatment was started (Day 0). The treatment regimen was as follows: $1\times10^7$ PFU virus (OVN or OVH) or the same volume of DMEM (used as a control) was injected intratumorally, once every 3 days, for a total of 3 injections.

0.1 mL of Hepal-6 cell suspension was inoculated subcutaneously on the left and right flanks of each of 5-week-old mice (C57BL/6). When the tumor on mouse back grew to 6 mm×6 mm (tumor volume was approximately about 100 mm³), the mice were grouped and treatment was started. The treatment regimen was as follows: $1\times10^7$ PFU virus (OVN or OVH) or the same volume of DMEM was injected intratumorally, once every 3 days, for a total of 3 injections.

The status of mice was monitored every 3 days and the tumor size was measured using an electronic vernier caliper. Tumor volume and tumor inhibition rate were calculated according to the following formula:

$$V(\text{volume}) = [L\times(W)^2]/2;\ L \text{ represents a long diameter,}$$
$$\text{and } W \text{ represents a short diameter.}$$

$$\text{Tumor inhibition rate} = (\text{tumor volume of control}$$
$$\text{group} - \text{tumor volume of experimental group})/$$
$$\text{tumor volume of control group} \times 100\%.$$

The experimental results are summarized in FIG. 11-12.

FIG. 11 shows the tumor volume-time curves (FIG. 11A) and survival rate-time curves (FIG. 11B) of the nude mice inoculated with Huh7 cells after treatment with OVN or OVH; wherein DMEM represents untreated mice. The results of FIG. 11A show that after three doses of virus injections, both the recombinant viruses OVN and OVH significantly inhibited tumor growth; on day 21, the inhibition rate of OVN reached 86.1%, and the inhibition rate of OVH reached 78%. The results in FIG. 11B show that after three virus injections, the recombinant viruses OVN and OVH significantly prolonged the survival time of tumor-bearing nude mice; on day 60, the control group of nude mice died completely, while the nude mice administrated with the recombinant virus OVN or OVH still had a survival rate of 75% after the end of the experiment.

FIG. 12 shows the tumor volume-time curves of tumors on left flank (FIG. 12A) and tumors on right flank (FIG. 12B) of mice (C57BL/6) inoculated with Hepal-6 cells after treatment with OVN or OVH; wherein DMEM represents untreated mice. The results in FIG. 12 show that after three doses of virus injections on the right flank tumors, the recombinant viruses OVN and OVH not only safely cleared the right flank tumors of the mice, but also cleared the left flank tumors.

These experimental results have confirmed that the viruses OVN and OVH of the present invention have significant potential for treating tumors in vivo, and have broad application prospects.

Example 6. Construction and Characterization of Other Recombinant Viruses (1)

In this example, a series of derived recombinant viruses were constructed based on the recombinant viruses OVN and OVH.

Referring to the method described in Example 1 (particularly 1.3.1 to 1.3.3), the recombinant virus OVN was used as the starting virus, and the hTERT core promoter sequence was introduced into the recombinant virus OVN genome by the recombinant plasmid for regulating the VP5 gene or the ICP4 gene, thereby constructing recombinant viruses OVH1 and OVH2.

After being verified by sequencing, the native promoter sequence of the VP5 gene (nt40729 to nt40475 of the wild-type HSV-1 genome (GenBank: JQ673480.1)) had been substituted with the hTERT core promoter sequence (SEQ ID NO: 5) in the recombinant virus OVH1 genome compared with the recombinant virus OVN; in the recombinant virus OVH2 genome, the native promoter sequence of the ICP4 gene (nt146151 to nt146867 and nt131706 to nt130990 of the wild-type HSV-1 genome (GenBank: JQ673480.1)) had been substituted with the hTERT core promoter sequence (SEQ ID NO: 5).

FIG. 13 is a schematic illustration showing the differences in genome structure between the recombinant viruses OVH, OVH1 and OVH2 and the recombinant virus OVN; wherein, the native promoter sequence of the ICP27 gene of the recombinant virus OVH, the native promoter sequence of the VP5 gene of the recombinant virus OVH1, and the native promoter sequence of the ICP4 gene of the recombinant virus OVH2 were substituted with the hTERT core promoter sequence, respectively, as compared with the recombinant virus OVN.

Further, referring to the method described in Example 1 (particularly 1.3.1 to 1.3.3), the recombinant virus d34.5/01acZ was used as the starting virus, and the nucleotide sequence encoding the GFP protein (SEQ ID NO: 7) and the nucleotide sequence encoding the anti-human PD-1 single chain antibody (SEQ ID NO: 8) were introduced into the recombinant virus d34.5/01acZ genome to replace the lacZ gene by using recombinant plasmids, thereby constructing and obtaining the recombinant viruses OVN-GFP And OVN-PD-1-scfv. After being verified by sequencing, compared with the recombinant virus d34.5/01acZ, in the recombinant virus OVN-GFP genome, the two copies of the lacZ gene had been substituted with the nucleotide sequence encoding the GFP protein (i.e., in the genome of the recombinant virus OVN-GFP, the sequence of nt510 to nt5439 and the sequence of nt120802 to nt125731 of the wild-type HSV-1 genome (GenBank: JQ673480.1) were substituted with the nucleotide sequence encoding the GFP protein); in the genome of the recombinant virus OVN-PD-1-scfv, the two copies of the lacZ gene had been substituted with the nucleotide sequence encoding the PD-1 single-chain antibody (i.e., in the genome of the recombinant virus OVN-PD-1-scfv, the sequence of nt510 to nt5439 and the sequence of nt120802 to nt125731 of the wild-type HSV-1 genome (GenBank: JQ673480.1) were substituted with the nucleotide sequence encoding the PD-1 single chain antibody).

Further, the recombinant virus OVN-GFP and OVN-PD-1-scfv were used as the starting viruses, and the hTERT core promoter sequence was introduced into the starting virus genome to regulate the ICP27 gene by using plasmids PUC57-27p/lacZ and PUC57-27p/htert, thereby constructing and obtaining recombinant viruses OVH-GFP and OVH-PD-1-scfv.

After being verified by sequencing, compared with recombinant virus OVN-GFP, the native promoter sequence of the ICP27 gene (nt113423 to nt113589 of the wild-type HSV-1 genome (GenBank: JQ673480.1)) in the recombinant virus OVH-GFP genome had been substituted with the hTERT core promoter sequence (SEQ ID NO: 5). Compared with the recombinant virus OVN-PD-1-scfv, the native promoter sequence of the ICP27 gene (nt113423 to nt113589 of the wild-type HSV-1 genome (GenBank: JQ673480.1)) in the recombinant virus OVH-PD-1-scfv genome had been substituted with the hTERT core promoter sequence (SEQ ID NO: 5).

FIG. 14 is a schematic illustration showing the genome structure differences of recombinant viruses d34.5/01acZ, OVN, OVN-GFP, OVN-PD-1-scfv, OVH-GFP and OVH-PD-1-scfv.

U-2 OS cells (purchased from ATCC, USA, item number HTB-96™) were seeded in 6 cm culture plates at a density of 1×10⁶ cells. After the cells were grown into a monolayer, the cells were infected with the recombinant viruses OVN-GFP and OVH-GFP, respectively. After cytopathic effect was observed, the cells infected with the recombinant viruses OVN-GFP and OVH-GFP were observed under a fluorescence microscope. The results are shown in FIG. 15. FIG. 15 shows the results of the fluorescence microscopic observation of the U-2 OS cells infected with the recombinant virus OVN-GFP or OVH-GFP. The results in FIG. 15 show that the OVN-GFP and OVH-GFP infected U-2 OS cells were capable of emitting green fluorescence. This indicates that the recombinant viruses OVN-GFP and OVH-GFP were capable of expressing GFP protein after infection of the host cells.

U-2 OS cells (purchased from ATCC, USA, catalogue number HTB-96™) were seeded in 6 cm culture plates at a density of 1×10⁶ cells. After the cells were grown into a monolayer, the cells were infected with the recombinant viruses OVH and OVH-PD-1-scfv, respectively. The culture supernatants of the cells were harvested for after 24 h and 48 h of infection, respectively, for subsequent analysis. The supernatant collected 48 h after infection was subjected to serial 2-fold gradient dilutions, and the ability of supernatant of each dilution to inhibit interaction between PD-1 and PD-L1 was determined by an ELISA method based on competition between PD-1 single-chain antibody and PD-L1 protein for binding to PD-1 protein. In addition, the abilities of the supernatants collected at 24 h and 48 h after infection to bind PD-1 was also determined by an ELISA method based on the reactivity between PD-1 single-chain antibody and PD-1 protein. The experimental results are shown in FIG. 16.

FIG. 16 shows after infection of U-2 OS cells with recombinant virus OVH or OVH-PD-1-scfv for 24 h or 48 h, the ability of the cell supernatants to inhibit the specific binding of PD-1/PD-L1 (FIG. 16A), and the results of analysis of the interaction between the cell supernatants and the PD-1 protein (FIG. 16B); wherein MOCK represents tumor cells without being infected with the virus. The results in FIG. 16 show that the supernatants of OVH-PD-1-scfv-infected U-2 OS cells were capable of inhibiting the specific binding of PD-1/PD-L1 and were capable of specifically binding to PD-1. This indicates that the recombinant virus OVH-PD-1-scfv expressed a PD-1 single-chain antibody after infection of host cells, which bound to PD-1 and blocked the interaction between PD-1 and PD-L1.

The experimental results of FIG. 15-16 indicate that the genomes of the recombinant viruses OVN and OVH of the present invention are useful as viral vectors for carrying and expressing foreign genes.

In addition, the abilities of the recombinant viruses OVH and OVH-PD-1-scfv to treat tumors were also verified in mice (C57BL/6) inoculated with Hepal-6 cells according to the method described in Example 5. The results are shown in FIG. 17.

FIG. 17 shows the tumor volume-time curves of tumors on left flank (FIG. 17A) and tumors on right flank (FIG. 17B) of mice (C57BL/6) inoculated with Hepal-6 cells after treatment with OVH or OVH-PD-1-scfv; wherein Vehicle represents untreated mice. The results in FIG. 17 show that after three doses of virus injections on the right flank tumors, the recombinant viruses OVH and OVH-PD-1-scfv not only safely cleared the right flank tumors of the mice, but also cleared the left flank tumors.

These experimental results confirm that the recombinant viruses OVH-PD-1-scfv and OVH of the present invention have significant potential for treating tumors in vivo, and have broad application prospects.

Example 7. Construction and Characterization of Other Recombinant Viruses (2)

In this example, a series of derived recombinant viruses were constructed based on the recombinant virus OVN. Briefly, with reference to the method described in Example 1 (especially 1.3.1 to 1.3.3), the recombinant virus OVN was used as the starting virus, and the non-essential gene UL41, UL43, UL48, UL55, US2, LAT or NF in the recombinant virus OVN genome was deleted by using recombinant plasmids, respectively, thereby constructing and obtaining recombinant viruses OVN-dUL41, OVN-dUL43, OVN-dUL48, OVN-dUL55, OVN-dUS2, OVN-dLAT and OVN-dNF.

According the verification by sequencing, compared with the recombinant virus OVN, the recombinant virus OVN-dUL41 genome had a deletion of the UL41 (vhs) gene (GenBank: AFE62869.1; corresponding to nt91088 to nt92557 of the wild-type HSV-1 genome (GenBank: JQ673480.1)); the recombinant virus OVN-dUL43 genome had a deletion of the UL43 gene (GenBank: AFE62871.1; corresponding to nt94721 to nt95968 of the wild-type HSV-1 genome (GenBank: JQ673480.1)); the recombinant virus OVN-dUL48 genome had a deletion of the UL48 (VMW65) gene (GenBank: AFE62876.1; corresponding to nt103527 to nt104999 of the wild-type HSV-1 genome (GenBank: JQ673480.1)); the recombinant virus OVN-dUL55 genome had a deletion of the UL55 gene (GenBank: AFE62884.1; corresponding to nt115418-nt115978 of the wild-type HSV-1 genome (GenBank: JQ673480.1)); the recombinant virus OVN-dUS2 genome had a deletion of the US2 gene (GenBank: AFE62890.1; corresponds to nt133911 to nt134786 of the wild-type HSV-1 genome (GenBank: JQ673480.1); the recombinant virus OVN-dLAT genome had a deletion of the LAT gene (corresponding to nt4781 to nt7062 of the wild-type HSV-1 genome (GenBank: JQ673480.1)); and, the recombinant virus OVN-dNF genome had a deletion of the nucleotide fragment (NF) (corresponding to nt5853 to nt7485 of the wild-type HSV-1 genome (GenBank: JQ673480.1)).

Alternatively, CRISPR technology can also be used, for example, by designing specific sgRNA primers and using the commercially available LentiCRISPR v2 vector (Addgene), the non-essential gene UL41, UL43, UL48, UL55, US2, LAT or NF in the recombinant virus OVN genome could be deleted, respectively.

Information on the non-essential genes UL41, UL43, UL48, UL55, US2, LAT and NF is also provided in Table 4.

TABLE 4

Information on non-essential genes

| Gene name | GenBank No. | Sites in genome | SEQ ID NO: |
|---|---|---|---|
| UL41 (vhs) | AFE62869.1 | nt91088-nt92557 | 17 |
| UL43 | AFE62871.1 | nt94721-nt95968 | 18 |
| UL48 (VMW65) | AFE62876.1 | nt103527-nt104999 | 19 |
| UL55 | AFE62884.1 | nt115418-nt115978 | 20 |
| US2 | AFE62890.1 | nt133911-nt134786 | 21 |
| LAT | Derived from JQ673480.1 | nt4781-nt7062 | 22 |
| Nucleotide fragment (NF) | Derived from JQ673480.1 | nt5853-nt7485 | 23 |

Tumor cells (U-2 OS cells) in good condition and in logarithmic growth phase were seeded in 6 cm culture plates at a density of 5-7.5×10$^6$ cells/plate. Subsequently, the cultured cells were infected with the recombinant virus OVN, OVN-dUL41, OVN-dUL43, OVN-dUL48, OVN-dUL55, OVN-dUS2, OVN-dLAT or OVN-dNF, respectively, at a MOI of 0.01. After 60 h of infection, the virus titer of the above recombinant virus was determined by referring to the protocol described in Example 1. A 3-well replicate was set for each group of experiments and the experimental result was the average of 3 independent experiments. The experimental results are shown in FIG. 18.

FIG. 18 shows the virus titers after 60 h of infection of U-2 OS cells with virus OVN, OVN-dUL41, OVN-dUL43, OVN-dUL48, OVN-dUL55, OVN-dUS2, OVN-dLAT or OVN-dNF, respectively, at a MOI of 0.01. The results in FIG. 18 show that after infection of U-2 OS cells, the viruses OVN, OVN-dUL55, OVN-dUS2, OVN-dLAT and OVN-dNF showed replication at high levels: after 60 h of infection, their viral titers were between 1.01-1.18×10$^8$ pfu/ml, on the order of 10$^8$ pfu/ml; while the viruses OVN-dUL43, OVN-dUL41 and OVN-dUL48 showed replication at low levels: after 60 h of infection, their virus titers were lower than 10$^7$ pfu/ml, on the order of 10$^4$ to 10$^6$ pfu/ml. The viral titers of these recombinant viruses are also provided in Table 5.

TABLE 5

Viral titers of recombinant viruses after 60 h of infection of U-2 OS cells

| Recombinant virus | Viral titer (pfu/ml) | Recombinant virus | Viral titer (pfu/ml) |
|---|---|---|---|
| OVN | $1.01 \times 10^8 \pm 8.54 \times 10^6$ | OVN-dUL55 | $1.05 \times 10^8 \pm 5.00 \times 10^6$ |
| OVN-dUL41 | $1.80 \times 10^5 \pm 2.65 \times 10^4$ | OVN-dUS2 | $1.18 \times 10^8 \pm 2.89 \times 10^6$ |
| OVN-dUL43 | $1.83 \times 10^6 \pm 2.89 \times 10^5$ | OVN-dLAT | $1.07 \times 10^8 \pm 5.77 \times 10^6$ |
| OVN-dUL48 | $3.37 \times 10^4 \pm 3.21 \times 10^3$ | OVN-dNF | $1.02 \times 10^8 \pm 7.64 \times 10^6$ |

These results indicate that the viruses OVN, OVN-dUL55, OVN-dUS2, OVN-dLAT, and OVN-dNF were capable of replicating at high levels in tumor cells (e.g., U-2 OS cells); whereas the replication abilities of the viruses OVN-dUL43, OVN-dUL41 and OVN-dUL48 in tumor cells (e.g., U-2 OS cells) were significantly decreased. For example, in U-2 OS cells, the replication abilities of the viruses OVN-dUL41, OVN-dUL43 and OVN-dUL48 were decreased by about 561 times, 55 times, and 3×10$^3$ times, respectively, as compared to the virus OVN.

In addition, the cultured normal cells (L-O2 cells) or tumor cells (U-2 OS cells) were infected with the recombinant virus OVN, OVN-dUL41, OVN-dUL43, OVN-dUL48, OVN-dUL55, OVN-dUS2, OVN-dLAT or OVN-dNF, respectively, at a MOI of 0.5. After 72 hours of infection, the survival rate of the cells was determined. A 3-well replicate was set for each set of experiments and the experimental result was the average of 3 independent experiments. The experimental results are shown in FIG. 19.

FIG. 19 shows the cell survival rate of normal cells (L-O2 cells; FIG. 19A) or tumor cells (U-2 OS cells; FIG. 19B) after 72 h of infection with the virus OVN, OVN-dUL41, OVN-dUL43, OVN-dUL48, OVN-dUL55, OVN-dUS2, OVN-dLAT or OVN-dNF, respectively, at a MOI of 0.5.

The results of FIG. 19A show that the killing rates of the viruses OVN-dUL41 and OVH-dUL48 on L-O2 cells after 72 h of infection were about 17.67% and 14.33%, respectively; the killing abilities of both on L-O2 cells were stronger than that of the virus OVN. The killing rates of the viruses OVN-dUL43, OVN-dUL55, OVN-dUS2, OVNdLAT and OVN-dNF on L-O2 cells were between 8.33% and 11.00%, which were not significantly different from that of the virus OVN.

The results in FIG. 19B show that the killing rates of the viruses OVN, OVN-dUL55, OVN-dUS2, OVN-dLAT and OVN-dNF on U-2 OS cells after 72 h of infection were 100% (i.e., having extremely high killing ability on the tumor cells). The killing abilities of the viruses OVN-dUL41, OVN-dUL43 and OVN-dUL48 on U-2 OS cells was significantly decreased.

The killing rates of these recombinant viruses against L-O2 and U-2 OS cells are also provided in Table 6.

TABLE 6

Killing rates of recombinant viruses against L-O2 cells and U-2 OS cells

| Recombinant virus | Killing rate | |
|---|---|---|
| | L-O2 cells | U-2 OS cells |
| OVN | 90.00% ± 1.00% | 0.87% ± 0.71% |
| OVN-dUL41 | 82.33% ± 0.58% | 76.00% ± 2.65% |
| OVN-dUL43 | 89.00% ± 1.00% | 52.67% ± 0.58% |
| OVN-dUL48 | 85.67% ± 1.15% | 68.33% ± 0.58% |
| OVN-dUL55 | 90.33% ± 0.58% | 0.90% ± 0.10% |
| OVN-dUS2 | 90.67% ± 0.58% | 0.77% ± 0.06% |
| OVN-dLAT | 90.33% ± 0.58% | 0.46% ± 0.05% |
| OVN-dNF | 91.67% ± 0.58% | 0.90% ± 0.10% |

These results indicate that, similar to the virus OVN, the viruses OVN-dUL55, OVN-dUS2, OVN-dLAT and OVN-dNF had only very limited killing activity to normal cells (e.g., L-O2 cells), whereas their killing abilities to tumor cells (e.g., U-2 OS cells) were extremely high; this indicates that the four recombinant viruses were equivalent to the virus OVN. Compared with the virus OVN, the viruses OVN-dUL41 and OVH-dUL48 not only had enhanced killing ability to normal cells (e.g., L-O2 cells), but also had significantly decreased killing ability to tumor cells (e.g., U-2 OS cells); which indicate that the two recombinant viruses had increased toxicity to normal cells and decreased antitumor activity. Although the killing activity of the virus OVN-dUL43 to normal cells (e.g., L-O2 cells) was not significantly enhanced as compared with the virus OVN, its killing activity to tumor cells (e.g., U-2 OS cells) was significantly decreased.

Specifically, in normal cells, the killing abilities of the viruses OVN-dUL41, OVN-dUL43 and OVH-dUL48 were increased by about 7.67%, 1.00%, and 4.33%, respectively, as compared to the virus OVN. In tumor cells, the killing abilities of the viruses OVN-dUL41, OVN-dUL43 and OVH-dUL48 were decreased by about 75.13%, 51.80% and 67.46%, respectively, as compared to the virus OVN.

The above experimental results indicate that in the recombinant HSV virus of the present invention, non-essential genes other than UL41, UL43 and UL48 (e.g., UL55, US2, LAT and NF) may be further modified, for example, inserted with a loss-of-function mutation, or deleted.

Although the specific embodiments of the invention have been described in detail, it would be understood by those skilled in the art that various modifications and changes can be made in the details of the present invention. The full scope of the invention is given by the appended claims and any equivalents thereof.

What is claimed is:

1. A recombinant herpes simplex virus (HSV), which does not express a functional ICP0 protein and ICP34.5 protein; but is capable of expressing a functional UL43 protein, a functional UL41 protein, a functional UL48 protein, or any combination thereof; and wherein the genome of the recombinant HSV comprises the following modifications:

two copies of the ICP0 gene each independently comprising a loss-of-function mutation or which is deleted or substituted with an exogenous nucleotide sequence;

two copies of the ICP34.5 gene each independently comprising a loss-of-function mutation or which is deleted or substituted with an exogenous nucleotide sequence; and wherein the genome of the recombinant HSV further comprises a modification in which a native promoter of one or more HSV genes is substituted with a tumor-specific promoter.

2. The recombinant HSV according to claim 1, wherein the genome of the recombinant HSV comprises:

(1) a UL43 gene capable of expressing a functional UL43 protein, (2) a UL41 gene capable of expressing a functional UL41 protein, (3) a UL48 gene capable of expressing a functional UL48 protein, or (4) any combination of (1) to (3).

3. The recombinant HSV according to claim 1, wherein the recombinant HSV further comprises an additional exogenous nucleotide sequence.

4. A viral vector, comprising the genome of the recombinant HSV according to claim 1.

5. An isolated host cell, which comprises one of the following:

(1) the recombinant HSV according to claim 1, or
(2) the genome of the recombinant HSV of claim 1, or
(3) a viral vector comprising the genome of the recombinant HSV of claim 1.

6. A method of obtaining the recombinant HSV according to claim 1, comprising:

(1) cultivating a host cell, which is infected with the recombinant HSV, or comprises a genome of the recombinant HSV, or is transfected with a viral vector comprising a genome of the recombinant HSV;

(2) collecting and lysing the host cell after the host cell shows signs of infection, to obtain a lysate of the host cell; and (3) recovering the recombinant HSV from the lysate.

7. A pharmaceutical composition, which comprises one or more of the following and a pharmaceutically acceptable carrier or excipient:

(1) the recombinant HSV according to claim 1,
(2) the genome of the recombinant HSV of claim 1, and
(3) a viral vector comprising the genome of the recombinant HSV of claim 1.

8. A method of treating a tumor, which comprises administering to a subject in need thereof a therapeutically effective amount of one or more of the following:
(1) the recombinant HSV according to claim 1,
(2) a viral vector comprising the genome of the recombinant HSV of claims 1, and
(3) a pharmaceutical composition comprising the recombinant HSV of (1) or the viral vector of (2).

9. The recombinant HSV according to claim 1, wherein in the genome of the recombinant HSV:
(1) the two copies of the ICP0 genes each independently comprises a loss-of-function mutation; and, the two copies of the ICP34.5 gene each independently comprises a loss-of-function mutation; or
(2) the two copies of the ICP0 genes each independently comprises a loss-of-function mutation; and the two copies of the ICP34.5 gene are deleted; or
(3) the two copies of the ICP0 genes each independently comprises a loss-of-function mutation; and the two copies of the ICP34.5 gene each is independently substituted with an exogenous nucleotide sequence; or
(4) the two copies of the ICP0 gene are deleted; and, the two copies of the ICP34.5 gene each independently comprises a loss-of-function mutation; or
(5) the two copies of the ICP0 gene are deleted; and the two copies of the ICP34.5 gene are deleted; or
(6) the two copies of the ICP0 gene are deleted; and the two copies of the ICP34.5 gene each is independently substituted with an exogenous nucleotide sequence; or
(7) the two copies of the ICP0 gene each is independently substituted with an exogenous nucleotide sequence; and, the two copies of the ICP34.5 gene each independently comprises a loss-of-function mutation; or
(8) the two copies of the ICP0 gene each is independently substituted with an exogenous nucleotide sequence; and the two copies of ICP34.5 genes are deleted; or
(9) the two copies of the ICP0 gene each is independently substituted with an exogenous nucleotide sequence; and the two copies of the ICP34.5 gene each is independently substituted with an exogenous nucleotide sequence.

10. The recombinant HSV according to claim 9, wherein
a) the loss-of-function mutation each is independently selected from the group consisting of: missense mutation, nonsense mutation, frameshift mutation, base deletion, base substitution, base addition, and any combination thereof;
b) the exogenous nucleotide sequence each independently encodes a foreign protein selected from the group consisting of: fluorescent protein, immunomodulatory polypeptide, cytokine, chemokine, antibody, and cytotoxic peptide, or
c) a combination of a) and b).

11. The recombinant HSV according to claim 10, having any one or more of the following:
(1) the fluorescent protein is selected from the group consisting of green fluorescent protein, red fluorescent protein, blue fluorescent protein, yellow fluorescent protein, and any combination thereof;
(2) the immunomodulatory polypeptide is selected from the group consisting of CD40L, OX40L, inducible costimulatory molecule (ICOS), FTL3L, LIGHT, CD137L, CD70, 4-1BB, GITR, CD28, and any combination thereof;
(3) the cytokine is selected from the group consisting of interleukin, interferon, tumor necrosis factor, colony stimulating factor, and any combination thereof;
(4) the chemokine is selected from the group consisting of CCL2, RANTES, CCL7, CCL9, CCL10, CCL12, CCL15, CCL19, CCL21, CCL20, XCL-1, and any combination thereof;
(5) the cytotoxic peptide is selected from the group consisting of thymidine kinase TK (TK/GCV), TRAIL, FasL, and any combination thereof; and
(6) the antibody is selected from the group consisting of anti-PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody, anti-EGFR antibody, anti-VEGFR antibody, anti-HER2 antibody, anti-PDGFR antibody, and any combination thereof.

12. The recombinant HSV according to claim 2, wherein the recombinant HSV is further characterized by:
(1) one or more non-essential genes are deleted or mutated;
(2) except for the two copies of the ICP0 gene and the two copies of the ICP34.5 gene, the genome of the recombinant HSV comprises all other genes of the wild-type HSV, and none of the other genes comprises a loss-of-function mutation; or
(3) the tumor-specific promoter is a promoter of hTERT.

13. The recombinant HSV according to claim 12, characterized by any one or more of the following:
(1) the non-essential gene is selected from the group consisting of UL3 gene, UL4 gene, UL14 gene, UL16 gene, UL21 gene, UL24 gene, UL31 gene, UL32 gene, US3 gene, UL51 gene, UL55 gene, UL56 gene, US2 gene, US12 gene, LAT gene, nucleotide fragment corresponding to SEQ ID NO: 23, and any combination thereof;
(2) the non-essential gene comprises a loss-of-function mutation, or is substituted with an exogenous nucleotide sequence; and
(3) the tumor-specific promoter is a promoter of hTERT having the sequence set forth in SEQ ID NO: 5.

14. The recombinant HSV according to claim 2, wherein the genome of the recombinant HSV further comprises one or more modifications selected from the group consisting of:
(1) substitution of a native promoter of the VP5 gene with a tumor-specific promoter;
(2) substitution of a native promoter of the ICP27 gene with a tumor-specific promoter;
(3) substitution of a native promoter of the ICP4 gene with a tumor-specific promoter; and
(4) deletion or mutation of one or more of the UL55 gene, the US2 gene, the LAT gene, and the nucleotide fragment corresponding to SEQ ID NO: 23.

15. The recombinant HSV according to claim 1, wherein the recombinant HSV is a recombinant HSV-1, a recombinant HSV-2, or an HSV-1/HSV-2 chimeric virus; or the recombinant HSV is derived from a HSV-1 strain KOS.

16. The recombinant HSV according to claim 3, wherein the additional exogenous nucleotide sequence encodes a foreign protein selected from the group consisting of fluorescent protein, immunomodulatory polypeptide, cytokine, chemokine, antibody, and cytotoxic peptide.

17. The isolated host cell according to claim 5, wherein the cell is a tumor cell selected from the group consisting of lung cancer cell, liver cancer cell, breast cancer cell, osteosarcoma cell, ovarian cancer cell, cervical cancer cell, prostate cancer cell, glioma cell, melanoma cell, colorectal cancer cell, and pancreatic cancer cell.

18. The pharmaceutical composition according to claim 7, characterized by any one or more of the following:
   (1) the pharmaceutical composition is formulated for treating a tumor;
   (2) the pharmaceutical composition is an injectable solution or a lyophilized powder;
   (3) the pharmaceutical composition comprises a therapeutically effective amount of the recombinant HSV or the genome of the recombinant HSV or the viral vector;
   (4) the pharmaceutical composition is a unit dose form; and
   (5) $10^2$-$10^9$ pfu of the recombinant HSV is present per unit dose of the pharmaceutical composition.

19. The method according to claim 8, characterized by any one or more of the following:
   (1) the tumor is selected from the group consisting of lung cancer, liver cancer, breast cancer, osteosarcoma, ovarian cancer, prostate cancer, glioma, melanoma, colorectal cancer, and pancreatic cancer;
   (2) the subject is a mammal; and
   (3) the subject is a human.

\* \* \* \* \*